(12) United States Patent
Yedgar

(10) Patent No.: US 8,883,761 B2
(45) Date of Patent: Nov. 11, 2014

(54) USE OF LIPID CONJUGATES IN THE TREATMENT OF DISEASES ASSOCIATED WITH VASCULATURE

(75) Inventor: Saul Yedgar, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 825 days.

(21) Appl. No.: 12/406,130

(22) Filed: Mar. 18, 2009

(65) Prior Publication Data

US 2010/0022473 A1    Jan. 28, 2010

Related U.S. Application Data

(63) Continuation-in-part of application No. 10/919,523, filed on Aug. 17, 2004, which is a continuation-in-part of application No. 09/756,765, filed on Jan. 10, 2001, now Pat. No. 7,034,006, application No. 12/406,130, which is a continuation-in-part of application No. 10/989,606, filed on Nov. 17, 2004, now Pat. No. 7,811,999, which is a continuation-in-part of application No. 10/627,981, filed on Jul. 28, 2003, now Pat. No. 7,101,859, which is a continuation-in-part of application No. 09/756,765.

(51) Int. Cl.

| A61K 31/727 | (2006.01) |
|---|---|
| A61K 31/661 | (2006.01) |
| A61K 31/80 | (2006.01) |
| A61K 47/48 | (2006.01) |

(52) U.S. Cl.
CPC ........... *A61K 47/48053* (2013.01); *A61K 31/80* (2013.01); *A61K 31/661* (2013.01)
USPC ............................................. 514/56; 514/114

(58) Field of Classification Search
None
See application file for complete search history.

(56) References Cited

U.S. PATENT DOCUMENTS

| 4,604,376 A | 8/1986 | Teng |
|---|---|---|
| 4,624,919 A | 11/1986 | Kokusho et al. |
| 4,654,327 A | 3/1987 | Teng |
| 5,064,817 A | 11/1991 | Yedgar et al. |
| 5,169,636 A | 12/1992 | Nanba et al. |
| 5,354,853 A | 10/1994 | Staveski et al. |
| 5,401,511 A | 3/1995 | Margalit |
| 5,401,777 A | 3/1995 | Ammon et al. |
| 5,464,942 A | 11/1995 | Sakurai et al. |
| 5,470,578 A | 11/1995 | Aoki et al. |
| 5,512,671 A | 4/1996 | Piantadosi et al. |
| 5,587,363 A | 12/1996 | Henderson |
| 5,707,821 A | 1/1998 | Rydel et al. |
| 5,733,892 A | 3/1998 | Sakurai et al. |
| 5,785,975 A | 7/1998 | Parikh |
| 6,022,866 A | 2/2000 | Falk et al. |
| 6,043,231 A | 3/2000 | Pruzanski et al. |
| 6,071,532 A | 6/2000 | Chaikof et al. |
| 6,162,787 A | 12/2000 | Sorgente et al. |
| 6,171,614 B1 | 1/2001 | Chaikof et al. |
| 6,180,596 B1 | 1/2001 | Tsao |
| 6,325,385 B1 | 12/2001 | Iwashita et al. |
| 6,749,813 B1 | 6/2004 | David et al. |
| 7,034,006 B2 | 4/2006 | Yedgar et al. |

(Continued)

FOREIGN PATENT DOCUMENTS

| CA | 2397016 | 7/2001 |
|---|---|---|
| EP | 0236951 | 9/1987 |

(Continued)

OTHER PUBLICATIONS

"What is Atherosclerosis?—NHLBI, NIH" NIH webpage accessed on Feb. 26, 2014. <https//www.nhlbi.nih.gov/health/health-topics/atherosclerosis/#>.*

(Continued)

*Primary Examiner* — Fereydoun G Sajjadi
*Assistant Examiner* — Amy C Bonaparte
(74) *Attorney, Agent, or Firm* — Mark S. Cohen; Pearl Cohen Zedek Latzer Baratz LLP

(57) ABSTRACT

This invention provides for the use of compounds represented by the structure of the general formula (I):

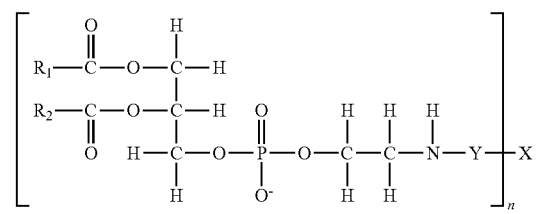

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is either a physiologically acceptable monomer, dimer, oligomer or a physiologically acceptable polymer, wherein X is a glycosaminoglycan; and
n is a number from 2 to 1,000;
wherein if Y is nothing the phosphatidylethanolamine is directly linked to X via an amide bond and if Y is a spacer, said spacer is directly linked to X via an amide or an esteric bond and to said phosphatidylethanolamine via an amide bond, thereby inhibiting the development of a psoriatic plaque or reducing plaque size in a subject.

10 Claims, 12 Drawing Sheets

(56) References Cited

U.S. PATENT DOCUMENTS

| | | | |
|---|---|---|---|
| 7,101,859 | B2 | 9/2006 | Yedgar et al. |
| 7,141,552 | B2 | 11/2006 | Yedgar et al. |
| 7,393,938 | B2 | 7/2008 | Yedgar |
| 7,504,384 | B2 | 3/2009 | Yedgar et al. |
| 7,608,598 | B2 | 10/2009 | Yedgar |
| 2002/0049183 | A1 | 4/2002 | Yedgar et al. |
| 2004/0087492 | A1 | 5/2004 | Yedgar |
| 2004/0229842 | A1 | 11/2004 | Yedgar et al. |

FOREIGN PATENT DOCUMENTS

| | | | |
|---|---|---|---|
| EP | 0529659 | | 3/1993 |
| EP | 0581281 | | 2/1994 |
| EP | 0581282 | B | 2/1994 |
| EP | 1046394 | | 10/2000 |
| JP | 04082893 | | 3/1992 |
| JP | 09030979 | | 2/1997 |
| JP | 2002345455 | | 12/2002 |
| JP | 2003160498 | | 3/2003 |
| JP | 2003335801 | | 11/2003 |
| JP | 2004018841 | | 1/2004 |
| JP | 2004170194 | | 6/2004 |
| WO | WO 87/02777 | | 5/1987 |
| WO | WO 91/00289 | | 1/1991 |
| WO | WO 93/21211 | A1 | 10/1993 |
| WO | WO 96/04001 | | 2/1996 |
| WO | WO 96/011670 | | 4/1996 |
| WO | WO 96/28544 | | 9/1996 |
| WO | WO 97/01330 | | 1/1997 |
| WO | WO97/40679 | * | 11/1997 |
| WO | WO 97/48337 | | 12/1997 |
| WO | WO 98/016198 | | 4/1998 |
| WO | WO 98/51285 | | 11/1998 |
| WO | WO 01/51003 | | 7/2001 |
| WO | WO 01/91805 | | 12/2001 |
| WO | WO 2005/084307 | | 9/2005 |

OTHER PUBLICATIONS

Weber, Nature Medicine, 2011, 17(11), p. 1410-1422.*
Cummings, B.S., "Phospholipase $A_2$ as targets for anti-cancer drugs," Biochemical Pharmacology 74 (2007), pp. 949-959.
Kokotos, G. et al., "Novel 2-Oxoamide Inhibitors of Human Group IVA Phospholipase $A_2$," J. Med. Chem., 2002, 45, pp. 2891-2893.
Ehehalt, R. et al., "Lipid Based Therapy for Ulcerative Colitis—Modulation of Intestinal Mucus Membrane Phospholipids as a Tool to Influence Inflammation," Int. J. Mol. Sci. 2010, 11, 4149-4164.
Phyllis, Dan et al., "Inhibition of Type I and Type II Phospholipase A2 by Phosphatidyl-Ethanolamine Linked to Polymeric Carriers," Biochemistry, 1998, 37 (17), pp. 6199-6204.
Extended European Search Report of European Application No. 05808267.8 issued Mar. 15, 2012.
European Office Action for European Patent Application No. 05 808 267.8 dated Aug. 26, 2013.
Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" Cancer Res 47(12):3239-45.
Balsinde, J, Balboa, MA, Yedgar, S and Dennis, EA (2000) "Group V phospholipase A(2)-mediated oleic acid mobilization in lipopolysaccharide-stimulated P388D(1) macrophages" J Biol Chem 275(7):4783-6.
Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" Br J Pharmacol 135(7) 1665-74.
Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" J Neuroimmunol 115(1-2):152-60.

Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: identification with monoclonal antibody" J Neurosci 6(7):1925-33.
Brenner, T, Poradosu, E, Soffer, D, Sicsic, C, Gazit, A and Levitzki, A (1998) "Suppression of experimental autoimmune encephalomyelitis by tyrphostin AG-556" Exp Neurol 154(2) 489-98.
Cabanas, C and Hogg, N (1993) "Ligand intercellular adhesion molecule 1 has a necessary role in activation of integrin lymphocyte function-associated molecule 1" Proc Natl Acad Sci U S A 90(12):5838-42.
Chen, WM, Soria, J, Soria, C, Krimsky, M and Yedgar, S (2002) "Control of capillary formation by membrane-anchored extracellular inhibitor of phospholipase A(2)" FEBS Lett 522(1-3).113-8.
Dan, P, Dagan, A, Krimsky, M, Pruzanski, W, Vadas, P. and Yedgar, S (1998) "Inhibition of type I and type II phospholipase A2 by phosphatidyl-ethanolamine linked to polymeric carriers" Biochemistry 37(17):6199-204.
Darville, T, Yedgar, S, Krimsky, M, Andrews, CW, Jr., Jungas, T and Ojcius, DM (2004) "Protection against Chlamydia trachomatis infection in vitro and modulation of inflammatory response in vivo by membrane-bound glycosaminoglycans" Microbes Infect 6(4):369-76.
Davidson, FF, Dennis, EA, Powell, M and Glenney, JR, Jr. (1987) "Inhibition of phospholipase A2 by "lipocortins"and calpactins. An effect of binding to substrate phospholipids" J Biol Chem 262(4) 1698-705.
Greaves MW and Camp RD (1988) "Prostaglandins, leukotrienes, phospholipase, platelet activating factor, and cytokines: an integrated approach to inflammation of human skin." Arch Dermatol Res 280:S33-41
Krimsky, M, Dagan, A, Aptekar, L, Ligumsky, M and Yedgar, S (2000) "Assessment of intestinal permeability in rats by permeation of inulin-fluorescein" J Basic Clin Physiol Pharmacol 11(2) 143-53.
Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" Am J Physiol Gastrointest Liver Physiol 285(3):G586-92.
Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" Transfusion 36(8):743-50.
Murthy, SN, Cooper, HS, Shim, H, Shah, RS, Ibrahim, SA and Sedergran, DJ (1993) "Treatment of dextran sulfate sodium-induced murine colitis by intracolonic cyclosporin" Dig Dis Sci 38(9):1722-34.
Okayasu, I, Hatakeyama, S, Yamada, M, Ohkusa, T, Inagaki, Y and Nakaya, R (1990) "A novel method in the induction of reliable experimental acute and chronic ulcerative colitis in mice" Gastroenterology 98(3):694-702.
Schmiel, DH and Miller, VL (1999) "Bacterial phospholipases and pathogenesis" Microbes Infect 1(13):1103-12.
Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" Chem Phys Lipids 104(2):149-60.
Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" Biophysical Journal 76(1): Part 2.
Schnitzer, E, Pinchuk, I, Fainaru, M, Lichtenberg, D and Yedgar, S (1998) "LDL-associated phospholipase A does not protect LDL against lipid peroxidation in vitro" Free Radic Biol Med 24(7-8):1294-303.
Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" Transplantation 73(6):984-92.

(56) References Cited

OTHER PUBLICATIONS

Yedgar, S, Lichtenberg, D and Schnitzer, E (2000) "Inhibition of phospholipase A(2) as a therapeutic target" *Biochim Biophys Acta* 1488(1-2):182-7.

Wang D.P, Matthias Schuster, Yi Fong Wang, Chi Huey Wong "Synthesis of Phospholipid-Inhibitor Conjugates by Enzymic Transphosphatidylation With Phospholipase", J. Am. Chem. Soc.; 1993; 115(23); 10487-10491.

Carey et al, "Contrasting Effects of Cycloxygenase-1 (COX-1) and COX-2 Deficiency in the Host Response to Influenze, A Viral Infection". Journ. of Immunology 2005, vol. 15: 175 (10): 6878-84.

Teitelbaum D, Arnon R, Sela M, Rabinsohn Y, Shapiro D., "Sphingomyelin Specific Antibodies Elicited by Synthetic Conjugates," Immunochemistry. Nov. 1973:10(11)135-43.

Weltzien HU, Matthiessen HP, Meyer-Delius M, Zimmermann F, Rude E., "Acidic "Peptidophospholipids", A New Class of Hapten-Bearing Cell Surface Modifying Reagents," Mol Immunol. Sep. 1984;21(9);801-10.

Winger TM, Ludovice PJ, Chaikof EL, "Lipopeptide Conjugates: Biomolecular Building Blocks for Receptor Activating Membrane-Mimetic Structures," Biomaterials. Feb. 1996;17(4):437-41.

Office Action of U.S. Appl. No. 11/220,965 Dated Mar. 27, 2008.

Office Action of U.S. Appl. No. 11/598,812 Dated Dec. 19, 2008.

Office Action of U.S. Appl. No. 10/989,606 Dated Sep. 1, 2009.

Supplementary Search Report of European Application No. 05724186.1 Dated Nov. 17, 2009.

Office Action of Japanese Application No. 2001-551427 Dated Nov. 20, 2009.

* cited by examiner

Daily Dose (mg) of MFAID

* P<0.001 as compared to untreated

Cells were seeded at 7*10³ cells per well (in 24-well plates),
in DMEM supplemented with 10%FCS, in the absence or presence
of HYPE-40 or HYPE-80 (enriched with PE), grown for 72 hours, and
counted in coulter.

Figure 12

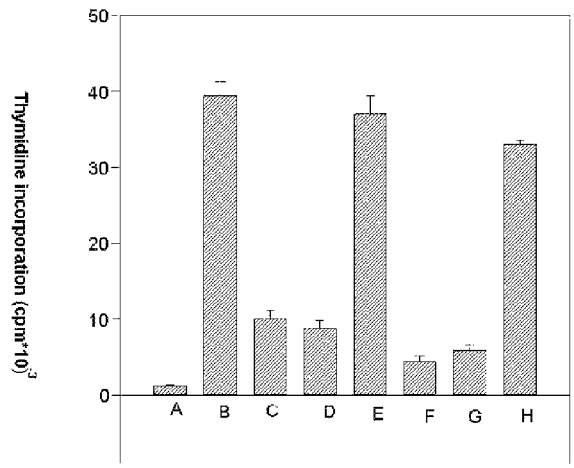

Effect of HYPE on the proliferation of bovine aortic SMCs, stimulated with thrombin (48 hours).

Legend
A - Basal, serum defficient DMEM
B - Control, thrombin
C - Thrombin, no wash-out, and after 6 hours add 50 µM HYPE
D - Thrombin+50 µM HYPE
E - Thrombin,6 hours, then wash-out of thrombin, further incubation with DMEM
F - Thrombin, 6 hours, wash-out of thrombin, add 50 µM HYPE
G - Thrombin, 6 hours ,then harvest and counting
H - DMEM+10% fetal calf serum

Figure 13

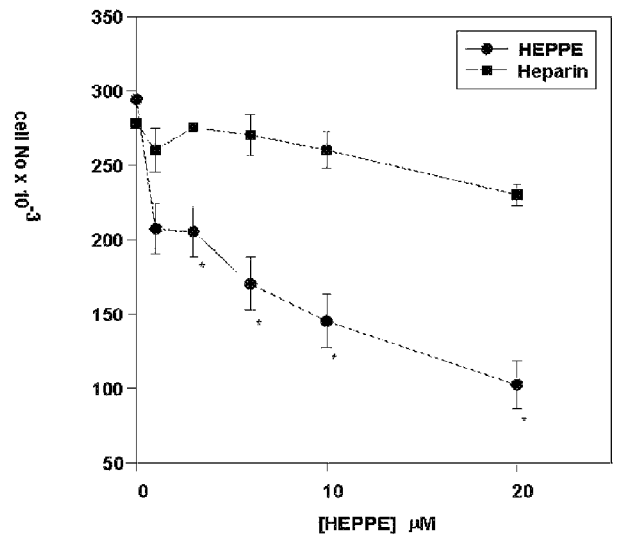

Figure 16
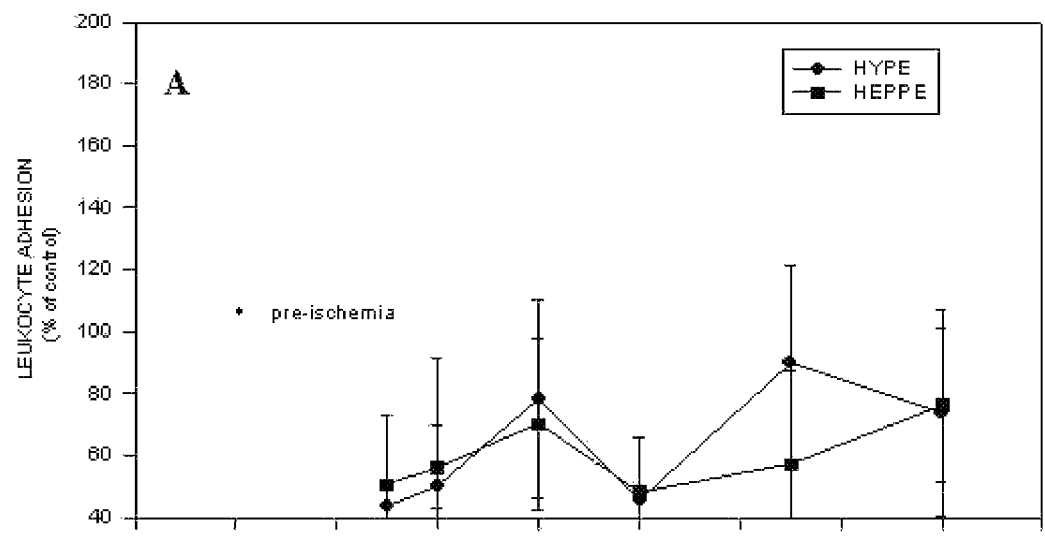
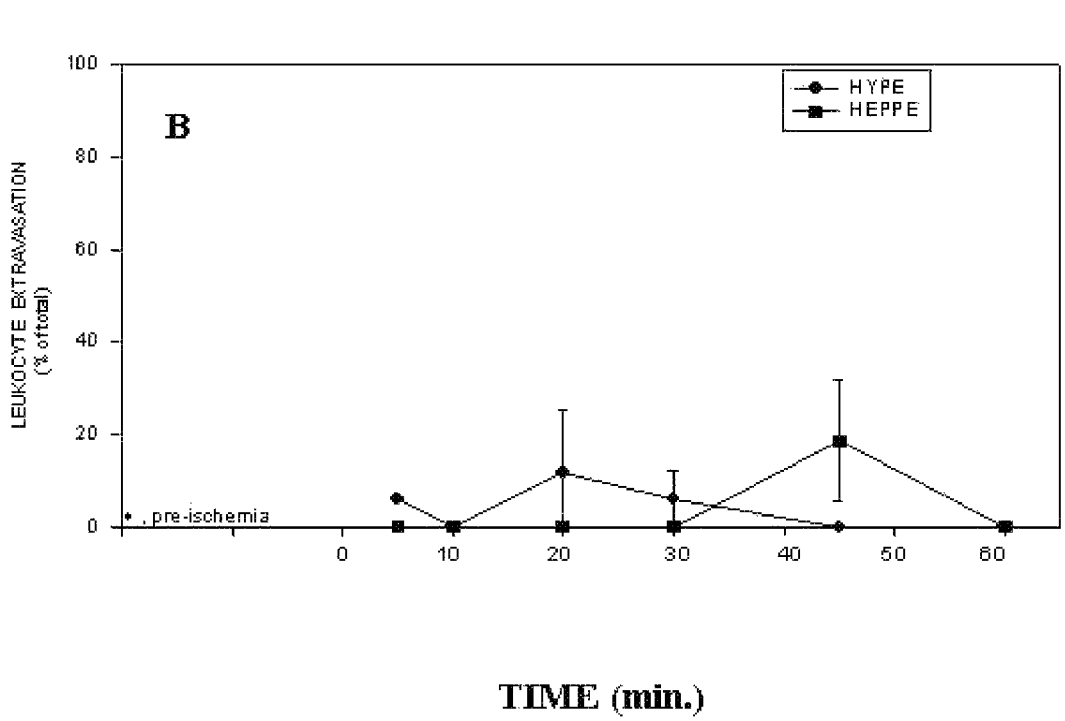

USE OF LIPID CONJUGATES IN THE TREATMENT OF DISEASES ASSOCIATED WITH VASCULATURE

CROSS-REFERENCE TO RELATED APPLICATIONS

This application is: (1) a continuation in part of U.S. application Ser. No. 10/919,523, filed Aug. 17, 2004 which is a continuation in part of U.S. application Ser. No. 09/756,765, filed Jan. 10, 2001 now U.S. Pat. No. 7,034,006; and (2) a continuation in part of U.S. application Ser. No. 10/989,606 filed Nov. 17, 2004 now U.S. Pat. No. 7,811,999, which is a continuation in part of U.S. application Ser. No. 10/627,981 filed Jul. 28, 2003 now U.S. Pat. No. 7,101,859 which is a continuation in part of U.S. application Ser. No. 09/756,765, filed Jan. 10, 2001 now U.S. Pat. No. 7,034,006. U.S. application Ser. Nos. 10/919,523, 09/756,765, 10/989,606, and 10/627,981 are hereby incorporated by reference.

FIELD OF THE INVENTION

This invention is directed to lipid-GAG conjugates and phospholipid-GAG conjugates for inhibiting angiogenesis and atherosclerosis.

BACKGROUND OF THE INVENTION

Angiogenesis literally means the birth of new blood vessels. (In Greek, "angio" means blood vessel and "genesis" means birth or beginning). Under controlled physiologic conditions it is a normal and essential process. For example, angiogenesis is a necessary part of fetal development, wound healing, and recovery from a heart attack. However, during the process of cancer growth and spread, angiogenesis allows the tumor to make its own blood supply in order to obtain the nutrients and oxygen it needs for survival. The result is a web of vessels that allows the tumor to grow even more and spread (metastasize) to other far away organs.

As the tumor grows and recruits more and more blood supply, a network of small capillaries forms and becomes disorganized. There is lack of direction to the flow of blood and empty vessels form frequently. Thus the chaotic vascular system formed results in increased pressure. As the pressure increases these vessels become "leaky". "Leaky" vessels cause the build up of proteins and plasma in the tumor mass itself forming edema. As the edema builds, tumor cells will become more starved for oxygen and other nutrients. Lack of oxygen, in turn, causes the cancer cells to secrete even more VEGF and propagate this vicious cycle.

Most angiogenesis inhibitors (anti-angiogenic drugs) work by either binding to the signaling protein (VEGF) and thereby not allowing it to interact with its complementary receptor on the endothelial cell, or, by binding to the receptor and blocking any interactions with its respective protein.

Atherosclerosis is a common form of arteriosclerosis that results from the development of an intimal lesion and subsequent narrowing of the vessel lumen. As the lesions increase in size, they reduce the diameter of the arteries and impede blood circulation. The formation of the atherosclerotic lesion is typically classified in five overlapping stages—(1) migration of smooth muscle cells, (2) lipid accumulation, (3) recruitment of inflammatory cells, (4) proliferation of vascular smooth muscle cells, and (5) extracellular matrix deposition. In a healthy vessel, the vast majority of the smooth muscle cells are contained in the vessel media. As lesions develop, smooth muscle cells migrate from the media to the intima of the vessel. Although smooth muscle cells in healthy vessel walls do not significantly accumulate lipid, the intimal smooth muscle cells have an increased capacity for lipid uptake and storage.

Lipid-conjugates having a pharmacological activity of inhibiting the enzyme phospholipase A2 (PLA2, EC 3.1.1.4) are known in the prior art. Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Since their inception, lipid-conjugates have been subjected to intensive laboratory investigation in order to obtain a wider scope of protection of cells and organisms from injurious agents and pathogenic processes.

SUMMARY OF THE INVENTION

In one embodiment, the invention provides a method of inhibiting angiogenesis comprising the step of contacting an endothelial cell with a composition comprising a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 2 to 1000;
wherein any bond between L, Z, Y and X is either an amide or an esoteric bond, thereby inhibiting angiogenesis.

In another embodiment, the invention further provides a method of inhibiting the proliferation of an endothelial cell comprising the step of contacting the endothelial cell with a composition comprising a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 2 to 1000;
wherein any bond between L, Z, Y and X is either an amide or an esoteric bond, thereby inhibiting the proliferation of an endothelial cell In another embodiment, further provided is a method of inhibiting capillary formation, inhibiting the migration of an endothelial cell, or a combination thereof, comprising the step of contacting the endothelial cell with a composition comprising a compound represented by the structure of the general formula (A):

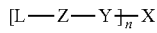

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 2 to 1000;
wherein any bond between L, Z, Y and X is either an amide or an esoteric bond, thereby inhibiting capillary formation, inhibiting migration of an endothelial cell, or a combination thereof.

In another embodiment, further provided is a method of treating a subject afflicted with macular degeneration or inhibiting the development of a macular degeneration disease in a subject, comprising the step of inhibiting neovascularization in the retina, comprising the step of administering to the subject a composition comprising a compound represented by the structure of the general formula (A):

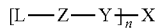

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 2 to 1000;
wherein any bond between L, Z, Y and X is either an amide or an esoteric bond, thereby treating a subject afflicted with macular degeneration in or inhibiting the development of a macular degeneration disease in a subject.

In another embodiment, further provided is a method of inhibiting the development of a hemangioma in a subject or treating a subject afflicted with hemangioma, comprising the step of administering to a subject a composition comprising a compound represented by the structure of the general formula (A):

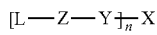

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 2 to 1000;
wherein any bond between L, Z, Y and X is either an amide or an esoteric bond, thereby inhibiting the development of a hemangioma in a subject or treating a subject afflicted with hemangioma.

In another embodiment, further provided is a method of inhibiting angiogenesis in the endometrium in a female in need thereof, comprising administering to the female a composition comprising a compound represented by the structure of the general formula (A):

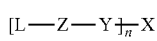

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 2 to 1000;
wherein any bond between L, Z, Y and X is either an amide or an esoteric bond, thereby inhibiting angiogenesis in the endometrium in a female.

In another embodiment, further provided is a method of treating a subject afflicted with a cancer associated with angiogenesis or inhibiting tumor development in a subject, comprising the step of administering to the subject a composition comprising a compound represented by the structure of the general formula (A):

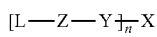

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 2 to 1000;
wherein any bond between L, Z, Y and X is either an amide or an esoteric bond, thereby treating a subject afflicted with a cancer associated with angiogenesis or inhibiting tumor development in a subject.

In another embodiment, further provided is a method of inhibiting the development of a psoriatic plaque or reducing the size of a psoriatic plaque in a subject in need thereof, comprising the step of administering to the subject a composition comprising a compound represented by the structure of the general formula (A):

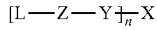

(A)

wherein
L is a lipid or a phospholipid;
Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein X is a glycosaminoglycan; and n is a number from 2 to 1000;

wherein any bond between L, Z, Y and X is either an amide or an esoteric bond, thereby inhibiting the development of a psoriatic plaque or reducing the size of a psoriatic plaque.

In another embodiment, further provided is a method of inhibiting the development of an atherosclerotic plaque, reducing plaque size, inhibiting inflammation induced by atherosclerotic plaque, or any combination thereof, comprising the step of contacting an artery afflicted with the atherosclerotic plaque with a composition comprising a compound represented by the structure of the general formula (A):

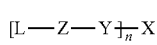

(A)

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein X is a glycosaminoglycan; and n is a number from 2 to 1000;

wherein any bond between L, Z, Y and X is either an amide or an esoteric bond, thereby inhibiting the development of an atherosclerotic plaque, reducing plaque size, inhibiting inflammation induced by atherosclerotic plaque, or any combination thereof.

BRIEF DESCRIPTION OF DRAWINGS

FIG. 12: A bar graph showing the effect of HyPE on proliferation of bovine aortic SMCs, stimulated with thrombin (48 hours).

FIG. 13: A graph showing the effect of Lipid-conjugates on proliferation of human venous smooth muscle cells.

FIG. 16: A graph showing the effect of Lipid-conjugates on ischemia/reperfusion-induced leukocyte adhesion (A) and extravasation (B) in rat cremaster muscle.

DETAILED DESCRIPTION OF THE INVENTION

Figure 1:
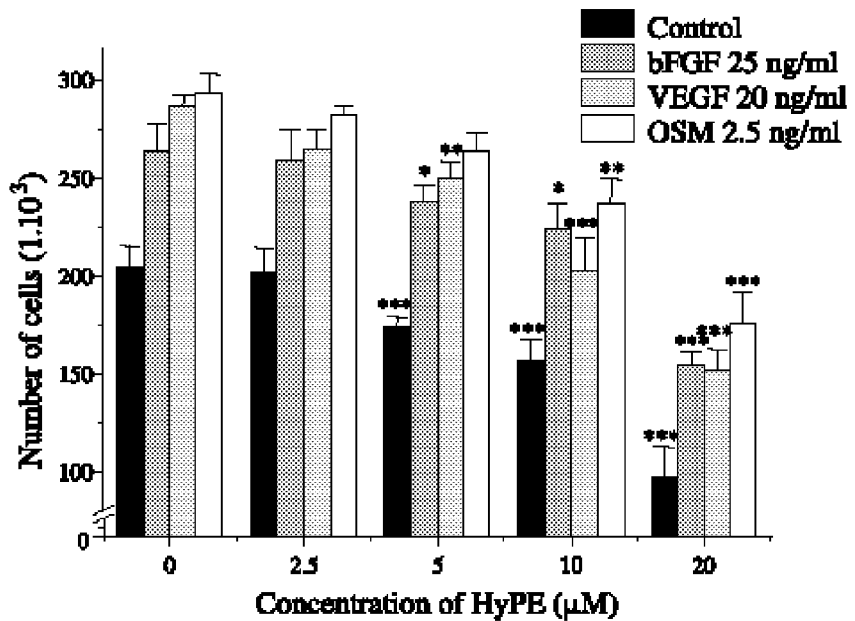
FIG. 1: A bar graph showing the Inhibitory effect induced by hyaluronic acid-linked N-derivatized phosphatidyl-ethanolamine (HyPE) on bFGF-, VEGF- and OSM-stimulated HBMEC proliferation. 50×10³ HBMEC-1 were seeded, incubated for 2 days with a minimal concentration of FCS (7.5%) to assure viability of the cells with indicated concentrations of HyPE, and with or without addition of angiogenic factors. Then cells in each well were then counted in a particle counter. Results of four experiments in duplicate, expressed as mean±S.E.M. per well. *P<0.001, P<0.01, *P<0.05, in comparison to cells without HyPE.

In one embodiment, this invention provides a method of inhibiting angiogenesis. In another embodiment, the invention provides a method of inhibiting angiogenesis in a subject. In another embodiment, the invention provides a method of inhibiting angiogenesis in a subject afflicted with cancer. In another embodiment, the invention provides a method of inhibiting angiogenesis in a tumor in a subject.

In another embodiment, the invention provides a method of inhibiting the proliferation of an endothelial cell. In another embodiment, the invention provides a method of inhibiting capillary formation. In another embodiment, the invention provides a method of inhibiting migration of an endothelial cell.

In another embodiment, the invention provides a method of inhibiting the development of an atherosclerotic plaque. In another embodiment, the invention provides a method of reducing plaque size. In another embodiment, the invention provides a method of inhibiting inflammation induced by atherosclerotic plaque.

Proliferation of vascular tissue is an element of both the atherogenesis of sclerotic plaques as well as a feature of primary and metastatic cancer lesion growth.

In one embodiment, this invention provides a method for treating a subject afflicted with malignant tumors via administration of a compound comprising a lipid or a phospholipid bonded, directly or via a spacer group, to a physiologically acceptable monomer, dimer, oligomer, or polymer. In another embodiment, this invention provides a method for inhibiting angiogenesis in a subject suffering from cancer via administration of a compound comprising a lipid or a phospholipid bonded, directly or via a spacer group, by an amide or an ester bond to a glycosaminoglycan.

In another embodiment, this invention provides a method for inhibiting the development of an atherosclerotic plaque in a subject suffering from atherosclerosis via administration of a compound comprising a lipid or a phospholipid bonded, directly or via a spacer group, by an amide or an ester bond to a glycosaminoglycan.

In one embodiment, this invention provides the use of a number of compounds, for application in inhibiting, preventing, suppressing, etc., angiogenesis, as further described hereinbelow.

In the context of the present invention, the term cardiovascular disease refers to blood vessel lumen narrowing arising in the course of atherosclerosis, vasculitis, invasive procedures, particularly catheterization of an artery or vein, and the ischemic syndromes associated with them.

In one embodiment, this invention provides administration of the conjugates for the treatment of diseases which requires controlling phospholipase A2 activities, controlling the production and/or action of lipid mediators, amelioration of damage to cell surface by glycosaminoglycans (GAG) and proteoglycans, controlling the production of oxygen radicals and nitric oxide, protection of lipoproteins from damaging agents, anti-oxidant therapy; anti-endotoxin therapy; controlling of cytokine, chemokine and interleukin production; controlling the proliferation of cells, controlling of angiogenesis and organ vascularization; inhibition of invasion-promoting enzymes, controlling of cell invasion, controlling of leukocyte activation, adhesion and extravasation, amelioration of ischemia/reperfusion injury, inhibition of lymphocyte activation, controlling of blood vessel and airway contraction, protection of blood brain barrier, controlling of neurotransmitter production and action or extracorporeal tissue preservation.

In another embodiment of the invention, the lipid-conjugates described are used in a process for manufacture of a composition for the treatment of diseases which requires controlling phospholipase A2 activities, controlling the production and/or action of lipid mediators, amelioration of damage to cell surface by glycosaminoglycans (GAG) and proteoglycans, controlling of cytokine, chemokine and interleukine production; controlling the proliferation of cells, controlling of angiogenesis and organ vascularization; inhibition of invasion-promoting enzymes, controlling of cell invasion, controlling of white cell activation, adhesion and extravasation.

Metastasis, the spread of cancer cells to ectopic sites, is frequently a vasculature dependent process as well, often referred to as hematogenous spread. The physiological barrier imposed by the blood vessel wall, comprised from elements such as endothelial cells and basement membrane substance, is normally highly selective to the passage of cells. However, metastatic cells abrogate this barrier, employing a variety of mechanisms, some of which have been established in the scientific literature. For example, such abnormal cells produce hydrolytic enzymes which degrade the extracellular matrix and associated components of the vascular barrier, such as collagenase, heparinase, and hyaluronidase. Thus a critical factor in the metastatic process is the ability of cancer cells to intrude through or permeate the wall of the blood vessel lumen, thus arriving to invade a new tissue site after travel through the circulation. Cancer cells also elaborate messenger chemicals, known as cytokines and chemokines, which enable the metastatic process and the build up of a vasculature (angiogenesis).

In other embodiments, the lipid-conjugates provide cytoprotective effects to an organism suffering from a disease, where pathophysiological mechanisms of tissue damage may comprise oxidation insult giving rise to membrane fragility; hyperproliferation behavior of cells giving rise to stenotic plaque formation in vascular tissue, angiogenesis and benign or malignant cancer disease, or psoriasis; aberrant cell migration giving rise to brain injury or tumor cell metastases; excessive expression of chemokines and cytokines associated with central nervous system (CNS) insult, sepsis, ARDS, or immunological disease; cell membrane damage giving rise to CNS insult, CVS disease, or hemolysis; peroxidation of blood proteins and cell membranes giving rise to atherosclerosis or reperfusion injury; excessive nitric oxide production giving rise to CNS insult, reperfusion injury, and septic shock; interaction with major histocompatibility antigens (MHC) associated with autoimmune diseases alloimmune syndromes, such as transplant rejection, or combinations thereof.

In another embodiment, the treatment requires protection of lipoproteins from damaging agents. In another embodiment, the treatment requires controlling the proliferation of cells. In another embodiment, the treatment requires controlling of angiogenesis and organ vascularization. In another embodiment, the treatment requires inhibition of invasion-promoting enzymes. In another embodiment, the treatment requires controlling of cell invasion. In another embodiment, the invading cells are white blood cells. In another embodiment, the invading cells are cancer cells. In another embodiment, the treatment requires controlling of white cell activation, adhesion or extravasation. In another embodiment, the treatment requires amelioration of ischemia or reperfusion injury. In another embodiment, the treatment requires inhibition of lymphocyte activation. In another embodiment, the treatment requires protection of blood brain barrier. In another embodiment, the treatment requires control of neurotransmitter production and action. In another embodiment, the treatment requires controlling of blood vessel and airway contraction. In another embodiment, the treatment requires extracorporeal tissue preservation.

In one embodiment, the invention provides a method of treating a subject afflicted with a disease, wherein the treatment of the disease requires controlling phospholipase A2 activities; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxygen radicals and nitric oxide; protection of cells, tissues, and plasma lipoproteins from damaging agents, such as reactive oxygen species (ROS) and phospholipases; anti-oxidant therapy; anti-endotoxin therapy; controlling of cytokine, chemokine and interleukine production; controlling the proliferation of cells, including smooth muscle cells, endothelial cells and skin fibroblasts; controlling of angiogenesis and organ vascularization; inhibition of invasion-promoting enzymes, such as collagenase, heparinase, heparanase and hyaluronidase; controlling of cell invasion; controlling of white cell activation, adhesion and extravasation; amelioration of ischemia/reperfusion injury, inhibition of lymphocyte activation; controlling of blood vessel and airway contraction; protection of blood brain barrier; controlling of neurotransmitter (e.g., dopamine) production and action (e.g., acethylcholine); extracorporeal tissue preservation or any combination thereof.

Compounds

In one embodiment, reference to a compound for use in a method of the present invention refers to one comprising a lipid or phospholipid moiety bound to a physiologically acceptable monomer, dimer, oligomer, or polymer. In one embodiment, the compounds for use in the present invention are referred to as "Lipid-conjugates." In one embodiment, compounds for use in the present invention are described by the general formula:

[phosphatidylethanolamine-Y]$n$-X

[phosphatidylserine-Y]$n$-X

[phosphatidylcholine-Y]$n$-X

[phosphatidylinositol-Y]$n$-X

[phosphatidylglycerol-Y]$n$-X

[phosphatidic acid-Y]$n$-X

[lyso-phospholipid-Y]$n$-X

[diacyl-glycerol-Y]$n$-X

[monoacyl-glycerol-Y]$n$-X

[sphingomyelin-Y]$n$-X

[sphingosine-Y]$n$-X

[ceramide-Y]$n$-X wherein
Y is either nothing or a spacer group ranging in length from 2 to 30 atoms; and
X is a physiologically acceptable monomer, dimer, oligomer or polymer; and
n is the number of lipid molecules bound to a molecule of X, wherein n is a number from 1 to 1000 or a number from 2 to 1000.

In one embodiment, the invention provides low-molecular weight Lipid-conjugates, which possess pharmacological activity, which are characterized by the general formula described hereinabove.

In one embodiment of the invention, the physiologically acceptable monomer is salicylate. In another embodiment, the physiologically acceptable monomer is salicylic acid. In another embodiment, the physiologically acceptable monomer is acetyl salicylic acid. In another embodiment, the physiologically acceptable monomer is aspirin. In another embodiment, the physiologically acceptable monomer is a monosaccharide. In another embodiment, the physiologically acceptable monomer is lactobionic acid. In another embodiment, the physiologically acceptable monomer is glucoronic acid. In another embodiment, the physiologically acceptable monomer is maltose. In another embodiment, the physiologically acceptable monomer is an amino acid. In another embodiment, the physiologically acceptable monomer is glycine. In another embodiment, the physiologically acceptable monomer is a carboxylic acid. In another embodiment, the physiologically acceptable monomer is an acetic acid. In another embodiment, the physiologically acceptable monomer is a butyric acid. In another embodiment, the physiologically acceptable monomer is a dicarboxylic acid. In another embodiment, the physiologically acceptable monomer is a fatty acid. In another embodiment, the physiologically acceptable monomer is a dicarboxylic fatty acid. In another embodiment, the physiologically acceptable monomer is a glutaric acid. In another embodiment, the physiologically acceptable monomer is succinic acid. In another embodiment, the physiologically acceptable monomer is dodecanoic acid. In another embodiment, the physiologically acceptable monomer is didodecanoic acid. In another embodiment, the physiologically acceptable monomer is bile acid. In another embodiment, the physiologically acceptable monomer is cholic acid. In another embodiment, the physiologically acceptable monomer is cholesterylhemisuccinate.

In one embodiment of the invention, the physiologically acceptable dimer or oligomer is a dipeptide. In another embodiment, the physiologically acceptable dimer or oligomer is a disaccharide. In another embodiment, the physiologically acceptable dimer or oligomer is a trisaccharide. In another embodiment, the physiologically acceptable dimer or oligomer is an oligosaccharide. In another embodiment, the physiologically acceptable dimer or oligomer is an oligopeptide. In another embodiment, the physiologically acceptable dimer or oligomer is a glycoprotein mixture. In another embodiment, the physiologically acceptable dimer or oligomer is a di- or trisaccharide monomer unit of a polysaccharide. In another embodiment, the physiologically acceptable dimer or oligomer is a di- or trisaccharide monomer unit of a polypyranose. In another embodiment, the physiologically acceptable dimer or oligomer is a di- or trisaccharide monomer unit of a glycosaminogylcan. In another embodiment, the physiologically acceptable dimer or oligomer is a di- or trisaccharide monomer unit of a hyaluronic acid. In another embodiment, the physiologically acceptable dimer or oligomer is a di- or trisaccharide monomer unit of a heparin. In another embodiment, the physiologically acceptable dimer or oligomer is a di- or trisaccharide monomer unit of a heparan sulfate. In another embodiment, the physiologically acceptable dimer or oligomer is a di- or trisaccharide monomer unit of a keratin. In another embodiment, the physiologically acceptable dimer or oligomer is a di- or trisaccharide monomer unit of a keratan sulfate. In another embodiment, the physiologically acceptable dimer or oligomer is a di- or trisaccharide monomer unit of a chondroitin. In another embodiment, the chondroitin is chondoitin sulfate. In another embodiment, the chondroitin is chondoitin-4-sulfate. In another embodiment, the chondroitin is chondoitin-6-sulfate. In another embodiment, the physiologically acceptable dimer or oligomer is a di- or trisaccharide monomer unit of a dermatin. In another embodiment, the physiologically acceptable dimer or oligomer is a di- or trisaccharide monomer unit of a dermatan sulfate. In another embodiment, the physiologically acceptable dimer or oligomer is dextran. In another embodiment, the physiologically acceptable dimer or oligomer is polygeline ('Haemaccel'). In another embodiment, the physiologically acceptable dimer or oligomer is alginate, In another embodiment, the physiologically acceptable dimer or oligomer is hydroxyethyl starch (Hetastarch). In another embodiment, the physiologically acceptable dimer or oligomer is ethylene glycol. In another embodiment, the physiologically acceptable dimer or oligomer is carboxylated ethylene glycol.

In one embodiment, the physiologically acceptable polymer is a polysaccharide. In another embodiment, the physiologically acceptable polymer is a homo-polysaccharide. In another embodiment, the physiologically acceptable polymer is a hetero-polysaccharide. In another embodiment, the physiologically acceptable polymer is a polypyranose. In another embodiment of the invention, the physiologically acceptable polymer is a glycosaminoglycan. In another embodiment, the physiologically acceptable polymer is hyaluronic acid. In another embodiment, the physiologically acceptable polymer is heparin. In another embodiment, the physiologically acceptable polymer is heparan sulfate. In another embodiment, the physiologically acceptable polymer is chondroitin. In another embodiment, the chondroitin is chondoitin-4-sulfate. In another embodiment, the chondroitin is chondoitin-6-sulfate. In another embodiment, the physiologically acceptable polymer is keratin. In another embodiment, the physiologically acceptable polymer is keratan sulfate. In another embodiment, the physiologically acceptable polymer is dermatin. In another embodiment, the physiologically acceptable polymer is dermatan sulfate. In another embodiment, the physiologically acceptable polymer is carboxymethylcellulose. In another embodiment, the physiologically acceptable polymer is dextran. In another embodiment, the physiologically acceptable polymer is polygeline ('Haemaccel'). In another embodiment, the physiologically acceptable polymer is alginate. In another embodiment, the physiologically acceptable polymer is hydroxyethyl starch ('Hetastarch'). In another embodiment, the physiologically acceptable polymer is polyethylene glycol. In another embodiment, the physiologically acceptable polymer is polycarboxylated polyethylene glycol. In another embodiment, the physiologically acceptable polymer is a peptide. In another embodiment, the physiologically acceptable polymer is an oligopeptide. In another embodiment, the physiologically acceptable polymer is a polyglycan. In another embodiment, the physiologically acceptable polymer is a protein. In another embodiment, the physiologically acceptable polymer is a glycoprotein mixture.

In one embodiment, examples of polymers which can be employed as the conjugated moiety for producing Lipid-conjugates for use in the methods of this invention may be physiologically acceptable polymers, including water-dispersible or -soluble polymers of various molecular weights and diverse chemical types, mainly natural and synthetic polymers, such as glycosaminoglycans as described hereinabove, plasma expanders, including polygeline ("Haemaccel", degraded gelatin polypeptide cross-linked via urea bridges, produced by "Behring"), "hydroxyethylstarch" (Hetastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g. polyethyleneglycols, polycarboxyethyleneglycols, polycarboxylated polyethyleneglycols), polyvinnylpyrrolidones, polysaccharides, polypyranoses, alginates, assimilable gums (e.g., xanthan gum), peptides, injectable blood proteins (e.g., serum albumin), cyclodextrin, and derivatives thereof.

In one embodiment of the invention, the lipid or phospholipid moiety is phosphatidic acid. In another embodiment, lipid or phospholipid moiety is an acyl glycerol. In another embodiment, lipid or phospholipid moiety is monoacylglycerol. In another embodiment, lipid or phospholipid moiety is diacylglycerol. In another embodiment, lipid or phospholipid moiety is triacylglycerol. In another embodiment, lipid or phospholipid moiety is sphingosine. In another embodiment, lipid or phospholipid moiety is sphingomyelin. In another embodiment, lipid or phospholipid moiety is ceramide. In another embodiment, lipid or phospholipid moiety is phosphatidylethanolamine. In another embodiment, lipid or phospholipid moiety is phosphatidylserine. In another embodiment, lipid or phospholipid moiety is phosphatidylcholine. In another embodiment, lipid or phospholipid moiety is phosphatidylinositol. In another embodiment, lipid or phospholipid moiety is phosphatidylglycerol. In another embodiment, lipid or phospholipid moiety is an ether or alkyl phospholipid derivative thereof.

In one embodiment, the set of compounds comprising phosphatidylethanolamine covalently bound to a physiologically acceptable monomer, dimmer, oligomer, or polymer, is referred to herein as the PE-conjugates. In one embodiment, the phosphatidylethanolamine moiety is dipalmitoyl phosphatidylethanolamine. In another embodiment, the phosphatidylethanolamine moiety is dimyristoyl phosphatidylethanolamine. In another embodiment, related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the biological experiments described below for the Lipid-conjugates and the structural similarities shared by these compounds.

As defined by the structural formulae provided herein for the Lipid-conjugates or phospholipids-conjugates, these compounds may contain between one to one thousand lipid or phospholipid moieties bound to a single physiologically acceptable polymer molecule. In one embodiment of this invention, n is a number from 1 to 1000. In another embodiment, n is a number from 2 to 500. In another embodiment, n is a number from 1 to 500. In another embodiment, n is a number from 1 to 100. In another embodiment, n is a number from 2 to 1000. In another embodiment, n is a number from 2 to 100. In another embodiment, n is a number from 2 to 200. In another embodiment, n is a number from 3 to 300. In another embodiment, n is a number from 10 to 400. In another embodiment, n is a number from 50 to 500. In another embodiment, n is a number from 100 to 300. In another embodiment, n is a number from 300 to 500. In another embodiment, n is a number from 500 to 800. In another embodiment, n is a number from 500 to 1000.

In one embodiment of the invention, when the conjugated moiety is a polymer, the ratio of lipid moieties covalently bound may range from one to one thousand lipid or phospholipids (PL) residues per polymer molecule, depending upon the nature of the polymer and the reaction conditions employed. For example, the relative quantities of the starting materials, or the extent of the reaction time, may be modified in order to obtain Lipid-conjugate or Phospholipid (PL)-conjugate products with either high or low ratios of lipid residues per polymer, as desired.

In the methods, according to embodiments of the invention, the Lipid-conjugates or Phospholipid-conjugate administered to a subject are comprised of at least one lipid or phospholipid moiety covalently bound through an atom of the polar head group to a monomeric or polymeric moiety (referred to herein as the conjugated moiety) of either low or high molecular weight. In one embodiment, the conjugated moiety is conjugated to the lipid, phospholipid, or spacer via an ester bond. In another embodiment, the conjugated moiety is conjugated to the lipid, phospholipid, or spacer via an amide bond.

When desired, an optional bridging moiety can be used to link the lipid or phospholipid moiety to the monomer or polymeric moiety. The composition of some phospholipid-conjugates of high molecular weight, and associated analogues, are the subject of U.S. Pat. No. 5,064,817, which is incorporated herein in its entirety by reference.

In one embodiment, the term "moiety" means a chemical entity otherwise corresponding to a chemical compound, which has a valence satisfied by a covalent bond.

In some cases, according to embodiments of the invention, the monomer or polymer chosen for preparation of the Lipid-conjugate or Phospholipid-conjugate may in itself have selected biological properties. For example, both heparin and hyaluronic acid are materials with known physiological functions. In the present invention, however, the Lipid-conjugates or Phospholipid-conjugate formed from these substances as starting materials display a new and wider set of pharmaceutical activities than would be predicted from administration of either heparin or hyaluronic acid which have not been bound by covalent linkage to a phospholipid. It can be shown, by standard comparative experiments that phosphatidylethanolamine (PE) linked to hyaluronic acid (Compound XXII), to heparin (Compound XXIV), to chondroitin sulfate A (Compound XXV), to carboxymethylcellulose (Compound XXVI), to Polygeline (haemaccel) (Compound XXVII), or to hydroxyethylstarch (Compound XXVIII), are far superior in terms of potency and range of useful pharmaceutical activity to the free conjugates (the polymers above and the like). In fact, these latter substances are, in general, not considered useful in methods for inhibiting angiogenesis or inhibiting the development of atherosclerosis. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone. In the cases described herein, the diversity of biological activities and the effectiveness in disease exhibited by the compounds far exceed the properties anticipated by use of the starting materials themselves, when administered alone or in combination.

The biologically active Lipid-conjugates or Phospholipid-conjugates described herein can have a wide range of molecular weights, e.g., above 50,000 (up to a few hundred thousands) when it is desirable to retain the conjugates in the vascular system and below 50,000 when targeting to extravascular systems is desirable. The sole limitation on the molecular weight and the chemical structure of the conjugated moiety is that it does not result in a Lipid-conjugate or Phospholipid-conjugate devoid of the desired biological activity, or lead to chemical or physiological instability to the extent that the Lipid-conjugate or Phospholipid-conjugate is rendered useless as a drug in the method of use described herein.

In one embodiment, the compound for use in the present invention is represented by the structure of the general formula (A):

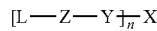

(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a physiologically acceptable monomer, dimer, oligomer, or polymer; and
n is a number from 1 to 1000 or a number from 2 to 1000;
wherein any bond between L, Z, Y and X is either an amide or an esoteric bond.

In one embodiment, L of Compound A is phospholipids (PL). In another embodiment, L of Compound A is a lipid.

In one embodiment, L is phosphatidyl, Z is ethanolamine, wherein L and Z are chemically bonded resulting in phosphatidylethanolamine, Y is nothing, and X is carboxymethylcellulose. In another embodiment, L is phosphatidyl, Z is ethanolamine, wherein L and Z are chemically bonded resulting in phosphatidylethanolamine, Y is nothing, and X is a glycosaminoglycan. In one embodiment, the phosphatidylethanolamine moiety is dipalmitoyl phosphatidylethanolamine. In another embodiment, the phosphatidylethanolamine moiety is dimyristoyl phosphatidylethanolamine. In another embodiment, the phosphatidylethanolamine moiety is 1-Acyl-2-Acyl-sn-Glycero-3-Phosphoethanolamine. In another embodiment, the phosphatidylethanolamine moiety is 1,2-Diacyl-sn-Glycero-3-Phosphoethanolamine. In another embodiment, the phosphatidylethanolamine moiety is 1-hexadecanoyl-2-[(Z)-octadec-9-enoyl]-sn-glycero-3-phospho}ethanolamine. In another embodiment, the phosphatidylethanolamine moiety is 1,2-distearoylphosphatidylethanolamine. In another embodiment, the phosphatidylethanolamine moiety is 1,2-distearoylphosphatidylethanolamine zwitterions. In another embodiment, the phosphatidylethanolamine moiety is 1,2-distearoylphosphatidylethanolaminium. In another embodiment, the phosphatidylethanolamine moiety is phosphatidyldi-N-methylethanolamines. In another embodiment, the phosphatidylethanolamine moiety is phosphatidyl-N-methylethanolamines.

In another embodiment, the phosphatidylethanolamine moiety is a transesterified phosphatidylethanolamine. In another embodiment, the phosphatidylethanolamine moiety is dipalmitoyl phosphatidylethanolamine. In another embodiment, the phosphatidylethanolamine moiety is palmitoyl oleoyl phosphatidylethanolamine. In another embodiment, the phosphatidylethanolamine moiety is dioleoyl phosphatidylethanolamine. In another embodiment, the phosphatidylethanolamine moiety is a PE conjugated to a moiety selected from the group comprising of dicarboxylic acids, polyethylene glycols, polyalkyl ethers and gangliosides.

In another embodiment, the phosphatidylethanolamine moiety is a synthetic analogs of phosphatidylethanolamine, In another embodiment, the phosphatidylethanolamine moiety is isolated from natural sources. In another embodiment, the phosphatidylethanolamine moiety is synthesized according to established chemical procedures, or enzymatically synthesized using the corresponding phosphatidyl choline compound in the presence of ethanolamine and phospholipase D.

In another embodiment, the compound for use in the present invention is represented by the structure of the general formula (I):

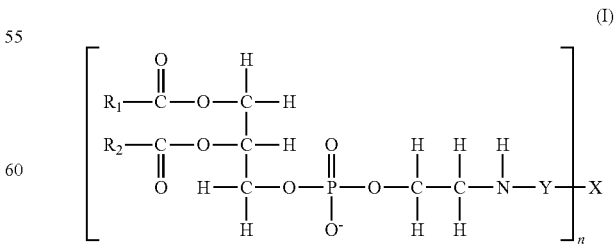

(I)

wherein
$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is either a physiologically acceptable monomer, dimer, oligomer or a physiologically acceptable polymer; and
n is a number from 1 to 1,000 or 2 to 1000;
wherein if Y is nothing the phosphatidylethanolamine is directly linked to X via an amide bond and if Y is a spacer, the spacer is directly linked to X via an amide or an esoteric bond and to the phosphatidylethanolamine via an amide bond.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. In one embodiment, the PE moiety is dipalmitoyl-phosphatidyl-ethanolamine. In another embodiment, the PE moiety is dimyristoyl-phosphatidyl-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the compound for use in the present invention is represented by the structure of the general formula (II):

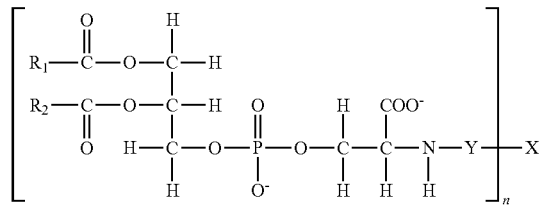

(II)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a physiologically acceptable monomer, dimer, oligomer or polymer wherein X is a glycosaminoglycan; and
n is a number from 1 to 1000 or a number from 2 to 1000;
wherein if Y is nothing, the phosphatidylserine is directly linked to X via an amide bond and if Y is a spacer, the spacer is directly linked to X via an amide or an esoteric bond and to the phosphatidylserine via an amide bond.

In one embodiment, the phosphatidylserine may be bonded to Y, or to X if Y is nothing, via the COO⁻ moiety of the phosphatidylserine.

In another embodiment, the compound for use in the present invention is represented by the structure of the general formula (III):

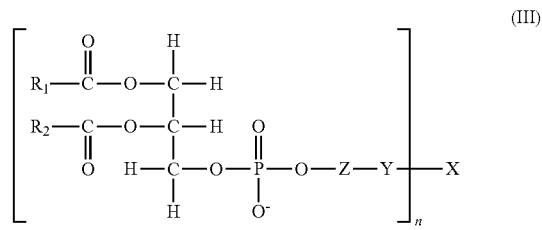

(III)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer wherein X is a glycosaminoglycan; and
n is a number from 1 to 1000 or a number from 2 to 1000;
wherein any bond between the phosphatidyl, Z, Y and X is either an amide or an esoteric bond.

In another embodiment, the compound for use in the present invention is represented by the structure of the general formula (IV):

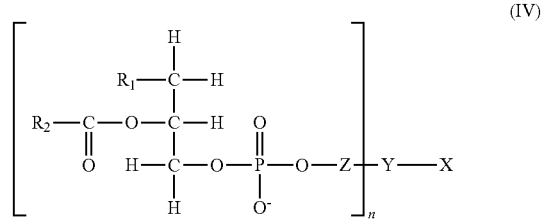

(IV)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, ethanolamine, serine or glycerol;
Y is either nothing or a spacer group ranging in length from 2 to 30 atoms;
X is a physiologically acceptable monomer, dimer, oligomer, or polymer wherein X is a glycosaminoglycan; and
n is a number from 1 to 1000 or a number from 2 to 1000;
wherein any bond between the phospholipid, Z, Y and X is either an amide or an esoteric bond.

In another embodiment, the compound for use in the present invention is represented by the structure of the general formula (V):

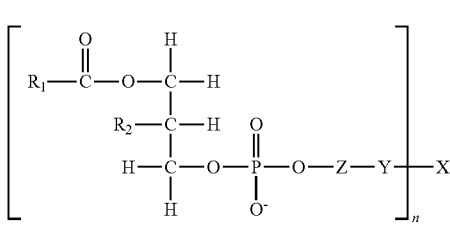

(V)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, ethanolamine, serine or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the phospholipid, Z, Y and X is either an amide or an esoteric bond.

In another embodiment, the compound for use in the present invention is represented by the structure of the general formula (VI):

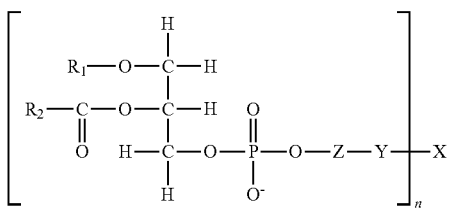

(VI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, ethanolamine, serine or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the phospholipid, Z, Y and X is either an amide or an esoteric bond.

In another embodiment, the compound for use in the present invention is represented by the structure of the general formula (VII):

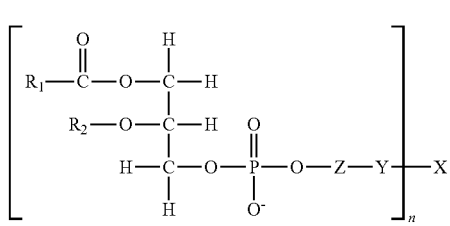

(VII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, ethanolamine, serine, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the phospholipid, Z, Y and X is either an amide or an esoteric bond.

In one embodiment of the invention, the conjugate comprises phosphatidylcholine (PC), phosphatidylinositol (PI), phosphatidic acid (PA), wherein Z is nothing, and phosphatidylglycerol (PG) as defined as compounds of the general formula (III).

In another embodiment, the compound for use in the present invention is represented by the structure of the general formula (VIII):

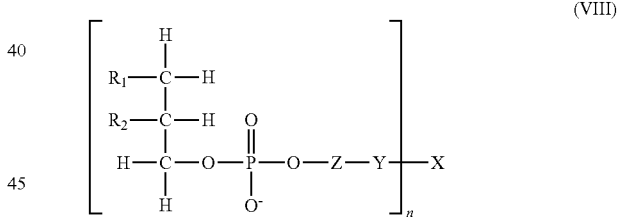

(VIII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the phospholipid, Z, Y and X is either an amide or an esoteric bond.

In another embodiment, the compound for use in the present invention is represented by the structure of the general formula (IX):

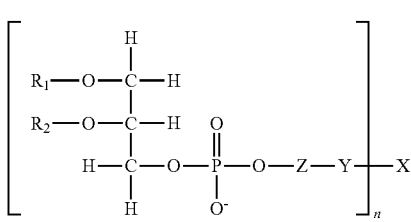

(IX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the phospholipid, Z, Y and X is either an amide or an esoteric bond.

In another embodiment, the compound for use in the present invention is represented by the structure of the general formula (IXa):

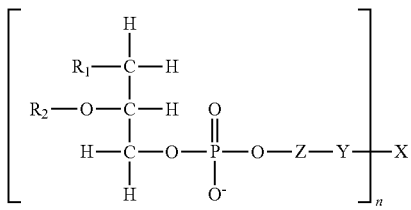

(IXa)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the phospholipid, Z, Y and X is either an amide or an esoteric bond.

In another embodiment, the compound for use in the present invention is represented by the structure of the general formula (IXb):

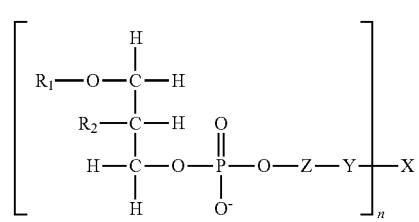

(IXb)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the phospholipid, Z, Y and X is either an amide or an esoteric bond.

In another embodiment, the compound for use in the present invention is represented by the structure of the general formula (X):

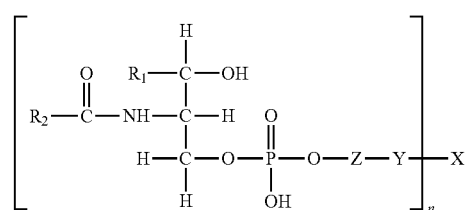

(X)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the ceramide phosphoryl, Z, Y and X is either an amide or an esteric bond.

In another embodiment, the compound for use in the present invention is represented by the structure of the general formula (Xa):

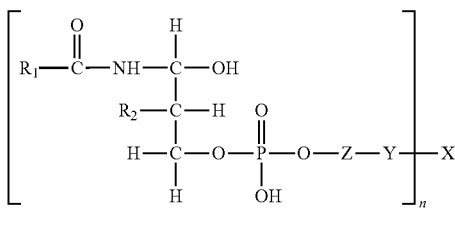

(XI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000 or a number from 2 to 1000;

wherein any bond between the ceramide phosphoryl, Z, Y and X is either an amide or an esteric bond.

In another embodiment, the compound for use in the present invention is represented by the structure of the general formula (XI):

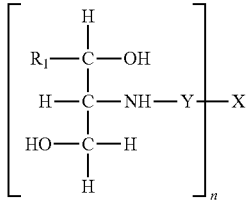

(XI)

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein if Y is nothing the sphingosyl is directly linked to X via an amide bond and if Y is a spacer, the spacer is directly linked to X and to the sphingosyl via an amide bond and to X via an amide or an esoteric bond.

In another embodiment, the compound for use in the present invention is represented by the structure of the general formula (XII):

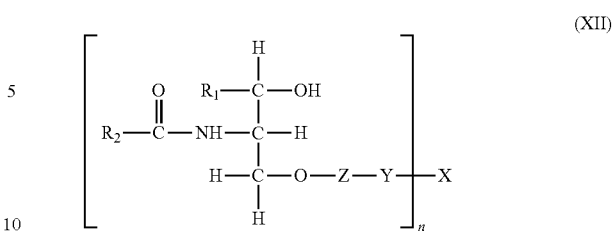

(XII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, phosphate, inositol, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 001000;

wherein any bond between the ceramide, Z, Y and X is either an amide or an esoteric bond.

In another embodiment, the compound for use in the present invention is represented by the structure of the general formula (XIIa):

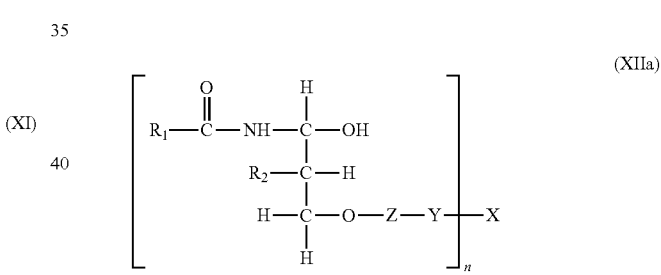

(XIIa)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, phosphate, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 001000;

wherein any bond between the ceramide, Z, Y and X is either an amide or an esoteric bond.

In another embodiment, the compound for use in the present invention is represented by the structure of the general formula (XIII):

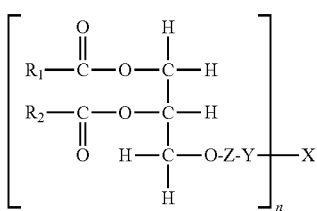

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, ethanolamine, serine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the diglyceryl, Z, Y and X is either an amide or an esoteric bond.

In another embodiment, the compound for use in the present invention is represented by the structure of the general formula (XIV):

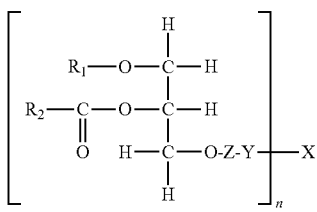

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, ethanolamine, serine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the glycerolipid, Z, Y and X is either an amide or an esoteric bond.

In another embodiment, the compound for use in the present invention is represented by the structure of the general formula (XV):

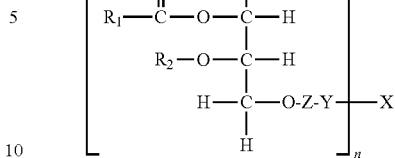

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, ethanolamine, serine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the glycerolipid, Z, Y and X is either an amide or an esoteric bond.

In another embodiment, the compound for use in the present invention is represented by the structure of the general formula (XVI):

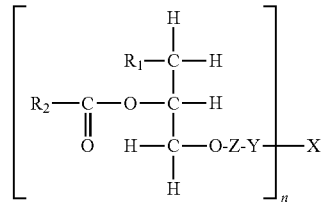

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, ethanolamine, serine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the lipid, Z, Y and X is either an amide or an esoteric bond.

In another embodiment, the compound for use in the present invention is represented by the structure of the general formula (XVII):

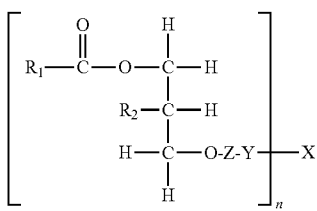
(XVII)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, ethanolamine, serine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the lipid, Z, Y and X is either an amide or an esoteric bond.

In another embodiment, the compound for use in the present invention is represented by the structure of the general formula (XVIII):

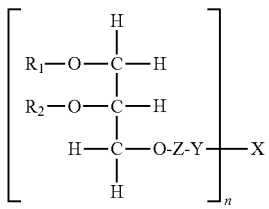
(XVIII)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, ethanolamine, serine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the lipid, Z, Y and X is either an amide or an esoteric bond.

In another embodiment, the compound for use in the present invention is represented by the structure of the general formula (XIX):

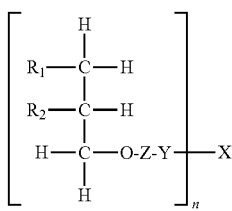
(XIX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, ethanolamine, seine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the lipid, Z, Y and X is either an amide or an esoteric bond.

In another embodiment, the compound for use in the present invention is represented by the structure of the general formula (XX):

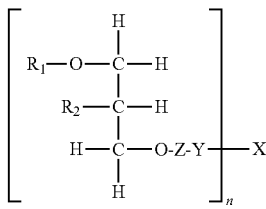
(XX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, ethanoleamine, serine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the lipid, Z, Y and X is either an amide or an esoteric bond.

In another embodiment, the compound for use in the present invention is represented by the structure of the general formula (XXI):

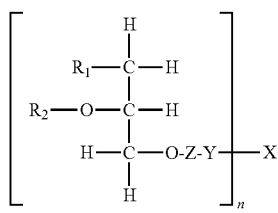

(XXI)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, ethanolamine, serine, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000 or a number from 2 to 1000;

wherein any bond between the lipid, Z, Y and X is either an amide or an esoteric bond.

For any or all of the compounds represented by the structures of the general formulae (A), (I), (II), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX), (XXI), and (XXII) hereinabove: In one embodiment, X is a glycosaminoglycan. According to this aspect and in one embodiment, the glycosaminoglycan may be, inter alia, hyaluronic acid, heparin, heparan sulfate, chondroitin sulfate, keratin, keratan sulfate, dermatan sulfate or a derivative thereof. In one embodiment, the chondroitin sulfate may be, inter alia, chondroitin-6-sulfate, chondroitin-4-sulfate or a derivative thereof. In another embodiment, X is not a glycosaminoglycan. In another embodiment, X is a polysaccharide, which in one embodiment is a hetero-polysaccharide, and in another embodiment, is a homo-polysaccharide. In another embodiment, X is a polypyranose.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In one embodiment of the invention, Y is nothing. Non-limiting examples of suitable divalent groups forming the optional bridging group (which in one embodiment, is referred to as a spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NH, CO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$—)$_n$— wherein x is an integer of 1 or more.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, the structure of the lipid or phospholipid in any compound according to the invention is intact. In another embodiment, the natural structure of the lipid or phospholipids in any compound according to the invention is maintained.

In some embodiments, the compounds (A), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX) and (XXI) as presented hereinabove comprises a Z group. In one embodiment, Z is a nothing. In another embodiment Z is inositol. In another embodiment, Z is choline. In another embodiment, Z is glycerol.

In some embodiments, the compounds (XII), (XIIa), (XIII), (XIV), (XV), (XVI), (XVII), (XVIII), (XIX), (XX) and (XXI) as presented hereinabove comprises a Z group. In one embodiment, the Z is a phosphate. In another embodiment, the phosphate is phoso-ethanolamine —P(OH)(=O)—O—CH$_2$CH$_2$—NH—. In another embodiment, the phosphate is phospho-serine-P(OH)(=O)—O—CH$_2$CH(COOH)—NH—.

In one embodiment, compounds (A), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX) and (XXI) for use in the methods of the invention comprise one of the following as the conjugated moiety X. In another embodiment X is acetate, butyrate, glutarate, succinate, dodecanoate, didodecanoate, maltose, lactobionic acid, dextran, alginate, aspirin, cholate, cholesterylhemisuccinate, carboxymethyl-cellulose, heparin, hyaluronic acid, chondroitin sulfate, polygeline (haemaccel), polyethyleneglycol, polycarboxylated polyethylene glycol, a glycosaminoglycan, a polysaccharide, a hetero-polysaccharide, a homo-polysaccharide, or a polypyranose.

The polymers used as starting material to prepare the lipids or PL-conjugates may vary in molecular weight from 1 to 2,000 kDa.

In another embodiment, the phospholipid (PL)-conjugate compound of this invention is a phosphatidylethanolamine, a phosphatidylserine, a phosphatidylcholine, a phosphatidylinositol, a phosphatidic acid or a phosphatidylglycerol. In another embodiment, PL comprises the residue of palmitic acid, myristic acid, myristoleic acid, palmitoleic acid, oleic acid, linoleic acid, linolenic acid, arachidonic acid, eicosapentaenoic acid, erucic acid or docosahexaenoic acid. In another embodiment, PL is dimyristoyl phosphatidylethanolamine.

In another embodiment, PL is dipalmitoyl phosphatidylethanolamine. Phosphatidylserine (PS) and its analogues, such as palmitoyl-stearoyl-PS, natural PS from various sources, semisynthetic PSs, synthetic, natural and artificial PSs and their isomers.

In one embodiment, the compounds of this invention comprise lipid conjugates. In another embodiment, the lipid is lysophospholipids, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group. The PS can bind also via the COOH group.

In one embodiment, the lipid and PL are conjugated to glycosaminoglycan (GAG). In another embodiment, the GAG is hyaluronic acid, heparin, heparan sulfate, chondroitin, chondroitin sulfate, dermatan sulfate or keratan sulfate. In another embodiment, GAG is hyaluronic acid. In another embodiment, GAG is heparin. In another embodiment, GAG is chondroitin. In another embodiment, GAG is chondroitin sulfate. In another embodiment, GAG is dermatan sulfate, in another embodiment, GAG is keratan sulfate.

In another embodiment, chondroitin sulfate is chondroitin-6-sulfate, chondroitin-4-sulfate or a derivative thereof. In another embodiment, dermatan sulfate is dermatan-6-sulfate, dermatan-4-sulfate or a derivative thereof.

In one embodiment, the compounds for use in the present invention are biodegradable.

In one embodiment, the compound according to the invention is phosphatidylethanolamine bound to aspirin. In one embodiment, the compound according to the invention is phosphatidylethanolamine bound to glutarate.

In some embodiments, the compounds for use are as listed in Table 1 below.

TABLE 1

| Phospholipid | Spacer | Polymer (m.w.) | Compound |
| --- | --- | --- | --- |
| PE | None | Hyaluronic acid (2-2000 kDa) | XXII |
| Dimyristoyl-PE | None | Hyaluronic acid | XXIII |
| PE | None | Heparin (0.5-110 kDa) | XXIV |
| PE | None | Chondroitin sulfate A | XXV |
| PE | None | Carboxymethylcellulose (20-500 kDa) | XXVI |
| PE | Dicarboxylic acid + Diamine | Polygeline (haemaccel) (4-40 kDa) | XXVII |
| PE | None | Hydroxyethylstarch | XXVIII |
| PE | Dicarboxylic acid + Diamine | Dextran (1-2,000 kDa) | XXIX |
| PE | None | Aspirin | XXX |
| PE | Carboxyl amino group | Hyaluronic acid (2-2000 kDa) | XXXI |
| PE | Dicarboxyl group | Hyaluronic acid (2-2000 kDa) | XXXII |
| PE | Dipalmitoic acid | Hyaluronic acid (2-2000 kDa) | XXXIII |
| PE | Carboxyl amino group | Heparin (0.5-110 kDa) | XXXIV |
| PE | Dicarboxyl group | Heparin (0.5-110 kDa) | XXXV |
| PE | Carboxyl amino group | Chondroitin sulfate A | XXXVI |
| PE | Dicarboxyl group | Chondroitin sulfate A | XXXVII |
| PE | Carboxyl amino group | Carboxymethylcellulose (20-500 kDa) | XXXVIII |
| PE | Dicarboxyl group | Carboxymethylcellulose (20-500 kDa) | XXXIX |

TABLE 1-continued

| Phospholipid | Spacer | Polymer (m.w.) | Compound |
| --- | --- | --- | --- |
| PE | None | Polygeline (haemaccel) (4-40 kDa) | XL |
| PE | Carboxyl amino group | Polygeline (haemaccel) (4-40 kDa) | XLI |
| PE | Dicarboxyl group | Polygeline (haemaccel) (4-40 kDa) | XLII |
| PE | Carboxyl amino group | Hydroxyethylstarch | XLIII |
| PE | Dicarboxyl group | Hydroxyethylstarch | XLIV |
| PE | None | Dextran (1-2,000 kDa) | XLV |
| PE | Carboxyl amino group | Dextran (1-2,000 kDa) | XLVI |
| PE | Dicarboxyl group | Dextran (1-2,000 kDa) | XLVII |
| PE | Carboxyl amino group | Aspirin | XLVIII |
| PE | Dicarboxyl group | Aspirin | XLIX |
| PE | None | Albumin | L |
| PE | None | Alginate (2-2000 kDa) | LI |
| PE | None | Polyaminoacid | LII |
| PE | None | Polyethylene glycol | LIII |
| PE | None | Lactobionic acid | LIV |
| PE | None | Acetylsalicylate | LV |
| PE | None | Cholesteryl-hemmisuccinate | LVI |
| PE | None | Maltose | LVII |
| PE | None | Cholic acid | LVIII |
| PE | None | Chondroitin sulfates | LIX |
| PE | None | Polycarboxylated polyethylene glycol | LX |
| Dipalmitoyl-PE | None | Hyaluronic acid | LXI |
| Dipalmitoyl-PE | None | Heparin | LXII |
| Dipalmitoyl-PE | None | Chondroitin sulfate A | LXIII |
| Dipalmitoyl-PE | None | Carboxymethylcellulose | LXIV |
| Dipalmitoyl-PE | None | Polygeline (haemaccel) | LXV |
| Dipalmitoyl-PE | None | Hydroxyethylstarch | LXVI |
| Dipalmitoyl-PE | None | Dextran | LXVII |
| Dipalmitoyl-PE | None | Aspirin | LXVIII |
| Dimyristoyl-PE | None | Heparin | LXVIX |
| Dimyristoyl-PE | None | Chondroitin sulfate A | LXX |
| Dimyristoyl-PE | None | Carboxymethylcellulose | LXXI |
| Dimyristoyl-PE | None | Polygeline (haemaccel) | LXXII |
| Dimyristoyl-PE | None | Hydroxyethylstarch | LXXIII |
| Dimyristoyl-PE | None | Dextran | LXXIV |
| Dimyristoyl-PE | None | Aspirin | LXXV |
| PS | None | Hyaluronic acid | LXXVI |
| PS | None | Heparin | LXXVII |
| PS | None | Polygeline (haemaccel) | LXXVIII |
| PC | None | Hyaluronic acid | LXXIX |
| PC | None | Heparin | LXXX |
| PC | None | Polygeline (haemaccel) | LXXXI |
| PI | None | Hyaluronic acid | LXXXII |
| PI | None | Heparin | LXXXIII |
| PI | None | Polygeline (haemaccel) | LXXXIV |
| PG | None | Hyaluronic acid | LXXXV |
| PG | None | Heparin | LXXXVI |
| PG | None | Polygeline (haemaccel) | LXXXVII |
| PE | None | Glutaryl | LXXXVIII |

In one embodiment of the invention, the compounds for use in the present invention are any one or more of Compounds I-LXXXVIII. In another embodiment, the compounds for use in the present invention are Compound XXII, Compound XXIII, Compound XXIV, Compound XXV, Compound XXVI, Compound XXVII, Compound XXVIII, Compound XXIX, Compound XXX, or pharmaceutically acceptable salts thereof, in combination with a physiologically acceptable carrier or solvent. According to embodiments of the invention, these polymers, when chosen as the conjugated moiety, may vary in molecular weights from 200 to 2,000,000 Daltons. In one embodiment of the invention, the molecular weight of the polymer as referred to herein is from 200 to 1000 Daltons. In another embodiment, the molecular weight of the polymer as referred to herein is from 200 to 1000 Daltons. In another embodiment, the molecular weight of the polymer as referred to herein is from 1000 to 5000 Daltons. In another embodiment, the molecular weight of the polymer as referred to herein is from 5000 to 10,000 Daltons. In another embodiment, the molecular weight of the polymer as referred to herein is from 10,000 to 20,000 Daltons. In another embodiment, the molecular weight of the polymer as referred to herein is from 10,000 to 50,000 Daltons. In another embodiment, the molecular weight of the polymer as referred to herein is from 20,000 to 70,000 Daltons. In another embodiment, the molecular weight of the polymer as referred to herein is from 50,000 to 100,000 Daltons. In another embodiment, the molecular weight of the polymer as referred to herein is from 100,000 to 200,000 Daltons. In another embodiment, the molecular weight of the polymer as referred to herein is from 200,000 to 500,000 Daltons. In another embodiment, the molecular weight of the polymer as referred to herein is from 200,000 to 1,000,000 Daltons. In another embodiment, the molecular weight of the polymer as referred to herein is from 500,000 to 1,000,000 Daltons. In another embodiment, the molecular weight of the polymer as referred to herein is from 1,000,000 to 2,000,000 Daltons. Various molecular weight species have been shown to have the desired biological efficacy Examples of suitable divalent groups forming the optional bridging group Y are straight- or branched chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. In one embodiment of the invention, the alkyl phospholipid derivatives and ether phospholipid derivatives are exemplified herein. In one embodiment, these derivatives are exemplified hereinabove by the general formulae (VIII) and (IX).

In one embodiment of the invention, X is covalently conjugated to a lipid. In another embodiment, X is covalently conjugated to a lipid via an amide bond. In another embodiment, X is covalently conjugated to a lipid via an esoteric bond. In another embodiment, the lipid is phosphatidylethanolamine.

In one embodiment, cell surface GAGs play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAGs protect cells from bacterial, viral and parasitic infection, and their stripping exposes the cell to interaction and subsequent internalization of the microorganism. Enrichment of cell surface GAGs would thus assist in protection of the cell from injurious processes. Thus, in one embodiment of the invention, PLA2 inhibitors are conjugated to GAGs or GAG-mimicking molecules. In another embodiment, these Lipid-conjugates provide wide-range protection from diverse injurious processes, and ameliorate diseases that require cell protection from injurious biochemical mediators.

In another embodiment, a GAG-mimicking molecule may be, inter alia, a negatively charged molecule. In another embodiment, a GAG-mimicking molecule may be, inter alia, a salicylate derivative. In another embodiment, a GAG-mimicking molecule may be, inter alia, a dicarboxylic acid.

In another embodiment, a composition as described herein further comprises zinc oxide, Vitamins A, D, E, and K, an antibacterial agent, or any combination thereof. In another embodiment, an antibacterial agent as described herein is a bismuth-containing compound, sulfonamides, nitrofurans, metronidazole, nimorazole, tinidazole, benzoic acid, aminoglycosides, macrolides, penicillins, polypeptides, tetracyclines, cephalosporins, chloramphenicol, clindamycin and mixtures thereof. In more preferred embodiments, the antibacterial agents are selected from the group consisting of bismuth aluminate, bismuth subcitrate, bismuth subgalate, bismuth subsalicylate, sulfonamides, nitrofurazone, nitrofurantoin, furazolidone, metronidazole, tinidazole, nimorazole, benzoic acid, hentamycin, neomycin, kynamycin, streptomycin, erythromycin, clindamycin, rifampin, rifamycin, penicillin G, penicillin V, ampicillin, amoxicillin, bacitracin, polymyxin, tetracycline, chlortetracycline, oxytetracycline, doxycycline, cephalexin, cephalothin, clindamycin, chloramphenical and mixtures thereof.

In another embodiment, the antibacterial agent is selected from a wide range of therapeutic agents and mixtures of therapeutic agents which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillins, polypeptides, tetracyclines, cephalosporins, chloramphenicol, and clindamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furozolidone; and miscellaneous antibacterials such as metrotidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bactracin and polymyxin; the tetracyclines, such as chlorotetracycline, oxytetracycline, and doxycycline; the cephalospoins, suck as cephalexin and cephalothin; and miscellaneous antibiotics, such as chloramphenicol, and clindamycin. More preferably, the antibacterial agent is selected from the group consisting of bismuth aluminate, nitrofurantoin, furozolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline, chlorotetracycline, oxytetracycline, doxycycline, cephalexin, cephalothin, chloramphenicol, and clidamycin.

In another embodiment, the antifungal agent is astemizole, clotrimazole, omeprazole, econazole, oxiconazole, sulconazole, fluconazole, ketoconazole, itraconazole, torbinafine, and mixtures thereof. In another embodiment, a composition as described herein comprises a calcium channel blocker.

In another embodiment, the invention provides a pharmaceutical composition comprising a lipid or phospholipid moiety bonded to a physiologically acceptable monomer, dimer, oligomer, or polymer; and a pharmaceutically acceptable carrier or excipient. In another embodiment, the invention provides a pharmaceutical composition comprising a conjugate as described for treating a subject afflicted with a tumor. In another embodiment, the invention provides a pharmaceutical composition comprising a conjugate as described for treating a subject in risk of developing a tumor. In another embodiment, the invention provides a pharmaceutical composition comprising a conjugate as described for inhibiting angiogenesis in a subject in need thereof. In another embodiment, the invention provides a pharmaceutical composition comprising a conjugate as described for treating a subject afflicted with atherosclerosis. In another embodiment, a pharmaceutical composition comprising a conjugate as described is effective in inhibiting blood vessels formation. In another embodiment, a pharmaceutical composition comprising a conjugate as described is effective in inhibiting endothelial cell migration. In another embodiment, a pharmaceutical composition comprising a conjugate as described counteracts the effect of pro-angiogenic agents.

In another embodiment, the invention provides a pharmaceutical composition comprising a combination of active pharmaceutical ingredients comprising a lipid or phospholipid moiety bonded to a physiologically acceptable monomer, dimer, oligomer, or polymer; and an anti-cancer agent. In another embodiment, the invention provides a pharmaceutical composition comprising a combination of active pharmaceutical ingredients comprising a lipid or phospholipid moiety bonded to a physiologically acceptable monomer, dimer, oligomer, or polymer; and a an anti-tumor agent. In another embodiment, the invention provides a pharmaceutical composition comprising a combination of active pharmaceutical ingredients comprising a lipid or phospholipid moiety bonded to a physiologically acceptable monomer, dimer, oligomer, or polymer; and a cardiovascular therapeutic agent.

In another embodiment, the invention provides a pharmaceutical composition for treating a subject afflicted with cancer characterized by tumors or afflicted with atherosclerosis, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (Xa) (XI), (XII), (XIIa), (XIII), (XIV), (XV), (XVI), (XVII), (XVIII), (XIX), (XX), (XXI), (XXII), or any combination thereof.

Preparation of Compounds for Use in the Present Invention

In one embodiment, the preparation of high molecular weight Lipid-conjugates for use in the methods of the present invention is as described in U.S. Pat. No. 5,064,817, which is incorporated fully herein by reference. In one embodiment, these synthetic methods are applicable to the preparation of Lipid-conjugates as well, i.e. Lipid-conjugates comprising monomers and dimers as the conjugated moiety, with appropriate modifications in the procedure as would be readily evident to one skilled in the art. The preparation of some Lipid-conjugates may be conducted using methods well known in the art or as described in U.S. Provisional Patent Application 60/704,874, which is incorporated herein by reference in its entirety.

Dosages and Routes of Administration

The methods of this invention can be adapted to the use of the therapeutic compositions comprising Lipid-conjugates or Phospholipid-conjugates in admixture with conventional excipients, i.e. pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins, steroids, anti-inflammatory compounds, etc., as will be understood by one skilled in the art.

In one embodiment, the route of administration may be parenteral, enteral, or a combination thereof. In another embodiment, the route may be intra-ocular, conjunctival, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation, nasal aspiration (spray), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, etc.

In another embodiment, the compositions include those suitable for oral, rectal, intravaginal, topical, nasal, ophthalmic or parenteral administration, all of which may be used as routes of administration using the materials of the present invention. Other suitable routes of administration include direct injection onto an arterial surface and intraparenchymal injection directly into targeted areas of an organ or a tumor. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. Methods typically include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the compounds of the invention in liposomes or as a suspension in an aqueous liquid or non-aqueous liquid such as a syrup, an elixir, or an emulsion.

Compositions suitable for parenteral administration conveniently comprise a sterile aqueous preparation of the molecule of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Oral agents provide the advantages of easy administration and chronic systemic treatment. However, local delivery of angiogenesis inhibitors via catheters, gene transfer techniques, and endovascular stents or polymers can be utilized in order to control localized disease.

An exemplary pharmaceutical composition is a therapeutically effective amount of a composition as described herein that will inhibit angiogenesis as shown in a standard assay such as the chick chorioallantoic membrane (CAM) assay (Crum, et al., Science 230: 1375, 1985), which optionally is included in a pharmaceutically-acceptable and compatible carrier.

The term "pharmaceutically-acceptable and compatible carrier" as used herein, includes one or more compatible solid or liquid filler diluents or encapsulating substances that are suitable for administration to a human or other animal. In the present invention, the term "carrier" thus denotes an organic or inorganic ingredient, natural or synthetic, with which the compounds of the invention are combined to facilitate application. The term "therapeutically-effective amount" is that amount of the present pharmaceutical composition which produces a desired result or exerts a desired influence on the particular condition being treated. For example, the amount necessary to inhibit angiogenesis of plaque vessels to provide prophylactic protection or the amount necessary to inhibit angiogenesis surrounding a tumor. Typically when the composition is being used as prophylactic additional doses will be administered at periodic intervals after the initial administration. Various concentrations may be used in preparing compositions incorporating the same ingredient to provide for variations in the age of the patient to be treated, the severity of the condition, the duration of the treatment and the mode of administration.

The term "compatible", as used herein, means that the components of the pharmaceutical compositions are capable of being comingled with a small molecule of the present invention, and with each other, in a manner such that does not substantially impair the desired pharmaceutical efficacy.

Doses of the pharmaceutical compositions of the invention will vary depending on the subject and upon the particular route of administration used. Dosages can range from 0.1 to 100,000 μg/kg per day, more preferably 1 to 10,000 μg/kg. By way of an example only, an overall dose range of from about, for example, 1 microgram to about 300 micrograms might be used for human use. This dose can be delivered at periodic intervals based upon the composition. In another embodiment, compounds might be administered daily. Pharmaceutical compositions of the present invention can also be administered to a subject according to a variety of other, well-characterized protocols. For example, using pulsed therapy.

In general, the doses utilized for the above described purposes will vary, but will be in an effective amount to exert the desired anti-disease effect. As used herein, the term "pharmaceutically effective amount" refers to an amount of a compound of formulae I-XXI which will produce the desired alleviation in symptoms or signs of disease in a patient. The doses utilized for any of the above-described purposes will generally be from 1 to about 1000 milligrams per kilogram of body weight (mg/kg), administered one to four times per day, or by continuous IV infusion. When the compositions are dosed topically, they will generally be in a concentration range of from 0.1 to about 10% w/v, administered 1-4 times per day.

Desired time intervals for delivery of multiple doses of a particular composition can be determined by one of ordinary skill in the art employing no more than routine experimentation. The conjugate can be comprised of non-antigenic polymeric substances such as dextran, polyvinyl pyrrolidones, polysaccharides, starches, polyvinyl alcohols, polyacryl amides or other similar substantially non-immunogenic polymers. Polyethylene glycol (PEG) is preferred. Other poly(alkylenes oxides) include monomethoxy-polyethylene glycol polypropylene glycol, block copolymers of polyethylene glycol, and polypropylene glycol and the like. The polymers can also be distally capped with C1-4 alkyls instead of monomethoxy groups. The poly(alkylene oxides) used must be soluble in liquid at room temperature. Thus, they preferably have a molecular weight from about 200 to about 20,000 daltons, more preferably about 2,000 to about 10,000 and still more preferably about 5,000.

In one embodiment, the invention provides for the administration of a salt of a compound as described herein as well. In one embodiment, the salt is a pharmaceutically acceptable salt, which, in turn may refer to non-toxic salts of compounds (which are generally prepared by reacting the free acid with a suitable organic or inorganic base) and include, but are not limited to, the acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandlate, mesylate, methylbromide, methylnitrate, methylsulfate, mucate, napsylate, nitrate, oleate, oxalate, pamaote, palmitate, panthothenate, phosphate, diphospate, polygalacturonate, salicylate, stearate, subacetate, succinate, tannate, tartrate, teoclate, tosylate, triethiodide, and valerate salts, as well as mixtures of these salts.

In one embodiment, the use of a single chemical entity with potent anti-oxidant, membrane-stabilizing, anti-proliferative, anti-chemokine, anti-migratory, and anti-inflammatory activity provides the desired protection for a subject afflicted with arthritis, or in another embodiment, the methods of this invention provide for use of a combination of the compounds described. In another embodiment, the compounds for use in the present invention may be provided in a single formulation/composition, or in another embodiment, multiple formulations may be used. In one embodiment, the formulations for use in the present invention may be administered simultaneously, or in another embodiment, at different time intervals, which may vary between minutes, hours, days, weeks or months.

In one embodiment the compositions comprising the compounds for use in the present invention may be administered via different routes, which in one embodiment, may be tailored to provide different compounds at different sites, for example some compounds may be given by intra-joint injection to provide for superior relief in-situ, and in another embodiment, some formulations/compounds/compositions may be provided via various topical formulations, or in another embodiment, systemically, to provide for broader effect.

In one embodiment, the compounds for use in the invention may be used for acute treatment of temporary conditions, or may be administered chronically, as needed. In one embodiment of the invention, the concentrations of the compounds will depend on various factors, including the nature of the condition to be treated, the condition of the patient, the route of administration and the individual tolerability of the compositions.

In one embodiment, the methods of this invention provide for the administration of the compounds throughout the life of the subject, or in another embodiment, episodically, in response to severity or constancy of symptomatic stages, or in another embodiment, at the onset of pain associated with arthritis. In another embodiment, the patients to whom the lipid or PL conjugates should be administered are those that are experiencing symptoms of disease or who are at risk of contracting the disease or experiencing a recurrent episode or exacerbation of the disease, or pathological conditions associated with the same.

As used herein, the term "pharmaceutically acceptable carrier" refers to any formulation which is safe, and provides the appropriate delivery for the desired route of administration of an effective amount of at least one compound of the present invention. As such, all of the above-described formulations of the present invention are hereby referred to as "pharmaceutically acceptable carriers." This term refers to as well the use of buffered formulations wherein the pH is maintained at a particular desired value, ranging from pH 4.0 to pH 9.0, in accordance with the stability of the compounds and route of administration.

For parenteral application, particularly suitable are injectable, sterile solutions, preferably oily or aqueous solutions, as well as suspensions, emulsions, or implants, including suppositories. Ampoules are convenient unit dosages.

For topical application, particularly for the treatment of skin diseases such as contact dermatitis or psoriasis, admixture of the compounds with conventional creams or delayed release patches is acceptable.

For enteral application, particularly suitable are tablets, dragees, liquids, drops, suppositories, or capsules. Syrup, elixir, or the like can be used when a sweetened vehicle is employed. When indicated, suppositories or enema formulations may be the recommended route of administration.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Articular injection are used for treating an osteoarthritic joint with at least one of the compounds as described herein in a concentration of 1-50 mg/ml in a volume of 1-10 ml/injection.

The compounds as described herein may be administered in different ways, for example, periarticular injection, peritendonous injection, periligamentous injection or intramuscular perfusion. Methods of making such injections are known to one of ordinary skill in the art. Such injections are generally subcutaneous and target the vicinity of a joint, especially near the insertions or origins of muscle tendons and ligaments. Local analgesics may be provided at the site of injection. Such analgesics are known to one of ordinary skill in the art.

Further active substances that can be used in an injectable dosage form are: antibiotics, antiseptics, sodium hyaluronate, a glucocorticoidor any combination thereof. Excipients include but are not limited to: isotonizing agents, such as sodium chloride, mannitol, or sorbitol, water for injection as solvent, sodium monohydrogenphosphate, and sodium dihydrogenphosphate. The solution may additionally contain pH modifiers, such as sodium hydroxide, sodium hydrogenphosphate, hydrochloric acid, or citric acid; surfactants, such as polysorbate 80; sodium edetate as stabilizer (synergistic antioxidative agent); propylene glycol or polyethylene glycol as cosolvent; and/or antimicrobial agents, like benzyl alcohol, methyl- and propyl-4-hydroxybenzoate, or cetylpyridinium chloride. In the treatment of larger joints, such as the knee, hip or shoulder, syringes of 10-40 mg/2.0 ml are used.

Suspension formulations additionally contain stabilizers, such as carmellose sodium, hypromellose or gelatine, to avoid or reduce the sedimentation of the suspension as far as possible, and to allow for a fast and reliable re-dispersion of the suspension prior to application. It is essential that the crystals in the suspension formulations maintain their particle size. An uncontrolled growth of crystals bears the risk of poor biocompatibility of the suspension formulation upon intra-articular injection.

The injectable formulations can be also formulated as a dry powder which has to be re-dispersed by addition of the dispersing medium (e.g., water for injection). For suspension formulations, it is essential that they are re-dispersed directly before the application, and that the resulting suspension appears homogenous.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Methods of Inhibiting Angiogenesis Using PL Conjugates

In another embodiment, provided herein a method for using the conjugates described herein as cell proliferation inhibitors. In another embodiment, provided herein a method for using the conjugates described herein as endothelial cell proliferation inhibitors. In another embodiment, provided herein a method for using the conjugates of the invention as endothelial cell migration inhibitors. In another embodiment, provided herein a method for using the conjugates of the invention as inhibitors of blood vessel formation. In another embodiment, provided herein a method for using the conjugates of the invention as inhibitors of the vascular system. In another embodiment, provided herein a method for using the conjugates of the invention as angiogenesis inhibitors. In another embodiment, provided herein a method for using the conjugates of the invention as angiogenesis inhibitors for treating cancer. In another embodiment, provided herein a method for using the conjugates of the invention as angiogenesis inhibitors for treating other diseases caused by abnormal blood-vessel growth. In another embodiment, the terms "angiogenesis" and "neovascularization" are used interchangeably.

In another embodiment, angiogenesis inhibitors as described herein are neovascularization inhibitors. In another embodiment, angiogenesis inhibitors as described herein are neovascularization blockers.

In another embodiment, provided herein a method for using the conjugates of the invention for delaying the development of primary tumors and metastatic lesions that are angiogenesis dependent. In another embodiment, provided herein a method for using the conjugates of the invention for inhibiting the migration of endothelial cells to a newly formed tumor and their proliferation.

In another embodiment, provided herein a method for using the conjugates of the invention for treating eye diseases. In another embodiment, provided herein a method for using the conjugates of the invention as angiogenesis inhibitors for treating diabetic retinopathy. In another embodiment, provided herein a method for using the conjugates of the invention as angiogenesis inhibitors for treating a subject afflicted with macular degeneration. In another embodiment, provided herein a method for using the conjugates of the invention as angiogenesis inhibitors for treating age-related macular degeneration. In another embodiment, provided herein a method for using the conjugates of the invention for inhibiting neovascularization of blood vessels in the eye. In another embodiment, provided herein a method for using the conjugates of the invention for inhibiting and/or preventing neovascularization of blood vessels in the retina. In another embodiment, provided herein a method for using the conjugates of the invention for inhibiting and/or preventing leakage of blood vessels in the retina. In another embodiment, provided herein a method for using the conjugates of the invention for preventing and/or inhibiting scarring in the macula. In another embodiment, provided herein a method for using the conjugates of the invention for preventing loss of central vision. In another embodiment, provided herein a method for using the conjugates in an injectable dosage form. In another embodiment, provided herein a method for injecting the conjugates into the vitreous of the eyeball. In another embodiment, provided herein a method for injecting the conjugates into the subretinal space. In another embodiment, provided herein a method for injecting the conjugates into the eye thereby blocking neovascularization and preventing bleeding into the retina.

In another embodiment, treating macular degeneration is inhibiting neovascularization in the retina. In another embodiment, inhibiting the development of a macular degeneration disease is inhibiting neovascularization in the retina.

In another embodiment, provided herein a method for using the conjugates of the invention as angiogenesis inhibitors for reducing the risk of blindness. In another embodiment, provided herein a method for using the conjugates of the invention as angiogenesis inhibitors for reducing the risk of retinopathy of prematurity in preterm infants. In another embodiment, the conjugates of the invention act as development inhibitors of new blood vessels in the eye that are weak and leaky and prone to hemorrhage. In another embodiment, the conjugates of the invention inhibit the formation of new blood vessels in the eye that are weak and leaky and prone to hemorrhage.

In another embodiment, provided herein a method for using the conjugates of the invention for treating obesity. In another embodiment, provided herein a method for using the conjugates of the invention for reducing the growth of fat tissue. In another embodiment, provided herein a method for using the conjugates of the invention for reducing the growth of adipose tissue. In another embodiment, provided herein a method for eliminating fat cells as a consequence of inhibiting angiogenesis. In another embodiment, provided herein a method for shedding a significant percentage of weight in an obese subject. In another embodiment, provided herein a method for using the conjugates of the invention for treating a subject afflicted with Obesity (angiogenesis induced by fat diet). In another embodiment, provided herein a method for using the conjugates of the invention for inducing weight loss.

In another embodiment, provided herein a method for using the conjugates of the invention for treating vascular anomalies. In another embodiment, provided herein a method for using the conjugates of the invention for treating vascular malformations. In another embodiment, provided herein a method for using the conjugates of the invention for treating tangles of irregular blood vessels. In another embodiment, provided herein a method for using the conjugates of the invention for treating vascular tumors. In another embodiment, provided herein a method for using the conjugates of the invention for treating hemangiomas.

In another embodiment, provided herein a method for using the conjugates of the invention for treating hemangiomas in young babies. In another embodiment, provided herein a method for using the conjugates of the invention for treating hemangiomas in babies that are 0-36 moths old. In another embodiment, provided herein a method for using the conjugates of the invention for treating hemangiomas in babies that are 6-24 moths old. In another embodiment, provided herein a method for using the conjugates of the invention for treating hemangiomas in babies that are 6-12 moths old. In another embodiment, provided herein a method for using the conjugates of the invention for treating hemangiomas in subjects that are up to 15 years old. In another embodiment, provided herein a method for using the conjugates of the invention for treating hemangiomas in subjects that are 3 to 15 years old. In another embodiment, provided herein a method for using the conjugates of the invention for treating hemangiomas in subjects that are 7 to 15 years old. In another embodiment, provided herein a method for using the conjugates of the invention for treating hemangiomas in subjects that are 7 to 12 years old.

In another embodiment, provided herein a method for using the conjugates described herein for treating subjects that develop hemangiomas near an eye. In another embodiment, provided a method for using the conjugates of the invention for treating subjects that develop hemangiomas near a vital organ. In another embodiment, provided a method for using the conjugates described herein for treating subjects afflicted with hemangiomas. In another embodiment, a method for using the conjugates described herein for treating subjects afflicted with hemangiomas by regressing vascular malformations is provided.

In another embodiment, provided herein a method for using the conjugates of the invention for blocking the female reproductive cycle. In another embodiment, provided herein a method for using the conjugates of the invention as contraceptives. In another embodiment, provided herein a method for using the conjugates of the invention as oral contraceptives. In another embodiment, inhibiting angiogenesis in the endometrium in a female is blocking a female reproductive cycle. In another embodiment, inhibiting neovascularization in the endometrium in a female is blocking a female reproductive cycle.

In another embodiment, provided herein a method for using the conjugates of the invention for regulating fertility in a female mammal. In another embodiment, provided herein a method for using the conjugates of the invention for regulating fertility in a female mammal comprising administering to such female a conjugate as described herein. In another embodiment, provided herein a method for using the conjugates of the invention for terminating a pregnancy. In another embodiment, provided herein a method for using the conjugates of the invention for inhibiting angiogenesis in the uterus. In another embodiment, provided herein a method for using the conjugates of the invention for inhibiting angiogenesis in the ovary. In another embodiment, provided herein a method for using the conjugates of the invention for inhibiting angiogenesis in the placenta. In another embodiment, provided herein a method for using the conjugates of the invention for inhibiting angiogenesis in the fetus. In another embodiment, provided herein a method for using the conjugates of the invention for inhibiting angiogenesis prior to, during, or after decidualization, placental formation, yolk sac or fetal development. In another embodiment, provided herein a method for using the conjugates of the invention for inhibiting angiogenesis prior to intercourse, after intercourse or after ovum fertilization.

In another embodiment, provided herein a method for using the conjugates of the invention for treating endometriosis. In another embodiment, conjugates of the invention inhibit the migration of tissue from the lining of the uterus to the ovaries, urethra and other pelvic structures. In another embodiment, conjugates of the invention inhibit the unwanted tissue by robbing it of its rich blood supply.

In another embodiment, provided herein a method for using the conjugates of the invention for the treatment of reproductive diseases and conditions that are mediated by or associated with angiogenesis. In another embodiment, provided herein a method for administering to a female mammal an effective amount of a fertility regulating angiogenesis inhibiting conjugate, wherein the conjugate is administered either to prevent conception or to terminate a pregnancy. In another embodiment, the angiogenesis inhibiting conjugate is administered in a single dose or in multiple doses.

In another embodiment, the angiogenesis inhibiting conjugate inhibits angiogenesis in the ovary, obstructing the development of requisite vascularization, thereby preventing the normal release of hormones necessary for conception. In another embodiment, the angiogenesis inhibiting conjugate functions as a prophylactic to conception. In another embodiment, the angiogenesis inhibiting conjugate prevents the formation and engorgement of the tissue necessary for implantation. In another embodiment, the angiogenesis inhibiting conjugate obliterates the necessary conditions for the maturation of the blastocyst. In another embodiment, the angiogenesis inhibiting conjugate inhibits corpus luteaum formation. In another embodiment, the angiogenesis inhibiting conjugate is effective as a contraceptive without complete suppression of menstrual cycles or other systemic side effects. In another embodiment, the angiogenesis inhibiting conjugate inhibits the vascularization of the mucosa of the uterine tube thus interfering with the implantation of the blastocyst in this portion the female reproductive tract. In another embodiment, the angiogenesis inhibiting conjugate does not permanently impair the reproductive system.

In another embodiment, provided herein a method for using the conjugates of the invention for treating pathogenesis of inflammatory disorders such as arthritis. In another embodiment, provided herein a method for using the conjugates of the invention for treating pathogenesis of inflammatory disorders such as rheumatoid arthritis. In another embodiment, provided herein a method for using the conjugates of the invention for treating arthritis. In another embodiment, provided herein a method for using the conjugates of the invention for treating osteoarthritis. In another embodiment, "rheumatoid arthritis" as used herein refers to a chronic systemic disease primarily of the joints, usually polyarticular, marked by inflammatory changes in the synovial membranes and articular structures and by muscle atrophy and rarefaction of the bones. Forms of rheumatoid arthritis include in another embodiment, but are not limited to, juvenile, chronic villous, cricoarytenoid, deformans, degenerative, mutilans, and proliferative.

In another embodiment, provided herein a method for using the conjugates of the invention for inhibiting and/or blocking induction of proliferative vascular response from host vessels by a tumor. In another embodiment, provided herein a method for using the conjugates of the invention for inhibiting and/or blocking the formation of new vessels that supply the tumor with the nutrients it needs to grow. In another embodiment, provided herein a method for using the conjugates of the invention for inhibiting and/or blocking tumor growth. In another embodiment, provided herein a method for using the conjugates of the invention for inhibiting and/or blocking metastasis. In another embodiment, provided herein a method for using the conjugates of the invention as antivascular therapy for cancer. In another embodiment, provided herein a method for using the conjugates of the invention as anti-angiogenic drugs which aim to inhibit new vessel formation. In another embodiment, provided herein a method for using the conjugates of the invention as vascular targeting compounds which aim to selectively destroy the blood vessels supplying the tumor leading to secondary tumor cell death. In another embodiment, provided herein a method for using the conjugates of the invention as antitumoral compounds. In another embodiment, the tumor is a solid tumor.

In another embodiment, provided herein a method for using the conjugates of the invention for treating a subject afflicted with cancer associated with angiogenesis. In another embodiment, provided herein a method of inhibiting cancer associated with angiogenesis. In another embodiment, cancer associated with angiogenesis is a cancer mediated by or associated with angiogenesis. In another embodiment, cancer associated with angiogenesis is a cancer that can be slowed down, inhibited, or cured by blocking the formation of new blood vessels. In another embodiment, cancer associated with angiogenesis is a cancer comprising a tumor, wherein tumor's growth is "angiogenesis dependent". In another embodiment, cancer associated with angiogenesis is a cancer comprising tumors that can be kept stable by the conjugates of the invention. In another embodiment, cancer associated with angiogenesis is a cancer that induces angiogenesis. In another embodiment, cancer associated with angiogenesis is a cancer comprising a tumor which induces angiogenesis. In another embodiment, cancer associated with angiogenesis is a cancer wherein angiogenesis performs a role in the development of the cancer. In another embodiment, cancer associated with angiogenesis is a cancer wherein neovascularization influences the dissemination of cancer cells. In another embodiment, cancer associated with angiogenesis is a cancer wherein neovascularization induces the dissemination of cancer cells. In another embodiment, cancer associated with angiogenesis is a cancer wherein angiogenesis has a role in the switch from premalignant to malignant lesions. In another embodiment, cancer associated with angiogenesis is a cancer wherein conjugates as described herein can induce apoptosis of tumor cells which reside in proximity to an endothelium.

In another embodiment, provided herein a method for using the conjugates of the invention for inhibiting the metastasis of tumors. In another embodiment, provided herein a method for using the conjugates of the invention for inhibiting the metastasis of primary tumors. In another embodiment, provided herein a method for using the conjugates of the invention for causing a primary tumor to regress. In another embodiment, provided herein a method for using the conjugates of the invention combined with other anti-cancer compounds and/or therapies for treating and/or inhibiting cancer associated with angiogenesis.

In another embodiment, provided herein a method for using the conjugates of the invention for treating a subject afflicted with breast cancer. In another embodiment, provided herein a method for using the conjugates of the invention for treating a subject afflicted with esophageal cancer. In another embodiment, provided herein a method for using the conjugates of the invention for treating a subject afflicted with gastrointestinal stromal tumor (GIST). In another embodiment, provided herein a method for using the conjugates of the invention for treating a subject afflicted with liver cancer. In another embodiment, provided herein a method for using the conjugates of the invention for treating a subject afflicted with adult primary liver cancer. In another embodiment, provided herein a method for using the conjugates of the invention for treating a subject afflicted with melanoma. In another embodiment, provided herein a method for using the conjugates of the invention for treating a subject afflicted with multiple myeloma. In another embodiment, provided herein a method for using the conjugates of the invention for treating a subject afflicted with ovarian cancer. In another embodiment, provided herein a method for using the conjugates of the invention for treating a subject afflicted with ovarian epithelial cancer. In another embodiment, provided herein a method for using the conjugates of the invention for treating a subject afflicted with prostate cancer. In another embodiment, provided herein a method for using the conjugates of the invention for treating a subject afflicted with pancreatic cancer. In another embodiment, provided herein a method for using the conjugates of the invention for treating a subject afflicted with gastric cancer. In another embodiment, provided herein a method for using the conjugates of the invention for treating a subject afflicted with colorectal cancer. In another embodiment, provided herein a method for using the conjugates of the invention for treating a subject afflicted with lung cancer. In another embodiment, provided herein a method for using the conjugates of the invention for treating a subject afflicted with Non-small cell lung cancer. In another embodiment, provided herein a method for using the conjugates of the invention for treating a subject afflicted with renal cancer. In another embodiment, provided herein a method for using the conjugates of the invention for treating a subject afflicted Kaposi's sarcoma. In another embodiment, provided herein a method for using the conjugates of the invention for treating a subject afflicted with AIDS and Kaposi's sarcoma.

In another embodiment, provided herein a method for using the conjugates of the invention for treating a subject afflicted with solid leukemia. In another embodiment, provided herein a method for using the conjugates of the invention for treating a subject afflicted with a liquid leukemia. In another embodiment, provided herein a method for using the conjugates of the invention for treating a subject afflicted with lymphoma. In another embodiment, provided herein a method for using the conjugates of the invention for treating a subject afflicted with myeloma.

In another embodiment, provided herein a method for using the conjugates of the invention for treating a subject afflicted with angiofibroma. In another embodiment, provided herein a method for using the conjugates of the invention for treating a subject afflicted with juvenile angiofibroma. In another embodiment, the types of cancer provided herein are cancers associated with angiogenesis.

In another embodiment, provided herein a method for using the conjugates of the invention for treating a subject afflicted with Alzheimer's disease. In another embodiment, provided herein a method for using the conjugates of the invention for inhibiting the formation of harmful brain microvessels.

In another embodiment, provided herein a method for using the conjugates of the invention for treating a subject afflicted with psoriasis. In another embodiment, provided herein a method for using the conjugates of the invention for inhibiting the neovascularization of psoriatic plaques. In another embodiment, provided herein a method for using the conjugates of the invention for reducing the size of psoriatic plaques. In another embodiment, provided herein a method for using the conjugates of the invention for inhibiting development of psoriatic plaques. In another embodiment, provided herein a method for using the conjugates of the invention for curing psoriatic plaques.

In another embodiment, provided herein a method for using the conjugates of the invention for treating a subject afflicted with an auto-immune disorder such as systemic sclerosis or multiple sclerosis. In another embodiment, provided herein a method for using the conjugates of the invention for treating a subject afflicted with Sjögren's disease. In another embodiment, provided herein a method for using the conjugates of the invention for treating a subject afflicted with a vascular malformation. In another embodiment, provided herein a method for using the conjugates of the invention for treating a subject afflicted with DiGeorge syndrome. In another embodiment, provided herein a method for using the conjugates of the invention for treating a subject afflicted with hereditary hemorrhagic telangiectasia. In another embodiment, provided herein a method for using the conjugates of the invention for treating a subject afflicted with cavernous hemangioma. In another embodiment, provided herein a method for using the conjugates of the invention for treating a subject afflicted with lymphatic malformation. In another embodiment, provided herein a method for using the conjugates of the invention for treating a subject afflicted with transplant arteriopathy and atherosclerosis (plaques contain blood and lymph vessels).

In another embodiment, provided herein a method for using the conjugates of the invention for treating a subject afflicted with warts. In another embodiment, provided herein a method for using the conjugates of the invention for treating a subject afflicted with allergic dermatitis. In another embodiment, provided herein a method for using the conjugates of the invention for treating a subject afflicted with scar keloid. In another embodiment, provided herein a method for using the conjugates of the invention for treating a subject afflicted with pyogenic granulomas. In another embodiment, provided herein a method for using the conjugates of the invention for treating a subject afflicted with a blistering disease. In another embodiment, provided herein a method for using the conjugates of the invention for treating a subject afflicted with systemic sclerosis. In another embodiment, provided herein a method for using the conjugates of the invention for treating a subject afflicted with persistent hyperplastic vitreous syndrome. In another embodiment, provided herein a method for using the conjugates of the invention for treating a subject afflicted with diabetic retinopathy. In another embodiment, provided herein a method for using the conjugates of the invention for treating a subject afflicted with retinopathy of prematurity. In another embodiment, provided herein a method for using the conjugates of the invention for treating a subject afflicted with choroidal neovascularization. In another embodiment, provided herein a method for using the conjugates of the invention for treating a subject afflicted with primary pulmonary hypertension. In another embodiment, provided herein a method for using the conjugates of the invention for treating a subject afflicted with chronic airway inflammation. In another embodiment, provided herein a method for using the conjugates of the invention for treating a subject afflicted with cystic fibrosis. In another embodiment, provided herein a method for using the conjugates of the invention for treating a subject afflicted with inflammatory bowel disease. In another embodiment, provided herein a method for using the conjugates of the invention for treating a subject afflicted with ulcerative colitis. In another embodiment, provided herein a method for using the conjugates of the invention for treating a subject afflicted with a periodontal disease. In another embodiment, provided herein a method for using the conjugates of the invention for treating a subject afflicted with ascites. In another embodiment, provided herein a method for using the conjugates of the invention for treating a subject afflicted with liver cirrhosis. In another embodiment, provided herein a method for using the conjugates of the invention for treating a subject afflicted with endometriosis. In another embodiment, provided herein a method for using the conjugates of the invention for treating a subject afflicted with uterine bleeding. In another embodiment, provided herein a method for using the conjugates of the invention for treating a subject afflicted with ovarian cysts. In another embodiment, provided herein a method for using the conjugates of the invention for treating a subject afflicted with ovarian hyperstimulation. In another embodiment, provided herein a method for using the conjugates of the invention for treating a subject afflicted with synovitis. In another embodiment, provided herein a method for using the conjugates of the invention for treating a subject afflicted with osteomyelitis. In another embodiment, provided herein a method for using the conjugates of the invention for treating a subject afflicted with osteophyte formation. In another embodiment, provided herein a method for using the conjugates of the invention for treating a subject afflicted with HIV-induced bone marrow angiogenesis. In another embodiment, provided herein a method for using the conjugates of the invention for treating a subject afflicted with diabetic nephropathy (enlarged glomerular vascular tufts).

In another embodiment, provided herein a method for using the conjugates of the invention for treating a subject afflicted with a disease accompanied by angiogenesis. In another embodiment, provided herein a method for using the conjugates of the invention for inhibiting vascularization in a patient in need thereof.

Methods of Preventing or Treating Atherosclerosis Using Lipids and PL Conjugates In one embodiment of the invention, the methods of the present invention make use of a compound as described herein for treating a subject suffering from atherosclerosis, reducing or delaying the damage to blood vessels of a subject suffering from a coronary disease, or ameliorating symptoms associated with a coronary disease. In another embodiment of the invention, the methods of the present invention make use of a formulation comprising a compound as described herein for treating a subject suffering from a coronary disease, reducing or delaying the damage to the blood vessels of a subject suffering from a coronary disease, or ameliorating symptoms associated with a coronary disease. In another embodiment, provided herein a method for using the conjugates of the invention for inhibiting formation of new blood vessels during the progression of atherosclerotic plaques and its fragility and rupture, which is the main cause of acute ischemic events.

In another embodiment of the invention, the methods of the present invention make use of a formulation comprising a compound as described herein for treating patients having coronary diseases having an increase in plaque vessels. In another embodiment of the invention, the methods of the present invention make use of a formulation comprising a compound as described herein for treating patients having arteriosclerosis.

In another embodiment of the invention, the methods of the present invention making use of a formulation comprising a compound as described are useful for treating a subject afflicted with a coronary ailment by inhibiting growth of the plaque vessels that are present in lesions associated with such cardiovascular problems. In another embodiment of the invention, the methods of the present invention make use of a formulation comprising a compound as described herein for treating patients afflicted with atherosclerosis. In another embodiment of the invention, the methods of the present invention make use of a formulation comprising a compound as described herein for treating patients afflicted with restenosis. In another embodiment of the invention, the methods of the present invention make use of a formulation comprising a compound as described herein for inhibiting plaque growth. In another embodiment of the invention, the methods of the present invention make use of a formulation comprising a compound as described herein for reducing intimal neovascularization. In another embodiment of the invention, the methods of the present invention make use of a formulation comprising a compound as described herein for inhibiting lesion severity.

In another embodiment of the invention, the methods of the present invention make use of a formulation comprising a compound as described herein as a preventive treatment for an individual showing signs of a coronary vascular problem such as formation of an atherosclerotic lesion. In another embodiment of the invention, the methods of the present invention make use of a formulation comprising a compound as described herein for treating a subject who underwent an assessment of plaque vessel growth, unstable clinical symptoms, or evidence of increased neovascularization in atherosclerotic lesions.

In another embodiment of the invention, the methods of the present invention make use of a formulation comprising a compound as described herein for decreasing the degree of neovascularization thus reducing the risk of intramural hemorrhage. In another embodiment of the invention, the methods of the present invention make use of a formulation comprising a compound as described herein for inhibiting capillaries in the intimal layer of atherosclerotic lesions that are permeable and mechanically weak, which predisposes them to bleed.

In another embodiment of the invention, the methods of the present invention make use of a formulation comprising a compound as described herein for decreasing the number of inflammatory cells in the plaque. In another embodiment of the invention, the methods of the present invention make use of a formulation comprising a compound as described herein for decreasing inflammation in the plaque. In another embodiment of the invention, decreasing inflammation in the plaque comprises reducing mechanical weakness in plaque area. In another embodiment of the invention, decreasing inflammation in the plaque comprises inhibiting thrombosis in the artery. In another embodiment of the invention, decreasing inflammation in the plaque comprises reducing the risk of a heart attacks, strokes and vascular occlusion.

In another embodiment of the invention, the methods of the present invention making use of a formulation comprising a compound as described are utilized in subjects diagnosed with an unstable plaque. In another embodiment of the invention, the methods of the present invention making use of a formulation comprising a compound as described are utilized in subjects having increased plaque thickness beyond 200 microns thickness (Geiringer, E., J. Pathol. Bact. 63: 210-11, 1951). In another embodiment of the invention, the methods of the present invention comprise any method for identifying a potentially unstable plaque that is known to one of average skill in the art.

In another embodiment of the invention, the plaque is contacted with a compound as described by any means of administration. For example, subcutaneous injection of the agent, oral administration, or injection by a catheter or needle. In another embodiment of the invention, a standard catheter delivery system is used to deliver a conjugate as described herein to the region where the plaque is present. In another embodiment, these methods include use of a hydrophilic polymer coated balloon such as a hydrogel polymer coated balloon. In another embodiment, these methods include use of balloon catheter. In another embodiment, these methods include use of porous balloon catheter.

In another embodiment of the invention, the methods of the present invention making use of a formulation comprising a compound as described are useful for treating early-stage lesions in the entire aorta. In another embodiment of the invention, the methods of the present invention making use of a formulation comprising a compound as described are useful for inhibiting plaque growth and thereby inhibiting lesion severity. In another embodiment of the invention, the methods of the present invention making use of a formulation comprising a compound as described are useful in preventing serious obstruction. In another embodiment of the invention, the methods of the present invention making use of a formulation comprising a compound as described are useful as a prophylactic mean to prevent development of vascular ailments such as atherosclerosis, stroke, myocardial infarction, etc.

In another embodiment of the invention, the methods of the present invention making use of a formulation further comprising an additional cardiovascular drau such as but not limited to a beta-blocker, ACE inhibitor, cholesterol lowering drugs, etc. In another embodiment of the invention, the cholesterol lowering drug is a statin. In another embodiment of the invention, the cholesterol lowering drug is a bile acid sequestrant.

In another embodiment of the invention, screening methods for the detection individuals afflicted with plaque instability comprise markers that are specifically associated with plaques. In another embodiment of the invention, the markers include those that may be detected by X-radiography, NMR or MRI. In another embodiment of the invention, for X-radiographic techniques, suitable markers include any radioisotope that emits detectable radiation but that is not overtly harmful to the subject, such as barium or cesium, for example. In another embodiment of the invention, suitable markers for NMR and MRI generally include those with a detectable characteristic spin, such as deuterium, which may be incorporated into the antibody by suitable labeling of nutrients for the relevant hybridoma, for example.

In another embodiment of the invention, those of ordinary skill in the art will recognize that a large variety of possible moieties can be coupled to the antibodies or other molecules of the invention.

In another embodiment, a method of treating a subject afflicted with atherosclerosis comprises the use of a formulation comprising a compound as described for uptake of lipoprotein. In another embodiment, a method of treating a subject afflicted with atherosclerosis comprises the use of a formulation comprising a compound as described for uptake of oxidized lipoprotein. In another embodiment, a method of treating a subject afflicted with atherosclerosis comprises the use of a formulation comprising a compound as described for uptake of LDL. In another embodiment, a method of treating a subject afflicted with atherosclerosis comprises the use of a formulation comprising a compound as described for uptake of oxidized LDL.

In another embodiment, a method of ameliorating symptoms associated with atherosclerosis comprises the use of a formulation comprising a compound as described for uptake of lipoprotein. In another embodiment, a method of ameliorating symptoms associated with atherosclerosis comprises the use of a formulation comprising a compound as described for uptake of oxidized lipoprotein. In another embodiment, a method of ameliorating symptoms associated with atherosclerosis comprises the use of a formulation comprising a compound as described for uptake of LDL. In another embodiment, a method of ameliorating symptoms associated with atherosclerosis comprises the use of a formulation comprising a compound as described for uptake of oxidized LDL.

In another embodiment, a method of inhibiting the development of atherosclerosis or an atherosclerotic plaque comprises the use of a formulation comprising a compound as described for uptake of lipoprotein. In another embodiment, a method of inhibiting the development of atherosclerosis or an atherosclerotic plaque comprises the use of a formulation comprising a compound as described for uptake of oxidized lipoprotein. In another embodiment, a method of inhibiting the development of atherosclerosis or an atherosclerotic plaque comprises the use of a formulation comprising a compound as described for uptake of LDL. In another embodiment, a method of inhibiting the development of atherosclerosis or an atherosclerotic plaque comprises the use of a formulation comprising a compound as described for uptake of oxidized LDL.

In another embodiment, provided herein a method of treating a subject afflicted with osteoarthritic knee pain comprising the step of administering a composition comprising a compound of the invention to the subject. In another embodiment, provided herein a method of treating a subject afflicted with osteoarthritic knee pain comprising the step of injecting into a knee a composition comprising a compound of the invention.

In one embodiment, a composition as described herein further comprises dipalmitoyl phosphatidylethanolamine and/or heparin. In one embodiment, the composition for use in the present invention comprises dipalmitoyl phosphatidylethanolamine and chondroitin sulfate. In one embodiment, the composition for use in the present invention comprises dipalmitoyl phosphatidylethanolamine and hyaluronic acid. In one embodiment, the composition for use in the present invention comprises dipalmitoyl phosphatidylethanolamine and carboxymethylcellulose. In one embodiment, the composition for use in the present invention comprises dimyristoyl phosphatidylethanolamine and hyaluronic acid.

In another embodiment, the composition for use in the present invention is a dipalmitoyl phosphatidylethanolamine conjugated via an amide or ester bond to a glycosaminoglycan. In one embodiment, the composition for use in the present invention comprises a dipalmitoyl phosphatidylethanolamine conjugated via an amide or ester bond to a chondroitin sulfate, which is chondroitin-6-sulfate, chondroitin-4-sulfate or a derivative thereof. In another embodiment, the composition for use in the present invention comprises a dipalmitoyl phosphatidylethanolamine conjugated via an amide or ester bond to a heparin. In another embodiment, the composition for use in the present invention comprises a dipalmitoyl phosphatidylethanolamine conjugated via an amide or ester bond to a hyaluronic acid. In another embodiment, the composition for use in the present invention comprises a dimyristoyl phosphatidylethanolamine conjugated via an amide or ester bond to a hyaluronic acid.

In another embodiment, arthritis is a joint inflammation in any part of the body. In another embodiment, arthritis is a rheumatic disease. In one embodiment, the lipid-conjugates display a wide-range combination of cytoprotective pharmacological activities, which are useful in the present invention. In one embodiment, the compounds may be useful for their anti-inflammatory effects, as the inflammatory process itself may be partially or mostly responsible for arthritis. Cellular elaboration of cytokines and chemokines serve an important regulatory function in health; however, when a hyperactive response to stress or disease is triggered, these compounds may present in excess and damage tissue, thereby pushing the disease state toward further deterioration. In one embodiment, the lipid compounds for use in the methods of this invention, possess a combination of multiple and potent pharmacological effects, including inter-alia the ability to inhibit the extracellular form of the enzyme phospholipase A2.

In another embodiment, lipid-conjugates are useful in affecting inflammation in a subject with arthritis, where the subject is administered lipid-conjugates at pre-symptomatic stages of the disease.

The compounds, in some embodiments, are able to stabilize biological membranes; inhibit cell proliferation; suppress free radical production; suppress nitric oxide production; reduce cell migration across biological barriers; influence chemokine levels, including MCP-1, ENA-78, Gro $\alpha$, and CX3C; influence cytokine levels, including IL-6 and IL-8; affect gene transcription and modify the expression of MHC antigens; bind directly to cell membranes and change the water structure at the cell surface; prevent airway smooth muscle constriction; reduce expression of tumor necrosis factor-$\alpha$ (TNF-$\alpha$); modify expression of transcription factors such as NF$\kappa$B; and inhibit extracellular degradative enzymes, including collagenase, heparinase, hyaluronidase, in addition to that of PLA2. In another embodiment, a compound of the present invention reduces the expression of IL-8 thus reducing inflammation, pain swelling, or any combination thereof in an arthritic joint. In another embodiment, an arthritic joint is an inflamed joint of a subject afflicted with arthritis. In another embodiment, an arthritic joint is a swelled joint of a subject afflicted with arthritis. In another embodiment, an arthritic joint is a joint wherein bones are in direct contact in a subject afflicted with arthritis. In another embodiment, a compound as described herein inhibits TNF-alpha thereby inhibits IL-6 production from synovial cells as well as their proliferation. In another embodiment, a compound as described herein inhibits IL-6 production from synovial cells as well as their proliferation. In another embodiment, a compound as described herein inhibits synovial cells proliferation.

In another embodiment, a compound as described herein inhibits the production of IL-6, IL-8, TNF-alpha, or their combination, thereby reducing or delaying the damage to the joints of a subject suffering from arthritis. In another embodiment, a compound as described herein inhibits the production of IL-6, IL-8, TNF-alpha, or their combination, thereby ameliorating symptoms associated with arthritis. In another embodiment, methods comprising the administration of a compound as described herein treat a subject suffering from joint pain, swelling within the joint, inflammation within the joint, or a combination thereof by inhibiting the production of IL-6, IL-8, TNF-alpha, or their combination. In another embodiment, locally administering a composition comprising a compound as described herein by intra-joint injection inhibits the production of IL-6, IL-8, TNF-alpha, or their combination within the joint's cells. In another embodiment, locally administering a composition comprising a compound as described herein by intra-joint injection inhibits inflammation within the joint.

In one embodiment, the compounds for use in the methods of the present invention treat arthritis through exerting at least one of their many pharmacological activities, among which are amelioration, or prevention, of tissue injury arising in the course of pathological disease states by stabilizing cell membranes; limiting oxidative damage; limiting cell proliferation, cell extravasation; suppressing immune responses; or attenuating physiological reactions to stress, as expressed in elevated chemokine levels. In one embodiment of the present invention, the useful pharmacological properties of the lipid or PL-conjugates may be applied for clinical use, and disclosed herein as methods for treatment arthritis. The biological basis of these methods may be readily demonstrated by standard cellular and animal models of disease as known in the art, and as described below.

In another embodiment, the compounds for use in the methods of the present invention treat arthritis through suppression of IL-8 expression. In another embodiment, the compounds for use in the methods of the present invention treat osteoarthritis through suppression of IL-8 expression. In another embodiment, the compounds for use in the methods of the present invention treat rheumatid arthritis through suppression of IL-8 expression. In another embodiment, the compounds for use in the methods of the present invention treat any arthritis disease through suppression of IL-8 expression. In another embodiment, the compounds for use in the methods of the present invention reduce inflammation associated with arthritis through suppression of IL-8 expression. In another embodiment, the compounds for use in the methods of the present invention reduce joint inflammation associated with arthritis through suppression of IL-8 expression. In another embodiment, the compounds for use in the methods of the present invention treat swollen inflamed joints in a subject afflicted with arthritis through the suppression of IL-8 expression.

In one embodiment, the administration of Lipid or PL-conjugates provides a method for decreasing the expression of pro-inflammatory chemokines, cytokines, or a combination thereof. In another embodiment, the administration of Lipid or PL-conjugates provides a method of affecting endogenous activation of NF-$\kappa$B, IL-6 and IL-8 in a joint.

While pharmacological activity of the Lipid or PL conjugates described herein may be due in part to the nature of the lipid moiety, the multiple and diverse combination of pharmacological properties observed for the Lipid or PL-conjugates may represent, in other embodiments, the ability of the compound to act essentially as several different drugs in one chemical entity.

In one embodiment, the invention provides a method of "treating" arthritis or related diseases or disorders, which in one embodiment, refers to both therapeutic treatment and prophylactic or preventative measures, wherein the object is to prevent or lessen the targeted pathologic condition or disorder as described hereinabove. In one embodiment, treating refers to delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decrease the number or frequency of relapse episodes, increasing latency between symptomatic episodes, increasing time to sustained progression, expediting remission, inducing remission, augmenting remission, speeding recovery, or increasing efficacy of or decreasing resistance to alternate therapeutics.

Thus, in one embodiment of the present invention, the compounds of the present invention are directed towards resolution of symptoms of the disease or disorder that result from inflammation as described hereinabove. In another embodiment, the compounds affect the pathogenesis underlying the inflammatory effect described herein.

In one embodiment of the invention, the lipid mediator is a glycerolipid. In another embodiment, the lipid mediator is a phospholipid. In another embodiment, the lipid mediator is sphingolipid. In another embodiment, the lipid mediator is a sphingosine. In another embodiment, the lipid mediator is ceramide. In another embodiment, the lipid mediator is a fatty acid. In another embodiment, the fatty acid is arachidonic acid. In another embodiment, the lipid mediator is an arachidonic acid-derived eicosanoid. In another embodiment, the lipid mediator is a platelet activating factor (PAF). In another embodiment, the lipid mediator is a lysophospholipid.

In one embodiment of the invention, the term "controlling" refers to inhibiting the production and action of any of the factors ad herein described in order to maintain their activity at the normal basal level and suppress their activation in pathological conditions.

In another embodiment, arthritis is a chronic disease, which means that it can affect a subject over a long period of time. In another embodiment, the following symptoms are associated with arthritis: swelling, redness, heat, pain, or any combination thereof within the joint or in the surrounding area. In another embodiment, arthritis symptoms further include but are not limited to: fever, gland swelling (lymph node), weight loss, fatigue, feeling unwell, and even symptoms from abnormalities of organs such as the lungs, heart, or kidneys.

In another embodiment, joint pain and progressive stiffness without noticeable swelling, chills, or fever during normal activities are symptoms of osteoarthritis and are treated by the methods of the invention. In another embodiment, painful swelling, inflammation, and stiffness in the fingers, arms, legs, and wrists occurring in the same joints on both sides of the body, especially on awakening, are symptoms of rheumatoid arthritis. In another embodiment, fever, joint inflammation, tenderness, and sharp pain, sometimes accompanied by chills and associated with an injury or another illness, are symptoms of infectious arthritis. In another embodiment, in children, intermittent fever, loss of appetite, weight loss, and anemia, or blotchy rash on the arms and legs are symptoms of juvenile rheumatoid arthritis.

In another embodiment, arthritis is osteoarthritis. In another embodiment, arthritis is rheumatoid arthritis. In another embodiment, arthritis is Gout. In another embodiment, arthritis is psoriatic arthritis. In another embodiment, arthritis is lupus. In another embodiment, arthritis is septic arthritis.

In another embodiment, the methods as described herein slow the degeneration of joints in a subject afflicted with osteoarthritis. In another embodiment, the methods as described herein slow the progression of arthritis. In another embodiment, the methods as described herein slow cartilage break down. In another embodiment, the methods as described herein reverses cartilage break down. In another embodiment, the methods as described herein inhibit cartilage break down. In another embodiment, formulations comprising the compounds of the invention provide a cartilage-like substitute to the joints. In another embodiment, the methods as described herein slow the progression of osteoarthritis. In another embodiment, the methods as described herein overuse of joints. In another embodiment, the methods as described herein are administered as preventive measures against osteoarthritis to people that are involved with demanding sports, obesity, or aging. In another embodiment, the methods as described herein treat joints that bear weight such as the knees, hips, feet, and spine.

In another embodiment, the methods as described herein are effective in alleviating pain resulting from an osteoarthritic joint. In another embodiment, the methods as described herein are effective in alleviating pain resulting from an osteoarthritic knee. In another embodiment, the methods as described herein are effective in reducing inflammation in a joint lining associated with the breakdown of cartilage.

In another embodiment, arthritis is chronic arthritis such as rheumatoid arthritis. In another embodiment, methods of the present invention treat a subject afflicted with rheumatoid arthritis. In another embodiment, methods of the present invention reduce inflammation and/or pain in joints on both sides of the body (such as hands, wrists or knees) of a subject afflicted with rheumatoid arthritis.

In another embodiment, methods of the present invention are used to treat joint pain and swelling resulting from rheumatoid arthritis. In another embodiment, methods of the present invention are used to treat stiffness and/or fatigue resulting from rheumatoid arthritis. In another embodiment, methods of the present invention inhibit the development of rheumatoid arthritis thus delaying or inhibiting joint symptoms that develop gradually over time. But in some, rheumatoid arthritis may progress rapidly and yet other people may have rheumatoid arthritis for a limited period of time and then enter a period of remission.

In another embodiment, methods of the present invention inhibit the accumulation of cells and inflammatory substances within the joint cause thus inhibiting irritation, wearing down of cartilage, swelling, and inflammation of the joint lining. In another embodiment, methods of the present invention inhibit the accumulation of joint fluid within the joint.

In another embodiment, compositions of the present invention maintain the space between the bones. In another embodiment, compositions of the present invention prevent bone to bone contact. In another embodiment, methods of the present invention prevent irreversible bone damage. In another embodiment, methods of the present invention prevent irreversible bone damage in a subject afflicted with rheumatoid arthritis. In another embodiment, methods of the present invention prevent bumps and nodules under the skin or rheumatoid nodules.

In another embodiment, methods of the present invention are used prior to surgery for correcting damage to the joint. In another embodiment, methods of the present invention are used after a surgery for correcting damage to the joint.

In another embodiment, methods of the present invention further provide medications which prevent or minimize the progression of arthritis. In another embodiment, methods of the present invention further provide administering anti-inflammatory painkiller drugs, such as aspirin, ibuprofen or naproxen, topical pain relievers, corticosteroids, narcotic pain relievers, or any combination thereof. In another embodiment, methods of the present invention further provide administering a disease-modifying anti-rheumatic drug (DMARD).

In another embodiment, methods of the present invention are used to treat a subject afflicted with osteoarthritis. In another embodiment, methods of the present invention prevent stiffness of the cartilage in a joint. In another embodiment, methods of the present invention prevent cartilage wear. In another embodiment, compounds as described herein act as a joint shock absorber. In another embodiment, compounds as described herein replace cartilage as a joint shock absorber. In another embodiment, compounds as described herein induce cartilage renewal. In another embodiment, compounds as described herein induce cartilage renewal in a joint.

In another embodiment, methods of the present invention further provide removal of fluid within the joint (joint aspiration). In another embodiment, methods of treating a subject afflicted with osteoarthritis comprise administering pain killers, anti-inflammatory drugs, and steroids. In another embodiment, methods of the invention comprise injecting a formulation comprising compounds as described herein and steroids directly into the joint.

In another embodiment, intra-joint injections as described herein are administered as a series of 1 to 14 weekly joint injections. In another embodiment, intra-joint injections as described herein are administered as a series of 1 to 5 weekly joint injections. In another embodiment, intra-joint injections as described herein are administered as a series of 3 to 7 weekly joint injections. In another embodiment, intra-joint injections as described herein are administered as a series of 5 to 10 weekly joint injections. In another embodiment, intra-joint injections as described herein are administered as a series of 8 to 12 weekly joint injections. In another embodiment, intra-joint injections as described herein are administered as a series of 10 to 14 weekly joint injections.

In another embodiment, methods as described herein are utilized in treating a subject afflicted with psoriatic arthritis. In another embodiment, methods as described herein ameliorate symptoms associated with psoriatic arthritis. In another embodiment, methods as described herein treat and/or repair psoriatic skin lesions that can occur before the onset of arthritis. Early detection and receiving prompt psoriatic arthritis treatment are essential. Untreated psoriatic arthritis can result in permanent, crippling joint damage. In another embodiment, methods as described herein are effective against psoriasis and psoriatic arthritis, meaning the same methods benefit both joints and skin.

In another embodiment, methods as described herein are effective in treating swelling of the fingers and toes. In another embodiment, methods as described herein are effective in reducing swelling of the fingers and toes.

In another embodiment, methods for treating psoriatic arthritis include administering additional medications such as but not limited to: a nonsteroidal anti-inflammatory drug, an anti-rheumatic drug, topical medication for treating skin lesions, or any combination thereof.

In another embodiment, methods as described herein are useful in treating a subject afflicted with a degenerative disc disease. In another embodiment, methods as described herein are used to compensate for the loss of fluid in discs. In another embodiment, methods as described herein improve the ability of the discs to act as shock absorbers. In another embodiment, methods as described herein comprise injecting a composition of the invention into the spinal cord thus providing means for widening the distance between the vertebrae.

In another embodiment, methods as described herein comprise injecting a composition of the invention comprising a compound as described herein and Hyaluronic acid (HA). In another embodiment, a compound as described herein reduces the risk of local infection in the injection site. In another embodiment, a compound as described herein reduces the risk of systemic infection with a fever. In another embodiment, a compound as described herein reduces the risk of bleeding into the joint space after injection.

In another embodiment, a composition comprising a compound as described herein reduces the accumulation of inflammatory substances such as but not limited to prostaglandins within the inflamed joint thus reducing painful movements. In another embodiment, a composition comprising a compound as described herein compensates for reduced cartilage depth on joint load bearing surfaces. In another embodiment, the methods comprise viscosupplementation. In another embodiment, injecting a formulation comprising a compound of the invention provides viscosupplementation to an arthritic joint. In another embodiment, injecting a formulation comprising a compound of the invention provides viscosupplementation to an osteoarthritic knee.

In another embodiment, a composition comprising a compound as described herein further comprises glucosamine. In another embodiment, a composition comprising a compound as described herein further comprises chondroitin. In another embodiment, a composition comprising a compound as described herein further comprises MSM.

In another embodiment, a compound as described herein acts as a lubricant, protecting adjacent joint surfaces from mechanical damage. In another embodiment, a compound as described herein acts as a shock absorber, protecting the cartilage from compressive trauma. In another embodiment, a compound as described herein facilitates cartilage nutrition of water, electrolytes, and nutrients that can diffuse to cartilage and synovium freely.

In another embodiment, a composition comprising a compound as described herein is injected anteriorly into the knee joint. In another embodiment, local anaesthetic is injected into the skin just to the inner side of the knee cap, and then further local anaesthetic is injected through the tissue layers to the capsule of the knee joint. In another embodiment, a composition comprising a compound as described herein is injected into the centre of the joint slowly over 15-30 seconds.

In another embodiment, methods as described herein repair tears or cracks in the outer layer (annulus or capsule) of the disc. In another embodiment, methods as described herein prevent disc herniation.

In another embodiment, arthritis is gout. In another embodiment, methods as described herein decrease uric acid levels. In another embodiment, methods as described herein are useful in treating an acute gout attack. In another embodiment, methods as described herein inhibit a highly inflammatory arthritis thus reducing swelling, redness and warmth surrounding a joint. In another embodiment, methods as described herein reduce the risk of gouty attacks. In another embodiment, methods as described herein inhibit the development of a chronic arthritis resulting in bone and cartilage destruction and deformity in a gout patient. In another embodiment, methods as described herein decrease uric acid crystals deposit within and surrounding the joint causing a chronic destructive inflammatory process. In another embodiment, methods as described herein inhibit joint inflammation.

In another embodiment, arthritis is Fibromyalgia (FM). In another embodiment, methods as described herein reduce chronic, generalized pain syndrome of unknown origin. In another embodiment, methods as described herein reduce diffuse pain and tenderness. In another embodiment, methods as described herein reduce chronic fatigue associated with FM.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

The compounds for use in the instant invention are collectively referred to as Lipid-conjugates.
Materials and Methods
Cells Endothelial cells from human bone marrow (HBMEC) were established by transfecting human bone marrow endothelial cells with SV40 large T antigen for immortalization. They are kindly provided by Dr. Kenneth J. Pienta (Cancer center, Ann Harbor, Mich., USA). Cells were cultured in complete M131 medium (Cascade Biologics) supplemented with 10% fetal calf serum (FCS), 5% microvascular growth supplement (MVGS) which contains 5% FCS, hydrocortisone, human bFGF, heparin, human epidermal growth factor and dibutyryl cAMP (Cascade Biologics), 1% L-glutamine, 100 IU/ml penicillin and 100 Wg/ml streptomycin.

One of the lipid-conjugates employed in the present study was composed of hyaluronic acid-linked N-derivatized phosphatidyl-ethanolamine (HyPE), designed and synthesized in the laboratory of S. Yedgar, by truncating hyaluronic acid (Gideon Richter, Budapest, Hungary) to a MW of 50-100 kDa, and linking it to the amino head group of dipalmitoyl-phosphatidyl-ethanolamine (PE).
Cell Proliferation Assay For the proliferation assay, a minimal concentration of FCS (7.5%) was used to allow sufficient viability of endothelial cells. Briefly, after trypsinization, the cells were seeded at a concentration of $5\times10^4$ cells in each well of 24-well plates (Nunc, Denmark) and then incubated without or with cytokines (25 ng/ml bFGF, 20 ng/ml VEGF or 2.5 ng/ml OSM). HyPE was added at concentrations of 2.2-20 microM. After incubation for 2 days, cells were detached by trypsin (0.05% w/v; Sigma), resuspended in Isoton II solution (Coulter, France) and counted in a particle counter (CoulterZ1, Coultronics). Hyaluronic acid (HyAc) was used as control.
Cell Migration by Wound Healing Method Endothelial cells were cultured in 24-well culture plates. After reaching 80% confluence, HBMEC were dislodged by a cell scraper under standard conditions. After three times washing the cells with phosphate-buffered saline, the cells were incubated in complete M131 medium in the presence of increasing HyPE concentration (HyAc was used as control). Cell migration was determined by measuring the number of cells migrating into 10 mm² 'wounding area', 18 h after introducing 'the wound' into the confluent monolayer.

Formation of Capillary Tubes in a Model of Angiogenesis in Fibrin Gels

HBMEC were embedded in fibrin matrix, which mimics the in vivo situation where fibrin appears to be a common component of the matrix present at sites of inflammation and/or tumor stroma. This model with microcarrier beads was devised according to the method of Nehls et al. Briefly, HBMEC were allowed to attach to the Cytodex-3 microcarrier beads (Sigma) by incubating cells with beads in M131 containing 10% FCS. The beads were then embedded in a fibrin matrix, obtained by coagulation of a solution of purified fibrinogen at 8 mg/ml in M131 containing 0.2 mM aprotinin, 10% FCS. After addition of thrombin (2 U/ml, final concentration), fibrin gel was formed, and then 500 μl of complete culture medium containing 10% FCS, 5% MVGS was added. Formation of capillary tubes evolving from the surface of the microcarrier beads could be observed after 3 days culture. These capillaries were photographed, the lengths and widths of capillary tubes were measured using the microvision Saisam program (Microvision, Evry, France) on a reverse microscope. Capillary formation was induced by the addition of bFGF (25 ng/ml final concentration), or VEGF (20 ng/ml final concentration), or OSM (2.5 ng/ml final concentration) to the fibrin gel (containing 10% FCS). The eject of N-derivatized phosphatidylethanolamine linked to hyaluronic acid (HyPE) on the capillary formation was examined in two ways: (1) HyPE (20 mM) was added to the fibrin simultaneously with the HBMEC-coated beads and growth factors; (2) HyPE was added after interaction of the cells with the growth factors, to rule out the possibility that HyPE interferes with the interaction of the growth factors with the cell surface. Specifically, HBMEC-coated beads were incubated with the growth factors for a period of 3 h, after which they were washed and incorporated into the ¢brin gel containing HyPE (20 μM).
Statistical Tests Significance values were determined using the two tailed non-parametric Mann-Whitney and Wilcoxon test using Instat software. All results are expressed as the mean value±S.E.M. P<0.05 was regarded as signi¢cant statistical difference.

Example 1

Control of Angiogenic Processes by Inhibition of Spla2 Activity

To comprehensively study the possible control of angiogenic processes by inhibition of sPLA2 activity, the effect of HyPE on HBMEC proliferation, migration and capillary formation was determined. As noted in the materials section, the medium used for cultivation of the endothelial cells is already supplemented with growth factors. To examine the effect of HyPE on growth factor-induced endothelial cell activation, the culture medium was further supplemented with bFGF, VEGF and OSM, which further increased HBMEC stimulation by about 50%, as shown below.
Effect of HyPE on HBMEC Proliferation FIG. 1 shows that HyPE effectively inhibited HBMEC proliferation in a dose-dependent manner, whether the cells were grown in the control culture medium containing standard amount of growth factors, or stimulated with additional amount of VEGF, bFGF or OSM. At the same time, HyAc did not affect the cell proliferation. It should be noted that HyPE did not induce a toxic effect in the endothelial cells.

Effect of HyPE on HBMEC Migration

HBMEC displacement was monitored following wound formation for 18 h, by determining the migration of the cells in the wounded area. The results, presented in Table 2, show that this period of time was sufficient for complete wound covering in normal conditions, but the addition of HyPE exerted a dose-dependent inhibition of HBMEC migration.

TABLE 2

Inhibitory effect induced by HyPE on endothelial cell migration by wound healing method

| | Number of migrated cells |
|---|---|
| HBMEC | 68 ± 7 (complete wound healing) |
| HBMEC + HyPE 2.5 μM | 64 ± 9 (complete wound healing) |
| HBMEC + HyPE 5 μM | 37 ± 5 (incomplete wound healing)*** |
| HBMEC + HyPE 10 μM | 13 ± 6*** |
| HBMEC + HyPE 20 μM | 8 ± 3*** |

After cell scraping, the cells were incubated in complete M131 medium in the absence or presence of HyPE at indicated final concentrations. After 18 h of incubation, cells that migrated in 10 mm$^2$ wounding area were counted. Results of three experiments in duplicate (mean±S.E.M.). ***P<0.005 as compared with control.

Effect of HyPE on Capillary Formation by HBMEC

To study the effect of HyPE on tube formation, HBMEC were cultured on microcarrier beads until they covered the whole bead surface. The beads were embedded in a fibrin matrix and cultivated for 3 days in the control or growth factor-supplemented culture medium. The formation of the HBMEC-derived hollow tube-like structures was visualized and their capillary length was determined as described in the materials section.

Figure 2:
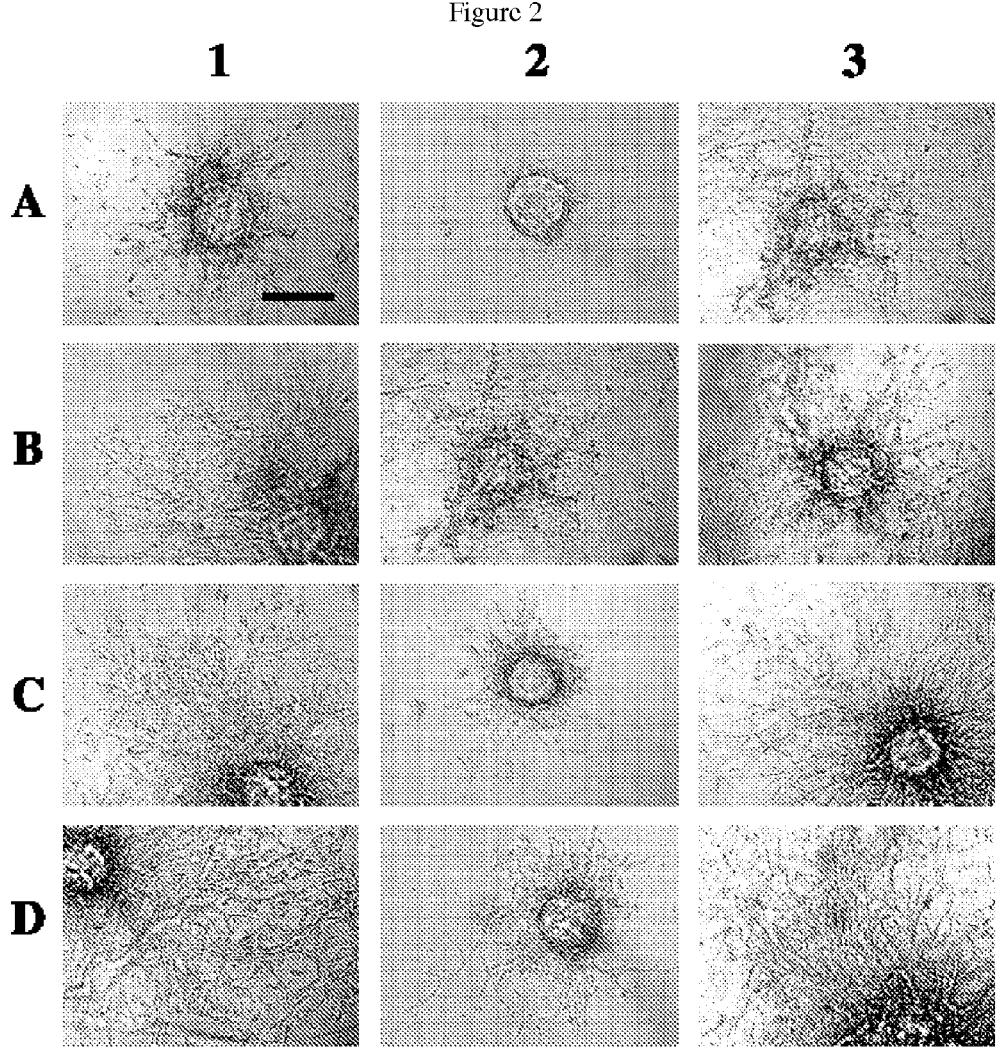
FIG. 2. Micrographs showing the inhibitory effect induced by HyPE on capillary tube formation in a three-dimensional fibrin gel in conditions where growth factors, HyPE (20 μM) or HyAc were added to fibrin simultaneously with HBMEC-1-coated beads. Row A: control; row B: bFGF (25 ng/ml); row C: VEGF (20 ng/ml); row D: OSM (2.5 ng/ml). Column 1: without HyPE; column 2: HyPE 20 μM; column 3: HyAc 20 mM.

Results presented in FIG. 2 show that tube formation in fibrin matrix was enhanced by all angiogenic factors (bFGF, VEGF, and OSM), but this was strongly suppressed by HyPE both in control and in growth factor-supplemented medium. HyAc did not modify the capillary tube formation in both control and stimulated conditions. As shown in Table 3, HyPE clearly decreased the tube dimensions, in particular their length.

TABLE 3

Inhibitory effect induced by HyPE on bFGF-, VEGF- and OSM-stimulated capillary tube formation in a three-dimensional fibrin gel

| Treatment | Length (μm) | | Width (μm) | |
|---|---|---|---|---|
| | −HyPE | +HyPE | −HyPE | +HyPE |
| Control | 232.23 ± 56.13 | 80.31 ± 30.59*** | 9.42 ± 1.65 | 8.32 ± 1.47 |
| BFGF | 533.92 ± 65.02 | 266.73 ± 23.17*** | 15.83 ± 2.96 | 11.21 ± 1.52* |
| VEGF | 511.09 ± 72.05 | 215.68 ± 31.22*** | 14.86 ± 1.46 | 9.32 ± 1.18** |
| OSM | 518.82 ± 58.49 | 234.85 ± 36.32*** | 16.89 ± 1.89 | 10.02 ± 1.00*** |

*P < 0.005, P < 0.01, *P < 0.05

Results of three experiments and for each experiment, five beads were examined. Selected beads were those for which the capillary tubes are the best. Microcarrier beads coated with HBMEC were embedded in ¢ brin matrix in the presence or absence of HyPE (20 μM, final concentration) and growth factors (25 ng/ml bFGF, 20 ng/ml VEGF or 2.5 ng/ml OSM), as indicated in Section 2. After 3 days culture, in the presence or absence of HyPE the lengths and widths of capillary tubes were measured using a microvision program.

In Vivo Angiogenesis

Figure 4A:
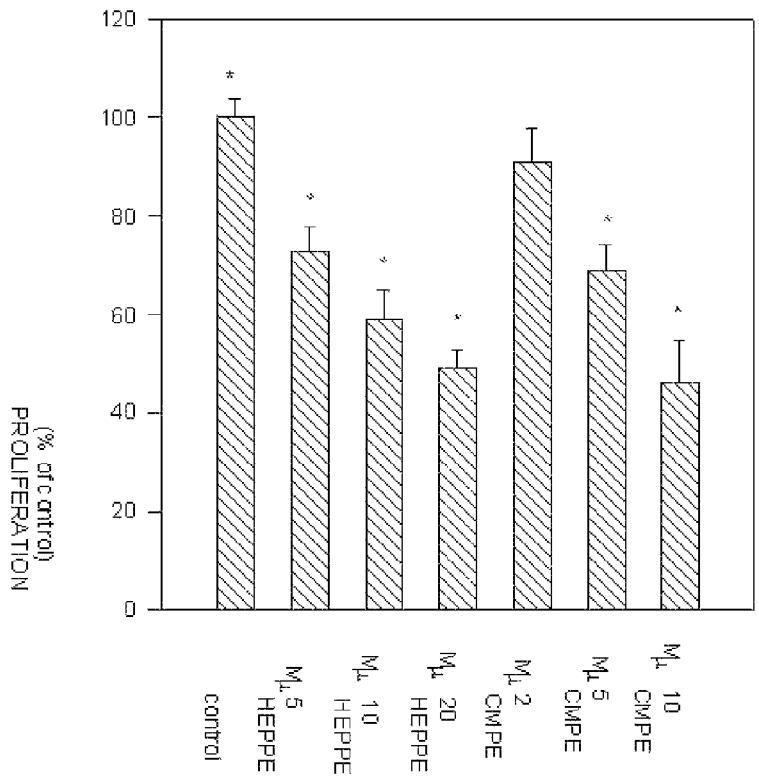
FIG. 4: A bar graph showing the effect of Lipid-conjugates on proliferation of bovine aortic endothelial cells (EC) (A); A bar graph showing the effect HypE on VEGF induced angiogenesis in mice (B).

Ice-cold matrigel was mixed with VEGF (10 ng/ml) and 400 ul injected slowly sub cutaneously on the back of C57B1 six-week-old female mice (n=4 per group). The mice were treated for five days by IP injection (b.i.d) of the indicated dose (vehicle or HyPE. At the end of the experiments, the plaque was excised, photographed and the capillaries' area was measured using an image analysis program (FIG. 4A).

Figure 4B:
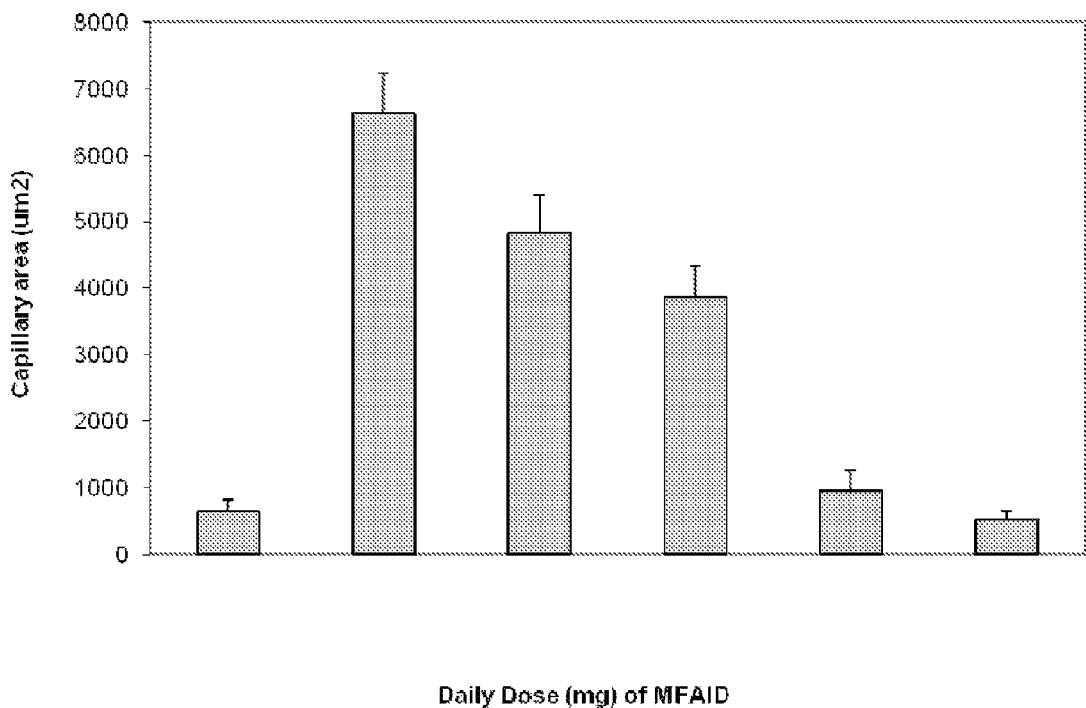

For demonstrating Lipid-conjugate effect on proliferation of endothelial cells, bovine aortic endothelial cells were plated in culture dishes for 6 h, then washed to remove unattached cells. The remaining attached cells were incubated in the absence (control) or presence of Lipid-conjugates at the indicated concentration, and stimulated with VEGF (vascular endothelial growth factor) for 48 h. The cells were then washed, collected by trypsinization and counted in a Coulter counter. The results are mean±S.D. for 3 replications. *p<0.005 (FIG. 4B).

Figure 3:
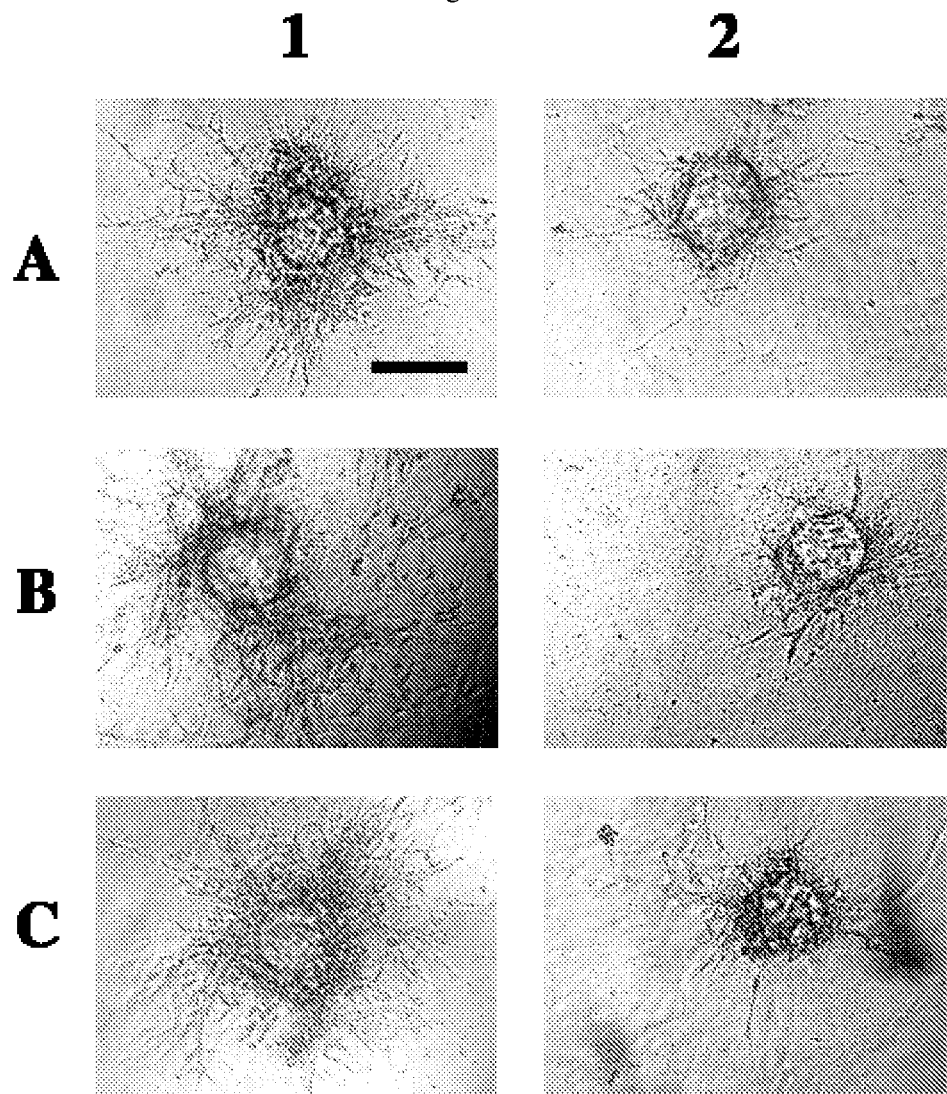
FIG. 3. Micrographs showing the inhibitory effect induced by HyPE on capillary tube formation in a three-dimensional fibrin gel in conditions where HBMEC-coated beads were firstly incubated with the growth factors for a period of 3 hours, and washed and then incorporated into the fibrin gel without or with HyPE. Row A: bFGF (25 ng/ml); row B: VEGF (20 ng/ml); row C: OSM (2.5 ng/ml). Column A: without HyPE; column B: with HyPE (20 μM).

As described above, the extracellular PLA2 inhibitors are composed of an inhibiting lipid moiety (PE) which incorporates into the cell membrane and anchors the polymeric carrier (HyAc) to the cell surface. This raises the possibility that the observed inhibitory effect might be due to interference of the polymeric carrier with the accessibility of the growth factors to the cell surface. To examine this possibility, HBMEC cultured on the micro-carrier beads were first stimulated with the growth factors for 3 h (to allow interaction with their receptors at the cell surface), then washed to remove the unbound growth factors and introduced into HyPE-containing fibrin matrix. As shown in FIG. 3, under these conditions, capillary tube formation was effectively suppressed by HyPE, suggesting that the HyPE effect is not due to a defective growth factor accessibility due to steric hindrance by the polymer at the cell surface of the endothelial cells.

The results of the present study demonstrate that the extracellular sPLA2 inhibitor, HyPE, is a potent regulator of several essential processes required for angiogenesis, specifically, proliferation and migration of human endothelial cells and capillary formation induced by growth factor which are involved in vascularization of tumors (bFGF, VEGF) and atherosclerotic plaque (OSM). The suppression of capillary formation was obtained whether HyPE was added prior to or after stimulation of the cells with the growth factors. Together with the finding that HyAc alone did not affect capillary formation, this suggests that HyPE exerts its inhibitory effect not by hindering the accessibility of the growth factors to the cell surface, but rather by interfering in the signaling process initiated by the growth factors. Taken together, these findings provide support for the key role of sPLA2 in the pathophysiology relating to stimulated angiogenesis and organ vascularization.

Endothelial cell proliferation and angiogenesis involved the participation of various lipid mediators, including lyso-LPs and different eicosanoids, the production of which is initiated by PLA2. Therefore, by suppressing membrane lipid hydrolysis, the extracellular PLA2 inhibitors have the potential to control angiogenesis, by regulating the production of more than one mediator.

All in all, the results and considerations presented support the regulating role of involvement of sPLA2 in processes, present the extracellular PLA2 inhibitors as cell-impermeable PLA2 inhibitors for the control of angiogenesis, thus introducing a novel approach in the research and therapy of cancer and other pathological conditions involving organ vascularization.

Example 2

Invasive Cellular Proliferative Disorders

The Lipid-conjugates are effective therapy for cellular proliferative disorders, such as cancer. This is demonstrated in experiments 7.1-7.3 above and 8.1-8.8 below. The process of cancer spread entails multiple events, each of these is a worthy target for inhibitory drug action, including the rate of cell-proliferation, the rate of spread through blood vessels, the rate of invasiveness through contiguous and non-contiguous (metastases) tissues, and the rate of production of new blood vessels to supply the cancerous growth. Cancer cells frequently produce intracellular matrix tissue degrading enzymes which serve to enhance their invasive potential. Cancer is thus a multiphasic disease involving the process of tissue invasiveness, spread through tissue channels, angiogenesis and tumor vascularization. These latter processes depend upon the rates of proliferation of endothelial cells and smooth muscle cells.

Figure 6:
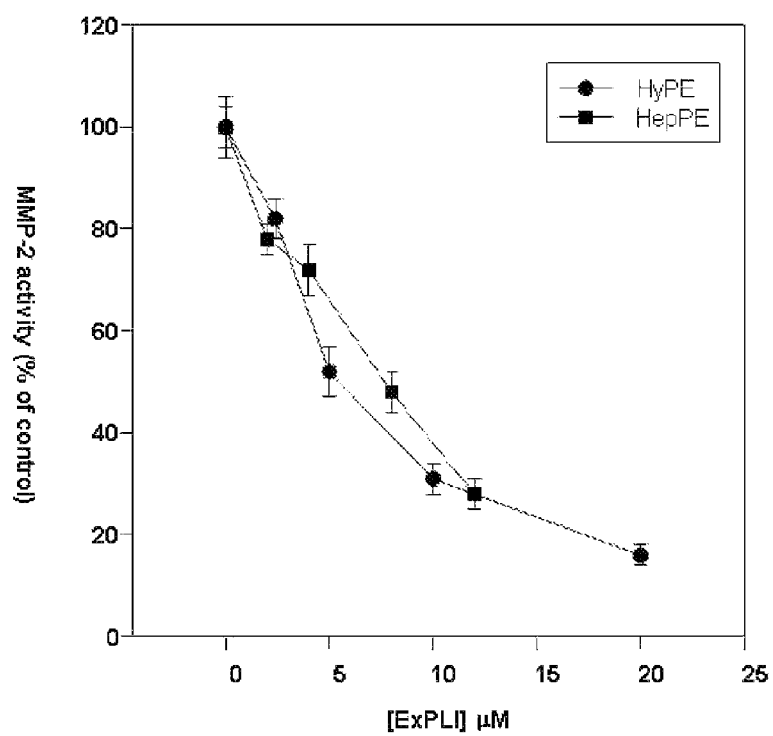
FIG. 6: A graph showing the effect of Lipid-conjugates on secretion of collagenase IV (MMP-2) by human fibrosarcoma cells.

Lipid-conjugates inhibit the production and activities of enzyme that break the basal membrane and enable the invasion of cancer cells, such as collagenase (metaloproteinase=MMP), heparinase and hyaluronidase:

To demonstrate the Lipid-conjugate effect on collagenase, HT-1080 (fibrosarcoma) cells were incubated for 24 h with HYPE at the indicated concentration. The culture medium was then collected and its collagenase activity was determined by a zymographic assay. Each datum is average of two plates (FIG. 6).

Figure 7:
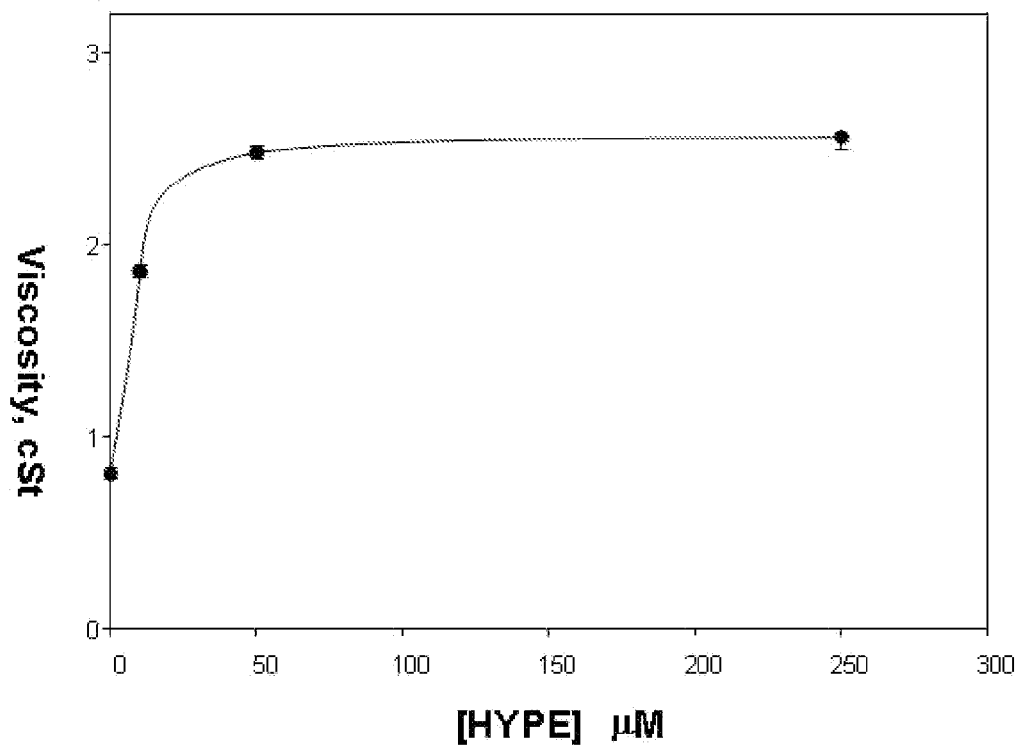
FIG. 7: A graph showing that HyPE inhibits hyaluronic acid degradation by hyaluronidase.

To demonstrate the ability of the Lipid-conjugates to inhibit hyaluronidase activity, hyaluronic acid (HA) in PBS (0.75 mg/ml) was interacted with hyaluronidase (15 U/ml) in the absence or presence of HYPE, at the indicated concentration for 1 h. HA degradation was determined by the change in the viscosity of its solution (FIG. 7).

Figure 8:
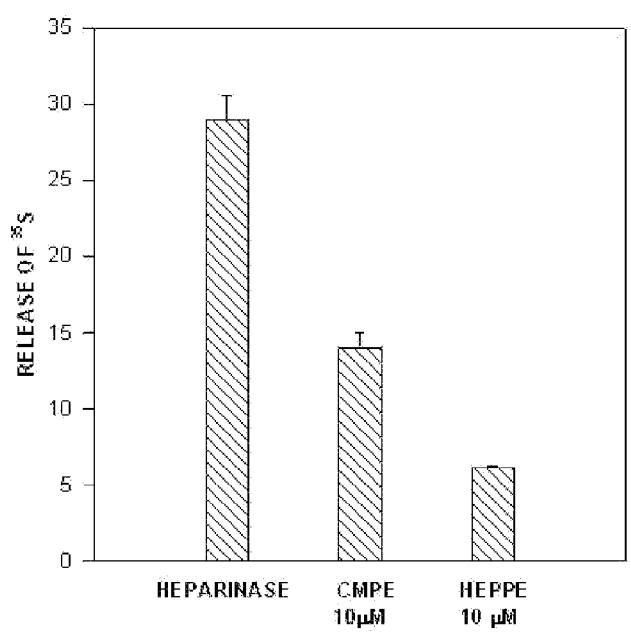
FIG. 8: A bar graph showing the Effect of Lipid-conjugates on the activity of exogenous heparinase.

To demonstrate the inhibition of heparinase activity by Lipid-conjugates, BGM cells were incubated overnight with 50 µCi $^{35}SO_4^{2-}$ per well (to label the cell surface glycosaminoglycans). The cells then were washed 3 times with PBS before treating with 5 units of heparinase I in 200 µl PBS for 3 h. The medium was collected and its $^{35}S$ content was counted (FIG. 8).

Figure 9A:
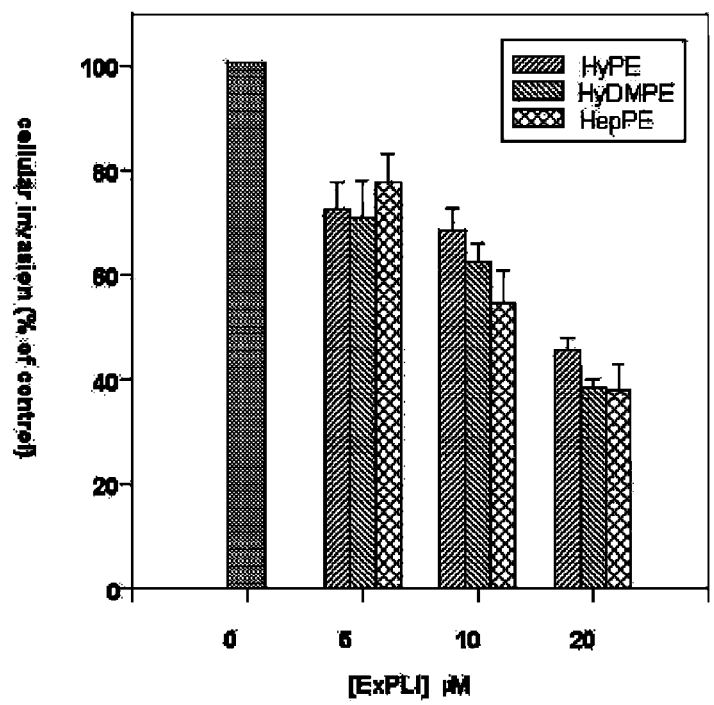
FIG. 9: A bar graph showing the effect of Lipid-conjugates on invasiveness of human fibrosarcoma cells (A); A bar graph showing the inhibitory effect of dipalmitoyl phosphatidylethanolamine hyaluronic acid (HyPE) and dimyristoyl phosphatidylethanolamine hyurolonic acid (HyDMPE) on invasiveness of human fibrosarcoma (HT-1080) cells (B).

For showing the ability of the Lipid-conjugates to inhibit the invasion of tumor cells through basement membrane, the chemoattractant invasion assay was used: Polycarbonate fibers, 8 µm pore size, were coated with 25 µg of a mixture of basement membrane components (Matrigel) and placed in modified Boyden chambers. The cells ($2 \times 10^5$) were released from their culture dishes by a short exposure to EDTA (1 mM), centrifuged, resuspended in 0.1% BSA/DMEM, and placed in the upper compartment of the Boyden chamber. Fibroblast conditioned medium was placed in the lower compartment as a source of chemoattractants. After incubation for 6 h at 37 C, the cells on the lower surface of the filter were stained with Diff-Quick (American Scientific Products) and were quantitated with an image analyzer (Optomax V) attached to an Olympus CK2 microscope. The data are expressed relative to the area occupied by untreated cells on the lower surface of the filter. (Albini et al., A Rapid In Vitro Assay for Quantitating the Invasive Potential of Tumor Cells. Cancer Res. 47:3239-3245, 1987). FIG. 9A demonstrates the Lipid-conjugate ability to attenuate cancer cell invasiveness. Basement Membrane Invasiveness.

Figure 9B:
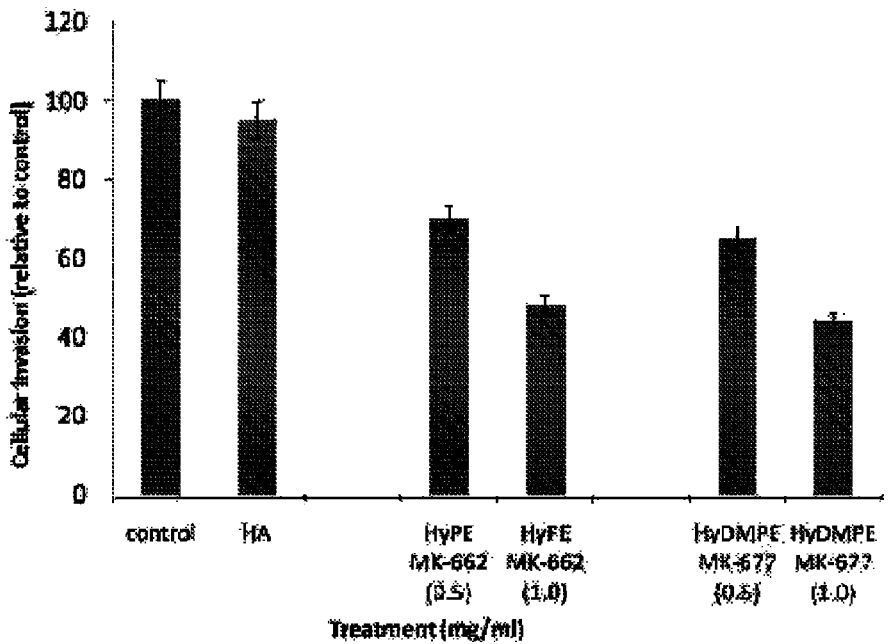

Further experiments utilizing a Boyden chamber for chemo-invasion assays were performed: Matrigel (25 ug) was dried on a polycarbonate filter (PVP-free, Nucleopore). Fibroblast-conditioned medium (obtained from confluent NIH-3T3 cells cultured in serum-free DMEM) was used as the chemo-attractant. HT-1080 human fibrosarcoma cells were harvested (by brief exposure to 1 mM EDTA), washed with DMEM containing 0.1% bovine serum albumin, and added to the Boyden chamber (200 k cells). The chambers were incubated in a humidified incubator at 37° C. (5% $CO_2$ 95% air) for 6 h. The cells that have traversed the Matrigel layer and attached to the lower surface of the filter were stained with Diff Quick (American Scientific Products) and counted. The results presented in FIG. 9B clearly demonstrated the inhibitory effect of dipalmitoyl phosphatidylethanolamine hyaluronic acid (HyPE) and dimyristoyl phosphatidylethanolamine hyurolonic acid (HyDMPE) indicate the actual compounds (FIG. 9B).

Figure 10:
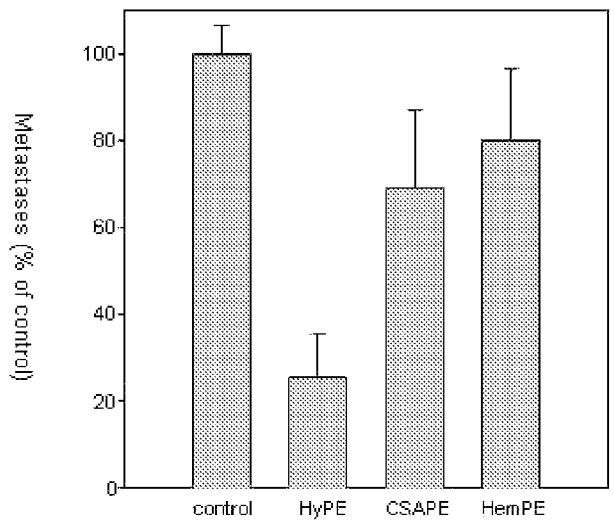
FIG. 10: A bar graph showing the effect of Lipid-conjugates on mouse lung metastases formation induced by mouse melanoma cells.

Effect of Lipid-conjugates on mouse lung metastases formation induced by mouse melanoma cells: $10^5$ B16 F10 mouse melanoma cells were injected I.V. into a mouse (20-25 g). Three weeks later the lungs were collected and the metastases on the lung surface counted. The Lipid-conjugate effect, illustrated in FIG. 10 was examined as follows: In experiment I, the indicated Lipid-conjugates was injected I.P. (1 mg/mouse) 5 times a week for 3 weeks starting on day 1 (total of 15 injections) (FIG. 8.8-I). In FIG. 8.8-II, HYPE (selected subsequently to experiment I) was injected I.P. (1 mg/mouse) as follows: A. 5 times a week for 3 weeks starting on day 1 (total of 15 injections); B. 5 times a week for 2 weeks starting from week 2 (total of 10 injections); C. One injection (I.P.) simultaneously with I.V. injection of the melanoma cells. D=Mice injected (I.P.) with hyaluronic acid alone (without PE), 5 times a week for 3 weeks, starting on day 1 (total of 15 injections). Each group included 6 mice. $*p<0.0001$, $p<1.10-5$, $*p<2.10-7$.

Figure 11:
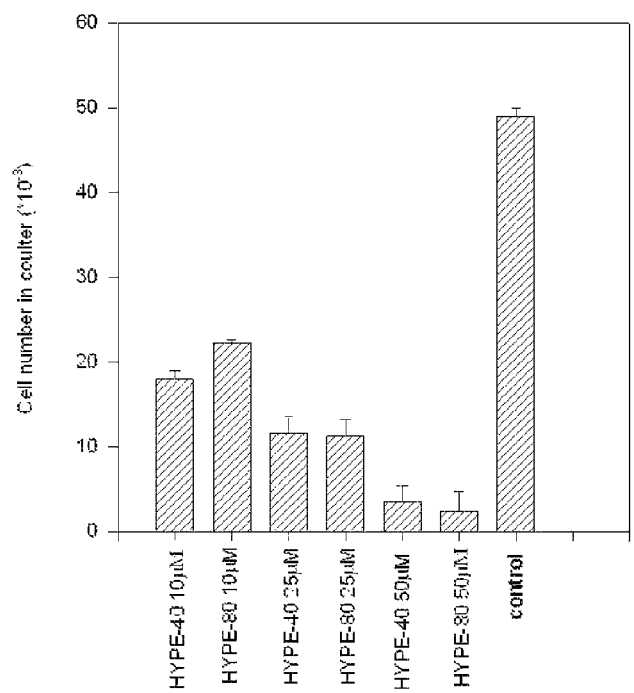
FIG. 11: A bar graph showing the effect of HyPE on bovine aortic smooth muscle cell (SMC) proliferation.

In addition, the anti-proliferative effects of the Lipid-conjugates on bovine aortic smooth muscle cells, unstimulated or stimulated by thrombin, and on the proliferation of human venous smooth muscle cells was demonstrated:

For unstimulated cells, bovine aortic smooth muscle cells were seeded at $7 \times 10^3$ cells per well (in 24-well plates), in DMEM supplemented with 10% FCS, in the absence or presence of HYPE-40 or HYPE-80 (enriched with PE), grown for 72 h, and counted in Coulter (FIG. 11).

For stimulated cells, bovine aortic smooth muscle cells were grown under the conditions as above for 48 h, following pre-incubation for 6 h, as indicated, with either thrombin, fetal calf serum, Lipid-conjugate, or both. Cell growth is represented as the amount of thymidine incorporation (FIG. 12).

Smooth muscle cells (SMC) from human saphenous vein, were inoculated at $8 \times 10^4$/cells/5 mm culture dish, in DMEM supplemented with 5% fetal calf serum and 5% human serum. A day later the cells were washed and incubated in the same culture medium in the absence (control) or presence of the Lipid-conjugate (HEPPE) or its polymeric carrier (heparin, at the same concentration as the HEPPE). After 5 days the cells were harvested (by trypsinization) and counted (FIG. 13). Each datum is mean±SEM for 3 replications (the same results were obtained in a second reproducible experiment). $*p<0.005$.

These results also demonstrate the capacity of the Lipid-conjugates to control the proliferation of smooth muscle cells, which is essential for tumor vascularization subsequent to capillary formation by endothelial cells.

Taken together, the experiments described above, demonstrate that administration of the Lipid-conjugates are effective therapy in the treatment of cancer growth and metastasis, by a plurality of mechanisms, including suppression of cell proliferation, invasion of cancer cells, angiogenesis and metastasis formation and tumor vascularization Thus, Lipid-conjugates are effective therapy for cellular proliferative disorders, such as cancer. The process of cancer spread entails multiple events, each of these is a worthy target for inhibitory drug action, including the rate of cell-proliferation, the rate of spread through blood vessels, the rate of invasiveness through contiguous and non-contiguous (metastases) tissues, and the rate of production of new blood vessels to supply the cancerous growth. Cancer cells frequently produce intracellular matrix tissue degrading enzymes which serve to enhance their invasive potential. Cancer is thus a multiphasic disease involving the process of tissue invasiveness, spread through tissue channels, angiogenesis and tumor vascularization. These latter processes depend upon the rates of proliferation of endothelial cells and smooth muscle cells.

Example 3

Glycolipid Conjugates Modulate Chemokine and/or Cytokine Expression

The effects of the Lipid-conjugates were tested in the following cell lines: 16HBE, IB-3 and C-38 cells.

Studies of the pathogenesis of rheumatoid arthritis (RA) have revealed that both synovial fibroblasts and T cells participate in the perpetuation of joint inflammation as dynamic partners in a mutual activation feedback, via secretion of cytokines and chemokines that stimulate each other. IL-8 is frequently found at high levels in diseases associated with neutrophil. influx, and during the course of rheumatoid arthritis. IL-6 is frequently found at high levels in diseases associated with neutrophil. influx, and during the course of rheumatoid arthritis.

The cells were grown to confluency in 96 well plates, washed, and Lipid-conjugates (Compounds XXII, XXIII, and XXV) or sham were added to the cells, which were incubated at 37° C. for 30 minutes. Cells were washed, and in some groups, incubated with heat-killed $P.\ aeruginosa$ PAO1 ($5 \times 10^7$ cfu/ml) for 24 hours. Cells were then washed extensively and incubated in fresh media containing gentamicin (100 μg/ml). Supernatants were then harvested, and IL-8 levels were assayed by ELISA. The data was analyzed for statistical significance using an ANOVA.

Figure 5:
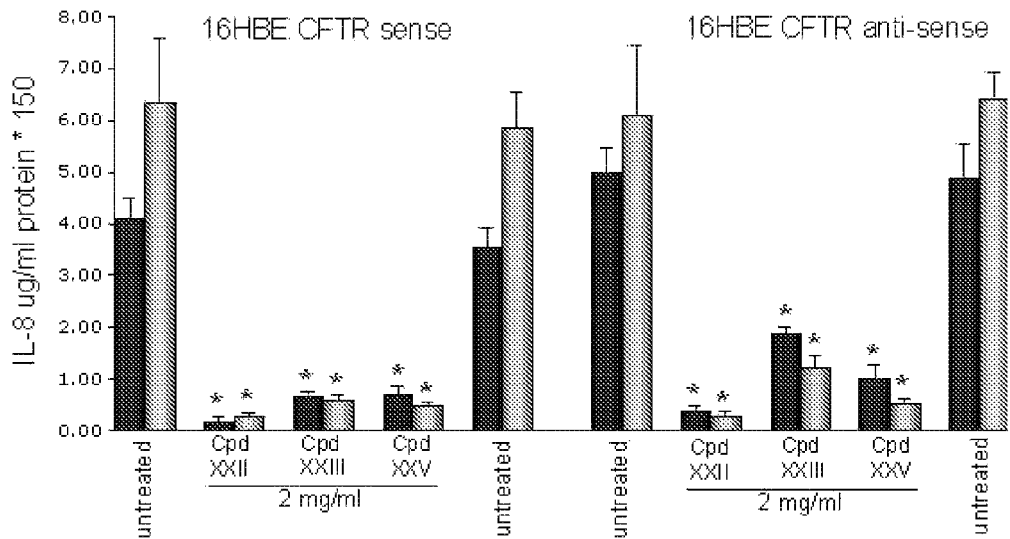
FIG. 5A: Effect of Lipid-conjugates on cytokine levels in Pseudomonas-infected and uninfected 16HBE+CFTR sense and 16HBE+CFTR antisense bronchial epithelial cells.
FIG. 5B: Effect of Lipid-conjugates on cytokine levels in Pseudomonas-infected and uninfected C38 and IB3 bronchial epithelial cells.

Data presented in FIG. 4B demonstrate that Lipid-conjugates significantly and dose-dependently suppress IL-8 expression in both mutant CFTR and control cell lines (FIGS. 5A and 5B). Further, IL-8 suppression by Lipid-conjugates is present both in cells exposed to PAO1 and in uninfected cells (FIGS. 4A and 5B). Additionally, Lipid-conjugates inhibit endogenous IL-8 production associated with mutant CFTR. Thus, Lipid-conjugates may be useful in decreasing inflammatory symptoms in arthritis patients, both those that are suffering from an infection and those that are not.

The levels of other chemokines and cytokines in the cell supernatants are determined by ELISA as described hereinabove.

In order to determine whether NF-kB activation occurs in the sham versus treated cells, cells are transfected with a NF-kB luciferase construct using Fugene. 24 hours following transfection, cells are weaned from serum, incubated for 18 hours, then treated with the compounds, or sham, respectively. Additional groups include cells infected with PAO1 for 60 minutes, then processed as described. Cell lysates are screened for luciferase activity.

Effects of Lipid-conjugates on the activation of other transcription factors that may be relevant to arthritis may be similarly evaluated, via construction of luciferase constructs, via methods known in the art. Microarrays for screening for effects of the compounds on multiple proinflammatory genes, versus sham treated cells, may also be evaluated.

Example 4

Immobilized Phosphatidylethanolamine (PE) Inhibitors of Extracellular PLA2

Polysaccharide-immobilized phosphatidylethanolamine (PE) provided the following results:

| | | | |
|---|---|---|---|
| MK645, | Hyaluronic acid/PE; | av MW = 50-200 kDa. | $K_{1/2}$ = kill |
| MK 723/4, | Hemacell/PE, | av. MW = 30 kDa. | $K_{1/2}$ = 5 μM |
| MK691, | Chondroitin SO$_4$/PE, | av. MW~50 kDa. | $K_{1/2}$ = >1 μM, kill |
| MK713/4 | Dextran/PE | av. MW = 40 kDa. | $K_{1/2}$ = >30 μM |
| MK714/1 | Dextran/PE | av. MW = 40 kDa. | $K_{1/2}$ = 4 μM |

Samples were prepared at 20 mg/ml in PBS buffer, and were suspended by vigorous vortexing, shaking at 37° C., and "tip" or bath sonicated for 20 seconds. MK723/4 dissolved easily. The others compounds proved more difficult to dissolve, but ultimately did using these conditions.

The compounds were assessed for their ability to inhibit IL-8 secretion from IB3-1 cells, with the most potent compound being MK714/1. Based on the calculated PE content, the $K_{1/2}$ was estimated to be roughly 4 μM. The order of activity was: MK714/1>MK723/4>MK713/4>>[MK645, MK691].

The values of $K_{1/2}$ given in the table are calculated from the concentration of PE's on each molecule of carrier polysaccharide rather than on mg/ml of each complex adduct.

MK645 (at 1 mg/ml) and MK723/4 (at 0.2 mg/ml) were found to be toxic to IB3-1 cells when incubated for 24 hours, while the other compounds were not.

Example 5

Cardiovascular Disease

The Lipid-conjugates are effective therapy for ischemic vascular disease, atherosclerosis, and reperfusion injury. This is demonstrated in the following experiments.

A prominent feature in the pathogenesis of atherosclerosis is the accumulation of blood lipoproteins, such as oxidized LDL (oLDL), in cells lining vascular walls, and the proliferation of cells lining and within vascular walls, such as smooth muscle cells. The resultant narrowing of the blood vessel lumen at the site of the atherosclerotic lesion may give rise to varying degrees of tissue ischemia. While ischemic events may be reversible, either spontaneously or through medical intervention, the process of tissue injury may persist to the stage of reperfusion injury, in which the previously ischemic tissue is still at risk for damage, through several mechanisms, including oxidative damage.

Figure 14:
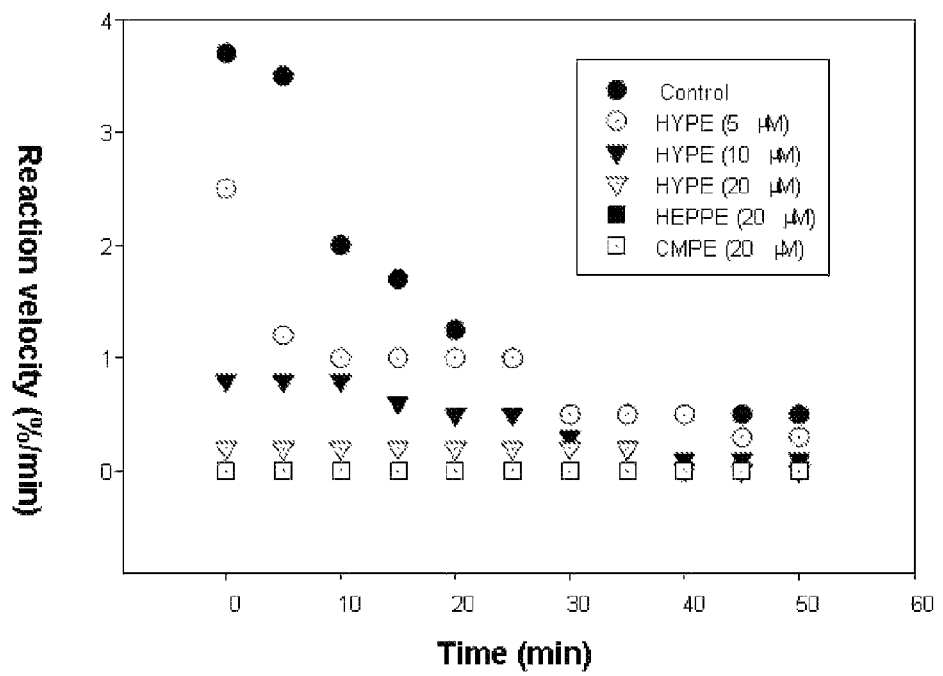
FIG. 14: A graph showing the effect of Lipid-conjugates on LDL-endogenous phospholipase A₂ activity.

LDL-PLA$_2$. Endogenous LDL-phospholipase A$_2$ (PLA$_2$) hydrolyzes LDL-phospholipids to form lyso-phospholipids, which are chemotactic and facilitate LDL oxidation and uptake by blood vessel wall cells. For demonstrating that the Lipid-conjugates inhibit LDL-associated PLA$_2$ activity, LDL (0.1 μM) was incubated for 15 min at 37° C. in the absence or presence of HYPE, HEPPE or CMPE at the concentrations indicated (FIG. 14). At time zero $C_6$—NBD-PC (0.5 μM) was added to the dispersion. This resulted in an instantaneous increase of fluorescence intensity (due to incorporation of NBD into lipidic cores). When LDL was incubated alone the increase of fluorescence was followed by time-dependent decrease of fluorescence intensity that can be attributed to hydrolysis of the LDL-associated PLA (and subsequent departure of the resultant NBD-caproic acid from the LDL particle to the aqueous medium). When LDL was incubated in the presence of HYPE, HEPPE or CMPE this time-dependent decrease was fully or partially inhibited.

To demonstrate that the Lipid-conjugates inhibit LDL uptake by cultured macrophages and in whole animals, human LDL (isolated by the conventional method of floatation) were subjected to $Cu^{2+}$-induced oxidation, and labeled with $^{125}I$. Confluent J774 macrophages were incubated with 100 μM $^{125}I$-oLDL and Lipid-conjugate at the indicated concentration in PBS buffer (pH=7.4) supplemented with 0.5% BSA, for 3 h. The cells were then washed 4 times with the PBS/BSA, and subjected to lysis by 0.1 N NaOH for 30 min. The cell lysate was collected and the $^{125}I$ content was determined in a radioactivity counter (Table 4).

TABLE 4

Inhibition of Oxidized LDL Uptake in macrophages by HYPE and HEPPE

| Treatment | Cell-associated $^{125}I$-oLDL (DPM × $10^{-3}$) | % Inhibition |
| --- | --- | --- |
| Control | 92.2 ± 4.0 | |
| 10 μM HYPE | 20.9 ± 1.7 | 78% |
| 20 μM HEPPE | 59.2 ± 8.3 | 37% |

Figure 15:
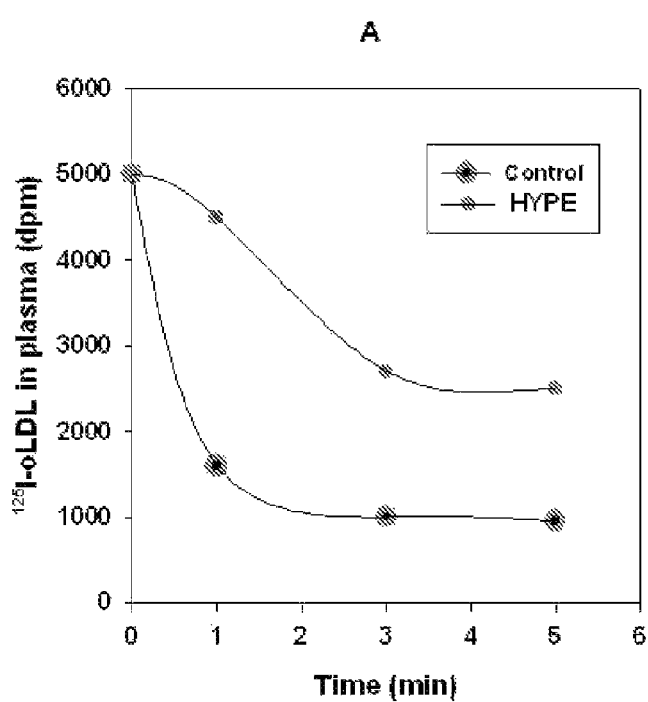
FIG. 15: A graph showing the effect of HyPE on uptake of oxidized LDL (ox LDL).

Uptake of oLDL in-vivo: Rats weighing 200 g were injected I.V. with 0.4 ml saline containing 250 nmole of $Cu^{2+}$-induced oxidized LDL labeled with $^{125}I$, and 200 nmole of HYPE. Blood samples were drawn at the indicated time intervals and the $^{125}I$ radioactivity in the plasma was counted (FIG. 15).

These experiments demonstrate that administration of Lipid-conjugates is effective therapy in the treatment of cardiovascular disease, including atherosclerosis. Additional support for the capacity of the Lipid-conjugates to treat cardiovascular diseases is provided herein below, showing that the Lipid-conjugates inhibit proliferation of smooth muscle cells, and protect LDL from oxidative damage.

Example 6

Prophylaxis for Invasive Surgical Procedures, Including Catheterization

The Lipid-conjugates are effective in the treatment and prophylaxis for cardiovascular disease in many settings, including atherosclerosis, as described above, as well as in the setting of stenosis and restenosis induced by ischemia/reperfusion injury. The lipid-conjugates are effective in preventing the formation of stenotic lesions as may occur in the course of invasive surgical procedures which involve manipulation of vascular organs, in particular vascular catheterization.

Ischemia/reperfusion injury: As noted above, the injury induced by ischemia and reperfusion, is the major stimulant for stenosis subsequent to catheterization, surgery or other procedures that involve vascular obstruction and occlusion. To demonstrate the ability of the Lipid-conjugates to ameliorate this injury, they were tested for inhibition of white cell adhesion and extravasaion, which express ischemia/reperfusion injury to blood vessels. Leukocytes were labeled in vivo by I.V. injection of rhodamine. Ischemia was applied to exposed cremaster muscle in rats (in situ) for 90 min, and then blood flow was restored for reperfusion. The fluorescent-labeled leukocytes adherent to blood vessel walls (FIG. 16A) and those extravasated to the extravascular space (FIG. 16B) were videotaped and counted at the indicated time point during the reperfusion period. Lipid-conjugates (10 mg/100 g body weight) were injected I.V. 40 min and 10 min prior to induction of ischemia. FIGS. 16A and 16B show that administration of Lipid-conjugates efficiently suppresses the ischemia/reperfusion-induced adhesion and extravasation of leukocytes. Each datum is mean±SEM obtained from 5 rats with HYPE and 3 rats with HEPPE. p<0.005.

Figure 17:
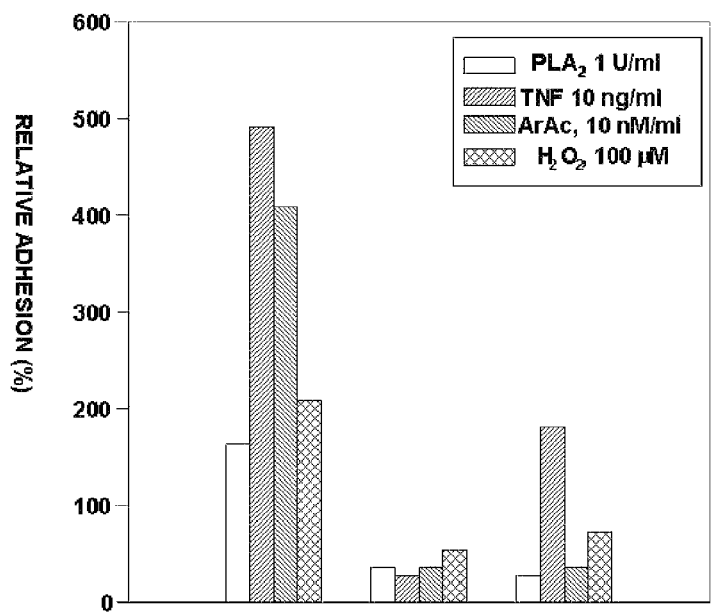
FIG. 17: A bar graph showing the effect of Lipid-conjugates on red blood cell (RBC) adhesion to activated endothelial cells (EC).

Another expression of damage to blood vessel wall endothelium is adhesion of red blood cells (RBC) to endothelial cells upon their activation by oxygen radicals, lipid mediators or cytokines (produced subsequent to ischemia reperfusion injury). RBC adherence further facilitates vascular occlusion. For demonstrating the protective effect of Lipid-conjugates on endothelium, bovine aortic endothelial cells were exposed to either tumor necrosis factor (TNF-α), phospholipase $A_2$, arachidonic acid, or hydrogen peroxide, and then assayed for cytodamage, as judged by adhesion of red blood cells as an index of endothelial intactness. Bovine aortic endothelial cells (BAEC) were pre-incubated for 30 min with either 5 μM CMPE or 20 μM DEXPE, then washed and stimulated for 18 h with TNF, ArAr, or $PLA_2$ at the indicated concentration. For stimulation with $H_2O_2$, the cells were treated with $H_2O_2$ for 20 min, then washed and incubated in the control culture medium for 18 h. The BAEC were washed and incubated with human red blood cells (RBC) for 30 min. The cultures were washed and the RBC which remained adhering to the BAEC were counted under a microscope (FIG. 17).

Balloon-induced stenosis in rats: To demonstrate the efficacy of Lipid-conjugates in protocols for balloon-induced stenosis in rats, in the carotid artery by both systemic (Table 5) and intravenous infusion administration. Rats were pre-treated with I.P. injection of 10 mg/100 g body weight of HYPE in PBS, or PBS alone, 1 day, and also 1-2 hours before injury. Injury was achieved using the standard Fogarty catheter. The rats were injected with the same amount of drug or vehicle every day for 3 days, and then every other day, for a total of 8 injections. Rat were sacrificed on the $14^{th}$ day, the arteries were processed according to standard procedure. Half of the rats were injected with bromodeoxyuridine (BrdU), fixed with formalin and triton, and processed for BrdU staining, and areas of the indicated vascular structures measured for comparison (Table 5). The distal left common and external carotid arteries were exposed through a midline incision in the neck. The left common carotid artery was denuded of endothelium by the intraluminal passage of a 2F Fogarty balloon catheter (Baxter, Santa Anna, Calif.) introduced through the external carotid artery. The catheter was passed three times with the balloon distended sufficiently with saline to generate a slight resistance. The catheter was then removed and a polyethylene tube (PE-10) connected to a syringe was introduced into the common carotid artery. A segment of the common carotid artery was temporarily isolated by sliding ligature and vascular clamp. Approximately 50 μl of solution containing 10 nmole of CMPE was injected into isolated arterial segment and left in place for 15 min. The drug solution was then evacuated and the external carotid artery was ligated. The rats were sacrificed 2 weeks later, and the percent of luminal stenosis (in the damaged area) was determined by histological measurement of neointima (N) to media (M) area ratio (Table 5).

TABLE 5

Inhibition of Balloon-Induced Stenosis in Rats by Lipid-Conjugates

| Experiment | Treatment | % stenosis (Mean ± SEM) | P | N/M | P |
|---|---|---|---|---|---|
| I.P administration | Untreated (n = 7) | 53.96 ± 4.11 | 0.003 | 1.64 ± 0.12 | 0.001 |
| | HyPE (n = 6) | 53.96 ± 2.89 | | 1.0 ± 0.08 | |
| I.P. administration | Untreated (n = 6) | 41.53 ± 4.84 | 0.023 | 1.16 ± 0.12 | 0.036 |
| | CMPE (n = 8) | 21.89 ± 5.42 | | 0.64 ± 0.17 | |
| Intra-arterial Administration | Untreated (n = 4) | 53.12 ± 12.8 | 0.052 | 1.61 ± 0.17 | 0.008 |
| | CMPE (n = 6) | 29.64 ± 2.17 | | 0.99 ± 0.08 | |

These experiments demonstrate that administration of Lipid-conjugates are effective therapy in the treatment of cardiovascular disease, by a plurality of mechanisms, including inhibition of vascular smooth muscle cell proliferation, uptake of lipoprotein, oxidative stress, and leukocyte activation in models of ischemia and reperfusion. Administration of Lipid-conjugates is of both prophylactic and acute therapeutic benefit when administered in the course of invasive arterial procedures, particularly balloon angioplasty.

Example 7

Anti-Oxidant Therapy

The Lipid-conjugates are effective therapy for preventing oxidative damage. The noxious effect of peroxide free radicals on living tissue is known as oxidative damage. When cell membranes are the targets for this damaging process, membrane dysfunction and instability result. Oxidative damage to blood proteins, particularly blood lipid proteins, results in their over-accumulation in cells lining the vasculature, thus contributing to atherogenesis. In fact, oxidative cell damage is a major mechanism attributed to the process of aging or senescence.

Oxidative damage to proteins or cell membranes is commonly assessed by exposing these tissues to hydrogen peroxide produced by the enzyme glucose oxidase (GO), in the absence or presence of additional membrane destabilizing agents, such as $PLA_2$, or by exposure to divalent cations, such as copper.

The following experiments demonstrate the ability of Lipid-conjugates to preserve cells from oxidative damage, as judged by the cells' retention of both arachidonic acid and of low molecular weight intracellular substances.

Figure 18:
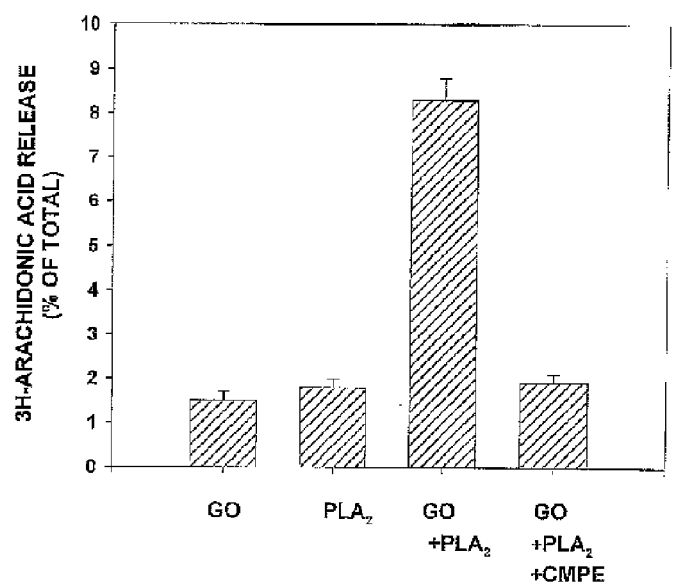
FIG. 18: A graph showing that CMPE protects BGM cells from membrane lysis induced by combined action of hydrogen peroxide (produced by glucose oxidase=GO), and exogenous phospholipase A₂ (PLA₂).

Confluent BGM (green monkey kidney epithelial cells) were labeled with $^3$H-arachidonic acid. The cells were treated with CMPE for 30 min prior to treatment with GO and $PLA_2$ (0.5 u/ml) (FIG. 18).

Figure 19:
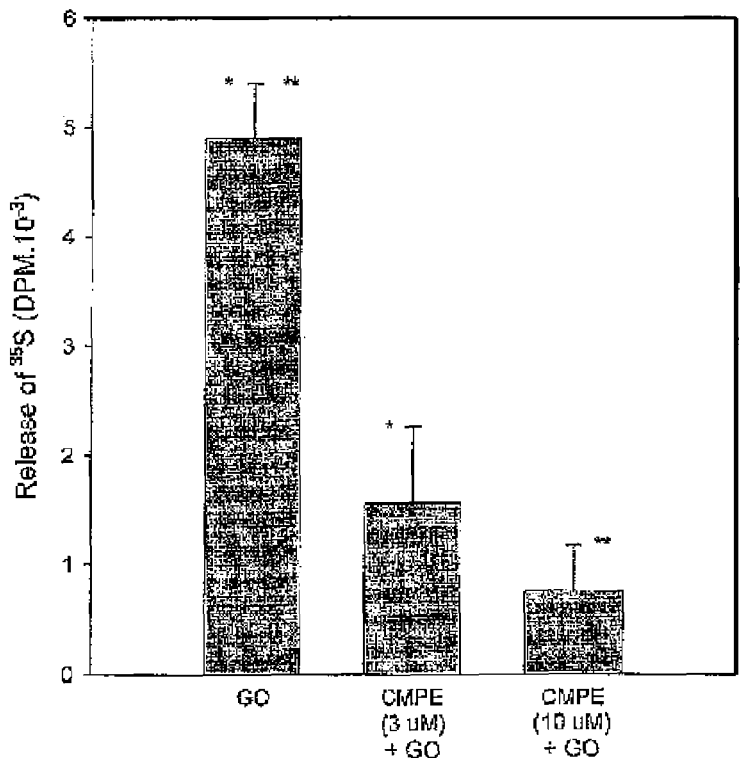
FIG. 19: A graph showing that CMPE protects BGM cells from glycosaminoglycan degradation by Hydrogen peroxide (produced by GO).

BGM cells were labeled with $^{35}SO_4$ overnight. The cells were washed with DMEM (containing 10 mg/ml BSA) 4 times with PBS. The cells were then incubated in DMEM supplemented with GO (an $H_2O_2$ generation) for 90, and the culture medium was collected and counted for $^{35}S$ radioactivity. For treatment with CMPE cells were incubated with CMPE, at the indicated concentration for 30 min prior to introduction of GO. Each datum is MEAN+SEM for 5 replications. *p<0.005; **p<0.001 (FIG. 19).

Figure 20:
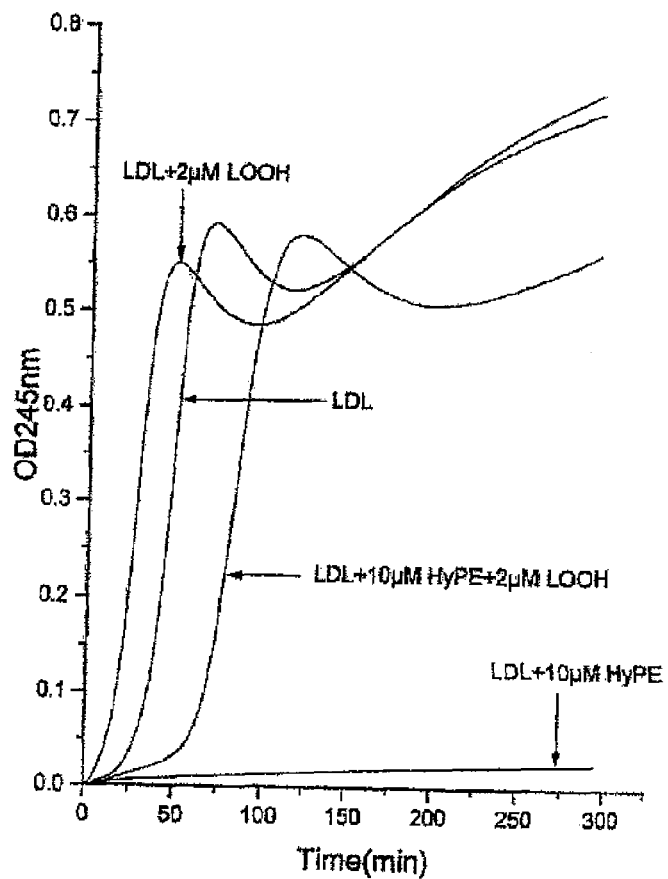
FIG. 20: A graph showing that HyPE protects LDL from copper-induced oxidation.

For demonstrating the ability of Lipid-conjugates to inhibit the oxidation of blood lipoprotein. LDL (0.1 µM) was incubated in the absence and presence of various concentrations of HYPE or HA at 37° C. At time zero 5 µM $CuCl_2$ was added to the dispersions and the mixtures were continuously monitored for oxidation products at 245 nm (FIG. 20). The absorbance at 245 (OD units) is depicted as a function of time (Shnitzer et al., Free Radical Biol Med 24; 1294-1303, 1998).

Additional support for the anti-oxidant capacity of the Lipid-conjugates is provided by the following experiment above, showing their inhibitory effect on ischemia/reperfusion-induced activation of white cells.

These experiments demonstrate that administration of Lipid-conjugates is effective therapy in the prevention of tissue damage induced by oxidative stress (associated with free radical and hydrogen peroxide production) by a plurality of mechanisms, including inhibiting the oxidation of lipoprotein, as well as their uptake, inhibiting arachidonic acid release, and preserving the integrity of cell membranes (inhibiting GAG degradation), including red blood cell membranes, as described below.

Example 8

Toxicity Tests

The following compounds were tested: HyPE, CMPE, CSAPE and HepPE. The compounds were injected IP at one dose of 1000, 500 or 200 mg/Kg body weight. Toxicity was evaluated after one week, by mortality, body weight, hematocrit, blood count (red and white cells), and visual examination of internal organs after sacrifice. These were compared to control, untreated mice. Each dose was applied to a group of three mice. No significant change in the above criteria was induced by treatment with these compounds, except for the HepPE, which induced hemorrhage.

The non-toxicity of the Lipid conjugates is demonstrated in Table 6 and Table 7, depicting the results obtained for HyPE in acute (6) and long-term (7) toxicity tests.

TABLE 6

| | Acute toxicity | | | | |
|---|---|---|---|---|---|
| Dose of HyPE (mg/kg body weight) | Body weight (g) | | RBC × $10^6$ | WBC × $10^3$ | Hematocrit % |
| 0.0 (control) | 21.9 ± 0.2 | 22.6 ± 0.3 | 10.7 ± 0.4 | 9.3 ± 0.3 | 45.0 ± 0.5 |
| 250 | 22.1 ± 0.4 | 23.1 ± 0.6 | 11.4 ± 0.1 | 7.7 ± 0.2 | 43.3 ± 0.7 |

TABLE 6-continued

| | Acute toxicity | | | |
|---|---|---|---|---|
| Dose of HyPE (mg/kg body weight) | Body weight (g) | | RBC × $10^6$ | WBC × $10^3$ | Hematocrit % |
| 500 | 21.4 ± 0.3 | 22.3 ± 0.4 | 11.5 ± 0.3 | 8.1 ± 1.3 | 44.7 ± 2.3 |
| 1000 | 21.7 ± 0.2 | 22.1 ± 0.2 | 10.9 ± 0.4 | 7.4 ± 0.6 | 40.3 ± 0.7 |

RBC = red blood cells.
WBC = white blood cells.
Each datum is mean ± SEM.

For long-term toxicity test of HyPE, a group of 6 mice received a dose of 100 mg HyPE/Kg body weight, injected IP 3 times a week for 30 weeks (total of 180 mg to a mouse of 20 g). Toxicity was evaluated as for Table 5. No mortality, and no significant change in the above criteria was induced by this treatment, compared to normal untreated mice (see Table 6), as depicted in Table 7.

TABLE 7

| | Results at week 30: | | | |
|---|---|---|---|---|
| | Body weight (g) | RBC × $10^6$ | WBC × $10^3$ | Hematocrit % |
| Control (untreated) rats | 39.5 ± 3.1 | 10.9 ± 0.8 | 9.3 ± 0.6 | 45.0 ± 0.8 |
| HyPE-injected rats | 39.0 ± 2.7 | 11.7 ± 0.7 | 8.1 ± 15 | 43.4 ± 4.9 |

I claim:

1. A method of inhibiting the accumulation of LDL in a subject in need thereof, comprising the step of administering to said subject a composition comprising a compound of general formula (I):

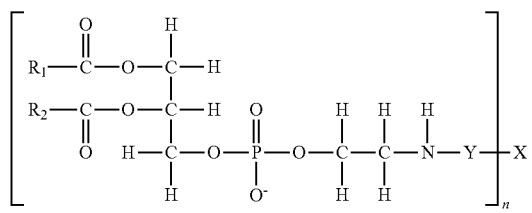

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a glycosaminoglycan; and n is a number from 2 to 1000;

wherein if Y is nothing, the phosphatidylethanolamine is directly linked to X via an amide bond and if Y is a spacer, said spacer is a straight or branched chain alkylene selected from the group consisting of —CO-alkylene-CO—, —NH-alkylene-NH—, and —CO-alkylene-NH—, and said spacer is directly linked to X via an amide or an esteric bond and to said phosphatidylethanolamine via an amide bond, thereby inhibiting the accumulation of LDL in a said subject.

2. The method of claim 1, wherein said glycosaminoglycan is hyaluronic acid, heparin, heparin sulfate, chondroitin, chondroitin sulfate, keratan, keratan sulfate, dermatan sulfate or a derivative thereof.

3. The method of claim 2, wherein said compound comprises sugar rings of said glycosaminoglycan, which are intact.

4. The method of claim 1, wherein each of R1 and R2 is dipalmitoyl or dimyristoyl.

5. The method of claim 1, wherein said subject has atherosclerosis.

6. The method of claim 1, wherein said LDL is oxidized LDL.

7. The method of claim 1, wherein said glycosaminoglycan has a molecular weight of 5000 to 10,000 Daltons.

8. The method of claim 1, wherein said glycosaminoglycan has a molecular weight of 10,000 to 20,000 Daltons.

9. The method of claim 1, wherein n is a number from 2 to 100.

10. The method of claim 1, wherein said compound is administered intravenously.

* * * * *